United States Patent
Carson et al.

(10) Patent No.: US 7,488,409 B1
(45) Date of Patent: Feb. 10, 2009

(54) MEDIATED ELECTROCHEMICAL OXIDATION OF ANIMAL WASTE MATERIALS

(75) Inventors: Roger W. Carson, Vienna, VA (US); Bruce W. Bremer, Montgomery Village, MD (US)

(73) Assignee: Scimist, Inc., Vienna, VA (US)

( * ) Notice: Subject to any disclaimer, the term of this patent is extended or adjusted under 35 U.S.C. 154(b) by 190 days.

(21) Appl. No.: 10/263,810

(22) Filed: Oct. 4, 2002

Related U.S. Application Data

(60) Provisional application No. 60/327,005, filed on Oct. 5, 2001.

(51) Int. Cl.
  *C25B 1/00* (2006.01)
(52) U.S. Cl. .................. 205/701; 205/688; 205/703; 205/746; 205/749; 204/252; 204/259; 204/262; 204/263; 204/266
(58) Field of Classification Search ............. 205/701, 205/688, 703, 746, 749; 588/204; 204/252, 204/259, 262, 263, 266
See application file for complete search history.

(56) References Cited

U.S. PATENT DOCUMENTS

| | | | |
|---|---|---|---|
| 4,013,552 A | 3/1977 | Kreuter |  |
| 4,069,371 A | 1/1978 | Zito |  |
| 4,749,519 A | 6/1988 | Koehly et al. |  |
| 4,752,364 A * | 6/1988 | Dhooge |  |
| 4,874,485 A | 10/1989 | Steele |  |
| 4,925,643 A | 5/1990 | Steele |  |
| 4,967,673 A | 11/1990 | Gunn |  |
| 5,047,224 A | 9/1991 | Dhooge |  |
| 5,261,336 A | 11/1993 | Williams |  |
| 5,380,445 A | 1/1995 | Rivard et al. |  |
| 5,516,972 A | 5/1996 | Farmer et al. |  |
| 5,707,508 A * | 1/1998 | Surma et al. | 205/688 |
| 5,756,874 A | 5/1998 | Steward |  |

(Continued)

FOREIGN PATENT DOCUMENTS

DE 4113817 11/1991

(Continued)

OTHER PUBLICATIONS

Davidson, L. et al.; *Ruthenium-Mediated Electrochemical Destruction of Organic Wastes*; Platinum Metal Reviews; 1998; vo. 42, No. 3; pp. 90-98 (Ruthenium).

(Continued)

*Primary Examiner*—Arun S. Phasge
(74) *Attorney, Agent, or Firm*—James Creighton Wray

(57) ABSTRACT

Animal waste is contacted with an electrolyte containing the oxidized form of one or more reversible redox couples, produced electrochemically by anodic oxidation at the anode of an electrochemical cell. The oxidized forms of any other redox couples present are produced either by similar anodic oxidation or reaction with the oxidized form of other redox couples present and capable of affecting the required redox reaction. The oxidized species of the redox couples oxidize the organic waste molecules and are themselves converted to their reduced form, whereupon they are reoxidized by either of the aforementioned mechanisms. The redox cycle continues until all oxidizable waste species, including intermediate reaction products, have undergone the desired degree of oxidation. The entire process takes place between zero degrees centigrade and slightly below the boiling point of the electrolyte, avoiding formation of either dioxins or furans. Ultrasonic energy and/or ultraviolet radiation provide reaction enhancements.

27 Claims, 7 Drawing Sheets

U.S. PATENT DOCUMENTS

| | | | |
|---|---|---|---|
| 5,810,995 | A | 9/1998 | Soilleux et al. |
| 5,855,763 | A | 1/1999 | Conlin et al. |
| 5,911,868 | A | 6/1999 | Balazs et al. |
| 5,919,350 | A | 7/1999 | Balazs et al. |
| 5,952,542 | A | 9/1999 | Steele |
| 5,968,337 | A | 10/1999 | Surma et al. |
| 6,210,078 | B1 * | 4/2001 | Redwine et al. ............. 405/263 |
| 6,402,932 | B1 * | 6/2002 | Bremer et al. ............. 205/701 |

FOREIGN PATENT DOCUMENTS

| | | | |
|---|---|---|---|
| DE | 4205739 | | 8/1993 |
| WO | WO97/15356 | | 5/1997 |
| WO | WO99/28239 | * | 6/1999 |

OTHER PUBLICATIONS

Morrison, R. & Boyd, R. (Editors); *Organic Chemistry*; New York University; Allen & Bacon, Inc.; 1973; (Third Edition); Chapter 1—Structure & Properties; pp. 1-2 (Organic).

Pletcher, D. & Walsh, F.; *Industrial Electrochemistry*; 1990; Chapman & Hall; Chapters 1 & 2; pp. 1-172.

Surma et al.; *Catalyzed Electrochemical Oxidation (CEO) of Rocky Flats Contaminated Combustible Materials*; Mar. 1996; Report prepared for U.S. Department of Energy, Pacific Northwest National Laboratory, Richland, WA; 25 pages.

Steward Tony; *Electrochemical Oxidation of Hazardous Organics*; Sep. 20, 1996; EO Systems, Inc.; 2 pages.

Whaley, S.; *UNR Attacks Hazardous Waste Riddle*; Las Vegas Review-Journal Oct. 21, 1997; 3 pages.

Lewis, R.; *Hawley's Condensed Chemical Dictionary*; Twelfth Edition; 1993; Van Nostrand—Reinhold; 4 pages.

Anonymous; *Chemical Storage Tank Systems—Good Practice Guide (Summary Guidance Document)*; CIRIA Publication WO02; Classic House, 174-180 Old Street, London, EC1V-98P, England, 43 pages.

Chiba et al.; *Mediated Electrochemical Oxidation as an Alternative to Incineration for Mixed Wastes*; Lawrence Livermore National Laboratory Paper (UCRL-JC-119133) prepared for WM95 Synposia, Tucson, AZ, Mar. 1, 1995 (dated Feb. 1995) (12 pages).

* cited by examiner

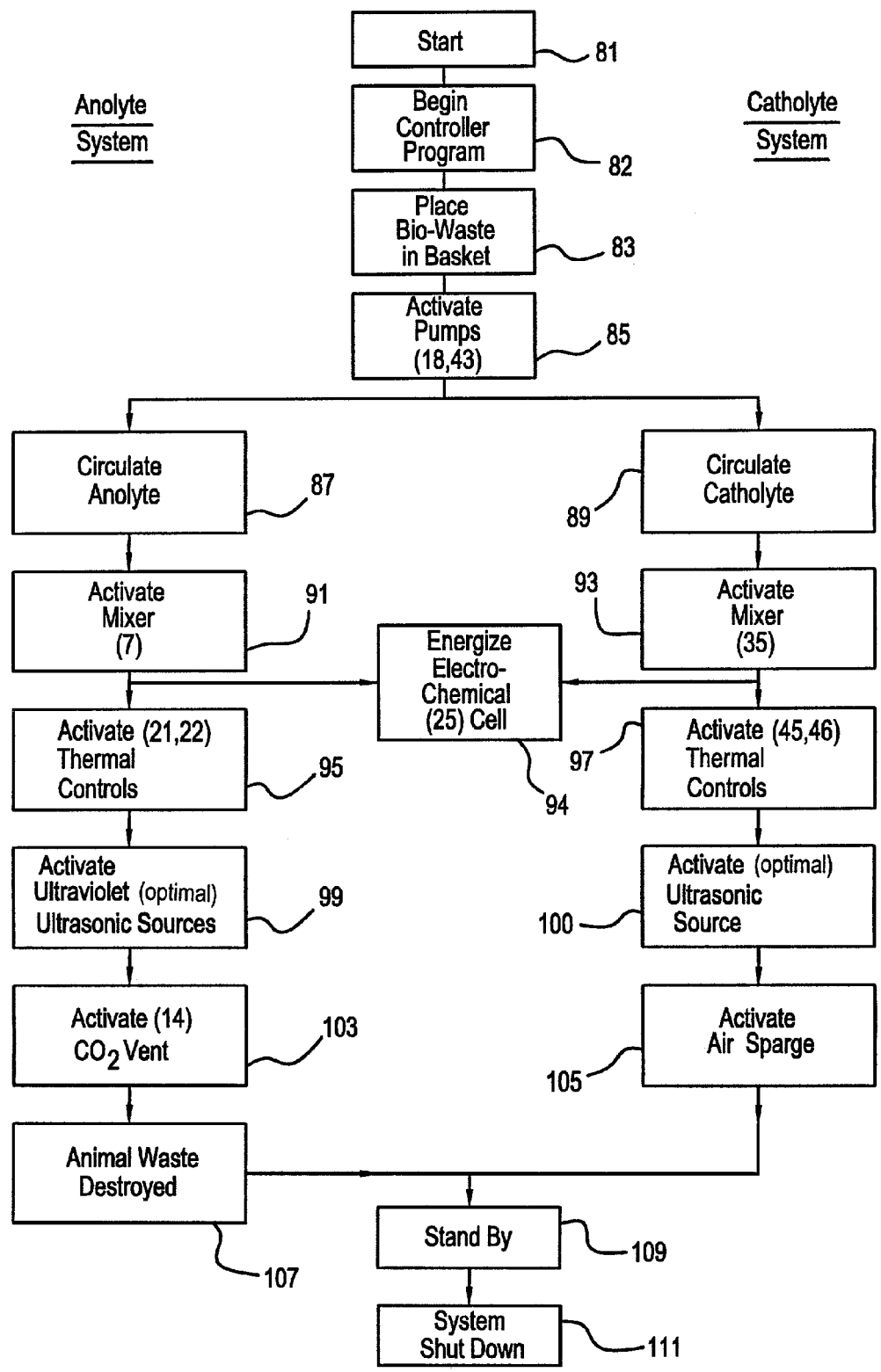

MEDIATED ELECTROCHEMICAL OXIDATION OF ANIMAL WASTE MATERIALS

This application claims the benefit of U.S. Provisional Application No. 60/327,005, filed Oct. 5, 2001.

FIELD OF THE INVENTION

This invention relates generally to a process and apparatus for the mediated electrochemical oxidation (MEO) destruction of animal waste which includes, but is not limited to, manure; carcasses; body parts; milk; bedding (hay and straw, e.g., dried grasses, clovers, legumes, and similar materials or stalks or stems of various grains, such as barley, oats, rice, rye, and wheat); biological residue; animal byproducts (hides, skins, hair, wool, feathers, glue stock (fleshing, hide cuttings and parings, tendons, or other collagenous parts of animal carcasses), bones, trimmings, meat scraps, hoofs, horns, bone meal (ground animal bones), hoof meal, horn meal, blood meal (dried blood of animals), meat meal or tankage (the rendered and dried carcasses or parts of the carcasses of animals), glands, organs, other parts or products unsuitable for consumption; biological items (preparations made from living organisms and their products, including vaccines, cultures, etc.; blood products; body fluids; chemotherapeutic waste (waste material resulting from the production or use of antineoplastic agents used for the purpose of stopping or reversing the growth of malignant cells); biological products; diagnostic specimens; therapeutic serums; etiologic, bacterial, fungal, viral and rickettsiae agents; toxins; antitoxins; human, animal and plant pathogens; recombinant organisms/molecules; genetically modified microorganisms; zoonoses; and protozoa; isolation waste (includes biological waste and discarded materials contaminated with blood, excretions, exudates, or isolated animals known to be infected with highly communicable diseases); and pathological waste (waste material consisting of only animal remains, anatomical parts, and/or tissue, the bags/containers used to collect and transport the waste material, and animal bedding); and, combined waste (e.g. a mixture of any of the foregoing with each other or other non-animal waste) hence fourth collectively referred to as animal waste.

For the purpose of this patent, animals include, but are not limited to, poultry (any kind of domesticated bird, including but not limited to chickens, doves, ducks, geese, grouse, guinea fowl, partridges, pea fowl, pheasants, pigeons, quail, swans, turkeys, egg shells, and eggs for hatching, or eating), cattle, bison, captive cervids, other hoofed animals (such as, llamas, alpacas, and antelope), sheep, goats, other ruminants, swine horses, assess, mules, zebras, dogs, cats, non-human primates (including prosimians, monkeys and apes), hamsters, rabbits, mink, chinchilla, mammals, reptiles, amphibians, mollusks, arthropods, birds (e.g. crows, pigeons, etc.), bats, fish and shell fish.

The following documents are added to the definition so as to further clarify the scope and definition of animal waste as any waste that is considered by any of, but not limited to, the following statutes and regulations:

9 C.F.R. ANIMAL AND ANIMAL PRODUCTS; Chapter I—ANIMAL AND PLANT HEALTH INSPECTION SERVICE, DEPARTMENT OF AGRICULTURE; Part 1—DEFINITION OF TERMS.

9 C.F.R. ANIMAL AND ANIMAL PRODUCTS; Part 145—NATIONAL POULTRY IMPROVEMENT PLAN; Subpart A—GENERAL PROVISIONS; Sec. 145.1 DEFINITIONS.

7 C.F.R. AGRICULTURE; Chapter I—AGRICULTURAL MARKETING SERVICE; Part 70—VOLUNTARY GRADING OF POULTRY PRODUCTS AND RABBIT PRODUCTS; Sec. 70.1 DEFINITIONS.

7 C.F.R. AGRICULTURE; Chapter VI—NATURAL RESOURCES CONSERVATION SERVICE, DEPARTMENT OF AGRICULTURE; Part 636-WILDLIFE HABITAT INCENTIVES PROGRAM; Sec. 636.3—DEFINITIONS.

7 C.F.R. AGRICULTURE; Chapter I—AGRICULTURAL MARKETING SERVICE; Part 94—POULTRY AND EGG PRODUCTS; Subpart D—PROCESSES POULTRY PRODUCTS; Sec. 94.301—DEFINITIONS.

7 C.F.R. AGRICULTURE; Chapter X—AGRICULTURAL MARKETING SERVICE (Marketing Agreements and Orders; Milk) DEPARTMENT OF AGRICULTURE; Subpart B—Definitions.

9 C.F.R. ANIMAL AND ANIMAL PRODUCTS; Part 3—STANDARDS; Subpart A—SPECIFICATIONS FOR THE HUMANE HANDLING, CARE, TREATMENT, AND TRANSPORTATION OF DOGS AND CATS.

9 C.F.R. ANIMAL AND ANIMAL PRODUCTS; Part 3—STANDARDS; Subpart B—SPECIFICATIONS FOR THE HUMANE HANDLING, CARE, TREATMENT, AND TRANSPORTATION OF GUINEA PIGS AND HAMSTERS.

9 C.F.R. ANIMAL AND ANIMAL PRODUCTS; Part 3—STANDARDS; Subpart C—SPECIFICATION FOR THE HUMANE HANDLING, CARE, TREATMENT, AND TRANSPORTATION OF RABBITS.

9 C.F.R. ANIMAL AND ANIMAL PRODUCTS; Part 3—STANDARDS; Subpart D—SPECIFICATIONS FOR THE HUMANE HANDLING, CARE, TREATMENT, AND TRANSPORTATION OF NONHUMAN PRIMATES.

9 C.F.R. ANIMAL AND ANIMAL PRODUCTS; Part 3—STANDARDS; Subpart E—SPECIFICATIONS FOR THE HUMANE HANDLING, CARE, TREATMENT, AND TRANSPORTATION OF MARINE MAMMALS.

9 C.F.R. ANIMAL AND ANIMAL PRODUCTS; Chapter I—ANIMAL AND PLANT HEALTH INSPECTION SERVICE, DEPARTMENT OF AGRICULTURE; Part 50—ANIMALS DESTROYED BECAUSE OF TUBERCULOSIS.

9 C.F.R. ANIMAL AND ANIMAL PRODUCTS; Part 93—IMPORTATION OF CERTAIN ANIMALS, BIRDS, AND POULTRY, AND CERTAIN ANIMALS.

9 C.F.R. ANIMAL AND ANIMAL PRODUCTS; Chapter III—FOOD SAFETY AND INSPECTION SERVICE, DEPARTMENT OF AGRICULTURE; Part 381—POULTRY PRODUCTS INSPECTION REGULATIONS.

40 C.F.R. PROTECTION OF ENVIRONMENT; Chapter I—ENVIRONMENTAL PROTECTION AGENCY; Part 432—MEAT PRODUCTS POINT SOURCE CATEGORY.

50 C.F.R. WILDLIFE AND FISHERIES; Chapter I—UNITED STATES FISH AND WILDLIFE SERVICE, DEPARTMENT OF THE INTERNATIONAL; Part 23—ENDANGERED SPECIES CONVENTION; Subpart C—APPENDICES I, II, AND III TO THE CONVENTION OF INTERNATIONAL TRADE IN ENDANGERED SPECIES OF WILD FAUNA AND FLORA; Sec. 23.23 SPECIES LISTED IN APPENDICES I, II, AND III 15 C.F.R. COMMERCE AND FOREIGN TRADE; PART 742—CONTROL POLICY—CCL BASED CONTROL; SECTION 742.2—PROLIFERATION OF CHEMICAL AND BIOLOGICAL WEAPONS.

21 C.F.R. FOOD AND DRUGS; PART 600—BIOLOGICAL PRODUCTS: GENERAL; SECTION 600.3—DEFINITIONS.

42 C.F.R. PUBLIC HEALTH; PART 72—INTERSTATE SHIPMENT OF ETIOLOGIC AGENTS; SECTION 72.1—DEFINITIONS AND APPENDIX A TO PART 72—SELECT AGENTS.

Animal waste is a relatively new problem for today's technological society. The definition of this waste has been expanding in its coverage of materials that must be handled in a controlled manner. The foregoing list of State statutes and United States Federal Regulations are overlapping but are necessary to accurately define the materials since no single statute or regulation covers all the materials for which this invention applies.

BACKGROUND OF THE INVENTION

Animal waste is a growing problem for today's technological society. The animal waste generated by a large segment of our agricultural sector is an increasing burden on these companies as well as the whole country in general. The magnitude of this growing problem can be seen from the following annual amount of animal manure generated by confined animals (in 1990) which represent approximately half of the animals in these categories: (a) cattle 27 million tons, (b) poultry 14 million tons, and (c) swine 16 million tons.

Considerable researches in the fields of public health, safety and environmental protection have raised the level of concern relative to the impact of this waste on our society. This has lead to the definition of this waste being expanded in its coverage of materials that must be handled in a controlled manner.

The cost of disposing of animal waste in the U.S. is a multi-billion dollar per year industry. The capital cost of the equipment required is in the hundreds of millions of dollars. All businesses, industrial companies, and institutions that generate and handle this category of waste must provide safe, effective and inexpensive disposal of the waste. In recent years there has been increasing concern over the disposal of animal waste. The number of materials that need to be controlled has continued to increase. Furthermore, the handling, storing, and transporting of the waste have continued to increase in cost. The liability for the consequences of the disposal of this waste is a major concern for all parties involved. The liability of the users does not end with the transfer of control of these materials to disposal companies for future problems they may cause.

The dominant methodologies used today generally can be categorized as thermal decomposition, long-term storage, or landfills methods.

The most frequently used thermal destruction techniques are various forms of incineration. All of these techniques have the potential to produce volatile organics that have serious health and environmental consequences.

In the case of long-term storage, this method is viewed as delaying the solving of the problem and in fact actually increases the degree of the problem in the future. The dumping in landfills has considerable risk for the users of these materials. Many companies build "holding ponds" to store the animal waste for an extended period of time but these ponds are a potential serious threat to the public health and safety. If they develop leaks or overflow, the waste can enter the ground water posing a serious environmental problem. These "holding ponds" can also become a breeding area for materials and organisms that have serious health consequences. Therefore, the user community has an immediate need to develop and incorporate improved methods for the handling of all types and form of animal wastes.

The methodology of this patent provides for the immediate destruction of animal waste as close to the source as possible thus avoiding the risk of expanding the exposure time or area to these materials. The destruction technology in this patent converts the animal waste into benign natural components. Nearly all-animal waste solid, liquid, or combinations thereof are decomposed into carbon dioxide, water, and small amounts of inorganic salts.

SUMMARY OF THE INVENTION

The invention relates to a method and apparatus(s) for the mediated electrochemical oxidation (MEO) of nearly all animal solid or liquid wastes, and combined waste (e.g., a mixture of any of the foregoing with each other or other non-animal waste), henceforth collectively referred to as animal waste. The method and apparatus have particular application to, but is not limited to manure; carcasses; body parts; milk; bedding (hay and straw, e.g., dried grasses, clovers, legumes, and similar materials or stalks or stems of various grains, such as barley, oats, rice, rye, and wheat); biological residue; animal byproducts (hides, skins, hair, wool, feathers, glue stock (fleshing, hide cuttings and parings, tendons, or other collagenous parts of animal carcasses), bones, trimmings, meat scraps, hoofs, horns, bone meal (ground animal bones), hoof meal, horn meal, blood meal (dried blood of animals), meat meal or tankage (the rendered and dried carcasses or parts of the carcasses of animals), glands, organs, other parts or products unsuitable for consumption; biological items (preparations made from living organisms and their products, including vaccines, cultures, etc.; blood products; body fluids; chemotherapeutic waste (waste material resulting from the production or use of antineoplastic agents used for the purpose of stopping or reversing the growth of malignant cells); biological products; diagnostic specimens; therapeutic serums; etiologic, bacterial, fungal, viral and rickettsiae agents; toxins; antitoxins; human, animal and plant pathogens; recombinant organisms/molecules; genetically modified microorganisms; zoonoses; and protozoa; isolation waste (includes biological waste and discarded materials contaminated with blood, excretions, exudates, or isolated animals known to be infected with highly communicable diseases); and pathological waste (waste material consisting of only animal remains, anatomical parts, and/or tissue, the bags/containers used to collect and transport the waste material, and animal bedding); and, combined waste (e.g. a mixture of any of the foregoing with each other or other non-animal waste) hence fourth collectively referred to as animal waste. The method and apparatus in this patent has the flexibility to deal with all of the forms of the animal waste as identified.

The mediated electrochemical oxidation (MEO) process involves an electrolyte containing one or more redox couples, wherein the oxidized form of at least one redox couple is produced by anodic oxidation at the anode(s) of an electrochemical cell. The oxidized forms of any other redox couples present are produced either by similar anodic oxidation or reaction with the oxidized form of other redox couples present capable of affecting the required redox reaction. The anodic oxidation in the electrochemical cell is driven by an externally induced electrical potential induced between the anode(s) and cathode(s) of the cell. The oxidized species of the redox couples oxidize the animal waste molecules and are themselves converted to their reduced form, whereupon they are reoxidized by either of the aforementioned mechanisms and the redox cycle continues until all oxidizable waste species, including intermediate reaction products, have undergone the desired degree of oxidation. The redox species ions are thus seen to "mediate" the transfer of electrons from the waste molecules to the anode, (i.e., oxidation of the waste).

A membrane in the electrochemical cell separates the anolyte and catholyte, thereby preventing parasitic reduction of the oxidizing species at the cathode. The membrane is typically an ion-selective cation exchange membrane (e.g., Nafion, etc.) or a microporous polymer, ceramic, or sintered glass membrane. The preferred MEO process uses the mediator species described in Table I (simple anions redox couple mediators); the Type I isopolyanions (IPA) formed by Mo, W, V, Nb, and Ta, and mixtures thereof; the Type I heteropolyanions (HPA) formed by incorporation into the aforementioned isopolyanions of any of the elements listed in Table II (heteroatoms) either singly or in combinations there of; any type heteropolyanion containing at least one heteropolyatom (i.e. element) contained in both Table I and Table II; or combinations of mediator species from any or all of these generic groups.

Simple Anion Redox Couple Mediators

Table I shows the simple anion redox couple mediators used in the preferred MEO process wherein "species" defines the specific ions for each chemical element that have applicability to the MEO process as either the reduced (e.g., $Fe^{+3}$) or oxidizer (e.g., $FeO_4^{-2}$) form of the mediator characteristic element (e.g., Fe), and the "specific redox couple" defines the specific associations of the reduced and oxidized forms of these species (e.g. $Fe^{+2}/FeO_4^{-2}$) that are claimed for the MEO process. Species soluble in the anolyte are shown in Table I in normal print while those that are insoluble are shown in bold underlined print. The characteristics of the MEO Process claimed in this patent are specified in the following paragraphs.

The anolyte in the MEO process contains one or more redox couples which in their oxidized form consist of either single multivalent element anions (e.g., $Ag^{+2}$, $Ce^{+4}$, $Co^{+3}$, $Pb^{+4}$, etc.), insoluble oxides of multivalent elements (e.g., $PbO_2$, $CeO_2$, $PrO_2$, etc.), or simple oxoanions (also called oxyanions) of multivalent elements (e.g., $FeO_4^{-2}$, $NiO_4^{-2}$, $BiO_3^{-}$, etc.). The redox couples in their oxidized form are called the mediator species. The nonoxygen multivalent element component of the mediator is called the characteristic element of the mediator species. We have chosen to group the simple oxoanions with the simple anion redox couple mediators rather than with the complex (i.e., polyoxometallate (POM)) anion redox couple mediators discussed in the next section and refer to them collectively as simple anion redox couple mediators.

In one embodiment of this process both the oxidized and reduced forms of the redox couple are soluble in the anolyte. The reduced form of the couple is anodically oxidized to the oxidized form at the cell anode(s) whereupon it oxidizes molecules of waste either dissolved in or located on waste particle surfaces wetted by the anolyte, with the concomitant reduction of the oxidizing agent to its reduced form, whereupon the MEO process begins again with the reoxidation of this species at the cell anode(s). If other less powerful redox couples of this type (i.e., reduced and oxidized forms soluble in anolyte) are present, they too may undergo direct anodic oxidation or the anodically oxidized more powerful oxidizing agent may oxidize them rather than a waste molecule. The weaker redox couple(s) is selected such that their oxidation potential is sufficient to affect the desired reaction with the waste molecules. The oxidized species of all the redox couples oxidize the animal waste molecules and are themselves converted to their reduced form, whereupon they are reoxidized by either of the aforementioned mechanisms and the redox cycle continues until all oxidizable waste species, including intermediate reaction products, have undergone the desired degree of oxidation.

The preferred mode for the MEO process as described in the preceding section is for the redox couple species to be soluble in the anolyte in both the oxidized and reduced forms, however this is not the only mode of operation claimed herein. If the reduced form of the redox couple is soluble in the anolyte (e.g., $Pb^{+2}$) but the oxidized form is not (e.g., $PbO_2$), the following processes are operative. The insoluble oxidizing agent is produced either as a surface layer on the anode by anodic oxidation, or throughout the bulk of the anolyte by reacting with the oxidized form of other redox couples present capable of affecting the required redox reaction, at least one of which is formed by anodic oxidation. The oxidizable waste is either soluble in the anolyte or dispersed therein at a fine particle size, (e.g., emulsion, colloid, etc.) thereby affecting intimate contact with the surface of the insoluble oxidizing agent (e.g., $PbO_2$) particles. Upon reaction of the waste with the oxidizing agent particles, the waste is oxidized and the insoluble oxidizing agent molecules on the anolyte wetted surfaces of the oxidizing agent particles reacting with the waste are reduced to their soluble form and are returned to the bulk anolyte, available for continuing the MEO process by being reoxidized.

In another variant of the MEO process, if the reduced form of the redox couple is insoluble in the anolyte (e.g., $TiO_2$) but the oxidized form is soluble (e.g., $TiO_2^{+2}$), the following processes are operative. The soluble (i.e., oxidized) form of the redox couple is produced by the reaction of the insoluble (i.e., reduced form) redox couple molecules on the anolyte wetted surfaces of the oxidizing agent particles with the soluble oxidized form of other redox couples present capable of affecting the required redox reaction, at least one of which is formed by anodic oxidation and soluble in the anolyte in both the reduced and oxidized forms. The soluble oxidized species so formed are released into the anolyte whereupon they oxidize waste molecules in the manner previously described and are themselves converted to the insoluble form of the redox couple, thereupon returning to the starting point of the redox MEO cycle.

In this invention, when an alkaline anolyte is used, the $CO_2$ resulting from oxidation of the animal waste reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the waste oxidation products that itself is capable of destroying additional animal waste.

The electrolytes used in this claim are from a family of acids, alkali, and neutral salt aqueous solutions (e.g. sulfuric acid, potassium hydroxide, sodium sulfate aqueous solutions, etc.).

A given redox couple or mixture of redox couples (i.e. mediator species) are to be used with different electrolytes.

The electrolyte composition is selected based on demonstrated adequate solubility of the compound containing at least one of the mediator species present in the reduced form (e.g., sulfuric acid may be used with ferric sulfate, etc.).

The concentration of the mediator species containing compounds in the anolyte may range from 0.0005 (M) up to the saturation point.

The concentration of electrolyte in the anolyte is governed by its effect upon the solubility of the mediator species containing compounds and by the conductivity of the anolyte solution desired in the electrochemical cell for the given mediator species being used.

The temperature over which the electrochemical cell may be operated ranges from approximately 0° C. too slightly below the boiling point of the electrolytic solution. The most frequently used thermal techniques, such as incineration, greatly exceed this temperature range. All of these techniques have the potential to produce volatile organics that have serious health and environmental consequences. Typical of these substances are dioxins and furans, which are controlled, waste materials. Dioxins and furans are formed in off gas streams of thermal treatment units (incinerators) when the off gases are cooled through the temperature range from 350° C. to approximately 250° C. The MEO process used in this patent does not create those conditions therefore does not produce these toxins.

The MEO process is operated at atmospheric pressure.

The mediator species are differentiated on the basis of whether they are capable of reacting with the electrolyte to produce free radicals (e.g., $O_2H$ (perhydroxyl), OH (hydroxyl), $SO_4$ (sulfate), $NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the electrodes in the electrochemical cell is based upon the oxidation potential of the most reactive redox couple present in the anolyte and serving as a mediator species, and the ohmic losses within the cell. Within the current density range of interest the electrical potential may be approximately 2.5 to 3.0 volts.

In the case of certain electrolyte compositions, a low level AC voltage is impressed across the electrodes in the electrochemical cell. The AC voltage is used to retard the formation of surface films on the electrodes that would have a performance limiting effect.

Complex Anion Redox Couple Mediators

The preferred characteristic of the oxidizing species in the MEO process is that it be soluble in the aqueous anolyte in both the oxidized and reduced states. The majority of metal oxides and oxoanion (oxyanion) salts are insoluble, or have poorly defined or limited solution chemistry. The early transition elements, however, are capable of spontaneously forming a class of discrete polymeric structures called polyoxometallate POMs (POMs) which are highly soluble in aqueous solutions over a wide pH range. The polymerization of simple tetrahedral oxoanions of interest herein involves an expansion of the metal, M, coordination number to 6, and the edge and corner linkage of $MO_6$ octahedra. Chromium is limited to a coordination number of 4, restricting the POMs based on $CrO_4$ tetrahedra to the dichromate ion $[Cr_2O_7]^{-2}$ which is included in Table I. Based upon their chemical composition POMs are divided into the two subclasses isopolyanions (IPAs) and heteropolyanions (HPAs), as shown by the following general formulas:

Isopolyanions(IPAs)—$[M_mO_y]^{p-}$ and,

Heteropolyanions(HPAs)—$[X_xM_mO_y]^{q-}(m>x)$ where the addenda atom, M, is usually Molybdenum (Mo) or Tungsten (W), and less frequently Vanadium (V), Niobium (Nb), or Tantalum (Ta), or mixtures of these elements in their highest ($d^0$) oxidation state. The elements that can function as addenda atoms in IPAs and HPAs appear to be limited to those with both a favorable combination of ionic radius and charge, and the ability to form dn-pn M—O bonds. However, the heteroatom, X, have no such limitations and can be any of the elements listed in Table II.

There is a vast chemistry of POMs that involves the oxidation/reduction of the addenda atoms and those heteroatoms listed in Table II, that exhibit multiple oxidation states. The partial reduction of the addenda, M, atoms in some POMs strictures (i.e., both IPAs and HPAs) produces intensely colored species, generically referred to as "heteropoly blues". Based on structural differences, POMs can be divided into two groups, Type I and Type II. Type I POMs consist of $MO_6$ octahedra each having one terminal oxo oxygen atom while Type II have 2 terminal oxo oxygen atoms. Type II POMs can only accommodate addenda atoms with $d^0$ electronic configurations, whereas Type I; e.g., Keggin ($XM_{12}O_{40}$), Dawson ($X_2M_{18}O_{62}$), hexametalate ($M_6O_{19}$), decatungstate ($W_{10}O_{32}$), etc., can accommodate addenda atoms with $d^0$, $d^1$, and $d^2$ electronic configurations. Therefore, while Type I structures can easily undergo reversible redox reactions, structural limitations preclude this ability in Type II structures. Oxidizing species applicable for the MEO process are therefore Type I POMs (i.e., IPAs and HPAs) where the addenda, M, atoms are W, Mo, V, Nb, Ta, or combinations there of.

The high negative charges of polyanions often stabilize heteroatoms in unusually high oxidation states, thereby creating a second category of MEO oxidizers in addition to the aforementioned Type I POMs. Any Type I or Type II HPA containing any of the heteroatom elements, X, listed in Table II, that also are listed in Table I as simple anion redox couple mediators, can also function as an oxidizing species in the MEO process.

The anolyte contains one or more complex anion redox couples, each consisting of either the afore mentioned Type I POMs containing W, Mo, V, Nb, Ta or combinations there of as the addenda atoms, or HPAs having as heteroatoms (X) any elements contained in both Tables I and II, and which are soluble in the electrolyte (e.g. sulfuric acid, etc.).

The electrolytes used in this claim are from a family of acids, alkali, and neutral salt aqueous solutions (e.g. sulfuric acid, potassium hydroxide, sodium sulfate aqueous solutions, etc.).

A given POM redox couple or mixture of POM redox couples (i.e., mediator species) may be used with different electrolytes.

The electrolyte composition is selected based on demonstrating adequate solubility of at least one of the compounds containing the POM mediator species in the reduced form and being part of a redox couple of sufficient oxidation potential to affect oxidation of the other mediator species present.

The concentration of the POM mediator species containing compounds in the anolyte may range from 0.0005M (molar) up to the saturation point.

The concentration of electrolyte in the anolyte may be governed by its effect upon the solubility of the POM mediator species containing compounds and by the conductivity of the anolyte solution desired in the electrochemical cell for the given POM mediator species being used to allow the desired cell current at the desired cell voltage.

The temperature over which the electrochemical cell may be operated ranges from approximately 0° C. to just below the boiling point of the electrolytic solution.

The MEO process is operated at atmospheric pressure.

The POM mediator species are differentiated on the basis of whether they are capable of reacting with the electrolyte to produce free radicals (e.g., $O_2H$, OH, $SO_4$, and $NO_3$). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the anode(s) and cathode(s) in the electrochemical cell is based on the oxidation potential of the most reactive POM redox couple present in the anolyte and serving as a mediator species, and the ohmic losses within the cell. Within the current density range of interest the electrical potential may be approximately 2.5 to 3.0 volts.

Mixed Simple and Complex Anion Redox Couple Mediators

The preferred MEO process for a combination of simple anion redox couple mediators (A) and complex anion redox couple mediators (B) may be mixed together to form the system anolyte. The characteristics of the resulting MEO process is similar to the previous discussions.

The use of multiple oxidizer species in the MEO process has the following potential advantages:

The overall waste destruction rate is increased if the reaction kinetics of anodically oxidizing mediator "A", oxidizing mediator "B" and oxidized mediator "B" oxidizing the animal waste is sufficiently rapid such that the combined speed of the three step reaction train is faster than the two step reaction trains of anodically oxidizing mediator "A" or "B", and the oxidized mediators "A" or "B" oxidizing the animal waste.

If the cost of mediator "B" is sufficiently less than that of mediator "A", the used of the above three step reaction train results in lowering the cost of waste destruction due to the reduced cost associated with the smaller required inventory and process losses of the more expensive mediator "A". An example of this is the use of a silver (II)-peroxysulfate mediator system to reduce the cost associated with a silver (I/II) only MEO process and overcome the slow anodic oxidation kinetics of a sulfate/peroxysulfate only MEO process.

The MEO process is "desensitized" to changes in the types of molecular bonds present in the animal waste as the use of multiple mediators, each selectively attacking different types of chemical bonds, results in a highly "nonselective" oxidizing system.

Anolyte Additional Features

In one preferred embodiment of the MEO process in this invention, there are one or more simple anion redox couple mediators in the anolyte aqueous solution. In another preferred embodiment of the MEO process, there are one or more complex anion (i.e., POMs) redox couple mediators in the anolyte aqueous solution. In another preferred embodiment of the MEO process, there are one or more simple anion redox couples and one or more complex anion redox couples in the anolyte aqueous solution.

The MEO process of the present invention uses any oxidizer species listed in Table I that are found in situ in the waste to be destroyed. For example, when the animal waste also contains iron (Fe) compounds that become a source of $FeO_4^{-2}$ ions under the MEO process conditions within the anolyte, the waste-anolyte mixture may be circulated through an electrochemical cell, where the oxidized form of the reversible iron redox couple is formed either by anodic oxidation within the electrochemical cell or alternately by reacting with the oxidized form of a more powerful redox couple, if present in the anolyte and the latter being anodically oxidized in the electrochemical cell. The iron thus functions exactly as a simple anion redox couple species thereby destroying the organic waste component leaving only the iron to be disposed of. Adding one or more of any of the anion redox couple mediators described in this patent further enhances the MEO process described above.

In the MEO process of the invention, anion redox couple mediators in the anolyte part of an aqueous electrolyte solution uses an acid, neutral or alkaline solution depending on the temperature and solubility of the specific mediator(s). The anion oxidizers used in the basic MEO process preferably attack specific organic molecules. Hydroxyl free radicals preferentially attack organic molecules containing aromatic rings and unsaturated carbon-carbon bonds. Oxidation products such as the highly undesirable aromatic compounds chlorophenol or tetrachlorodibenzodioxin (dioxin) upon formation would thus be preferentially attacked by hydroxyl free radicals, preventing the accumulation of any meaningful amounts of these compounds. Even free radicals with lower oxidation potentials than the hydroxyl free radical preferentially attack carbon-halogen bonds such as those in carbon tetrachloride and polychlorobiphenyls (PCBs).

Some redox couples having an oxidation potential at least equal to that of the $Ce^{+3}/Ce^{+4}$ redox couple (i.e., 1.7 volts at 1 molar, 25° C. and pH 1), and sometimes requiring heating to above about 50° C. (i.e., but less then the boiling point of the electrolyte) can initiate a second oxidation process wherein the mediator ions in their oxidized form interact with the aqueous anolyte, creating secondary oxidizer free radicals (e.g., $O_2H$, OH, $SO_4$, $NO_3$, etc.) or hydrogen peroxide. Such mediator species in this invention are classified herein as "super oxidizers" (SO) to distinguish them from the "basic oxidizers" incapable of initiating this second oxidation process.

The oxidizer species addressed in this patent (i.e., characteristic elements having atomic number below 90) are described in Table I (simple anions redox couple mediators): Type I IPAs formed by Mo, W, V, Nb, Ta, or mixtures there of as addenda atoms; Type I HPAs formed by incorporation into the aforementioned IPAs if any of the elements listed in Table II (heteroatoms) either singly or in combinations thereof; or any HPA containing at least one heteroatom type (i.e., element) contained in both Table I and Table II; or mediator species from any or all of these generic groups.

Each oxidizer anion element has normal valence states (NVS) (i.e., reduced form of redox couple) and higher valence states (HVS) (i.e., oxidized form of redox couple) created by stripping electrons off NVS species when they pass through an electrochemical cell. The MEO process of the present invention uses a broad spectrum of anion oxidizers; these anion oxidizers used in the basic MEO process may be interchanged in the preferred embodiment without changing the equipment.

In preferred embodiments of the MEO process, the basic MEO process is modified by the introduction of additives as stabilizing compounds such as tellurate or periodate ions which serve to overcome the short lifetime of the oxidized form of some redox couples (e.g., $Cu^{+3}$) in the anolyte via the formation of more stable complexes (e.g., $[Cu(IO_6)_2]^{-7}$, $[Cu(HTeO_6)_2]^{-7}$). The tellurate and periodate ions can also participate directly in the MEO process as they are the oxidized forms of simple anion redox couple mediators (see Table I) and participate in the oxidation of animal waste in the same manner as previously described for this class of oxidizing agents.

Alkaline Electrolytes

In one preferred embodiment, a cost reduction is achieved in the basic MEO process by using an alkaline electrolyte, such as but not limited to aqueous solutions of NaOH or KOH with mediator species wherein the reduced form of said mediator redox couple displays sufficient solubility in said electrolyte to allow the desired oxidation of the animal waste to proceed at a practical rate. The oxidation potential of redox reactions producing hydrogen ions (i.e., both mediator species and animal waste molecules reactions) are inversely proportional to the electrolyte pH, thus with the proper selection of a redox couple mediator, it is possible, by increasing the electrolyte pH, to minimize the electric potential required to affect the desired oxidation process, thereby reducing the electric power consumed per unit mass of animal waste destroyed.

When an alkaline anolyte (e.g., NaOH, KOH, etc.) is used, benefits are derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution.

In this invention, when an alkaline anolyte is used, the $CO_2$ resulting from oxidation of the animal waste reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the waste oxidation products that itself is capable of destroying additional animal waste.

Additional MEO Electrolyte Features

In one preferred embodiment of this invention, the catholyte and anolyte are discrete entities separated by a membrane, thus they are not constrained to share any common properties such as electrolyte concentration, composition, or pH (i.e., acid, alkali, or neutral). The process operates over the temperature range from approximately 0° C. too slightly below the boiling point of the electrolyte used during the destruction of the animal waste.

MEO Process Augmented by Ultraviolet/Ultrasonic Energy

Decomposition of the hydrogen peroxide into free hydroxyl radicals is well known to be promoted by ultraviolet (UV) irradiation. The destruction rate of animal waste obtained using the MEO process in this invention, therefore, be increased by UV irradiation of the reaction chamber anolyte to promote formation of additional hydroxyl free radicals. In a preferred embodiment, UV radiation is introduced into the anolyte chamber using a UV source either internal to or adjacent to the anolyte chamber. The UV irradiation decomposes hydrogen peroxide, which is produced by secondary oxidizers generated by the oxidized form of the mediator redox couple, into hydroxyl free radical. The result is an increase in the efficiency of the MEO process since the energy expended in hydrogen peroxide generation is recovered through the oxidation of animal materials in the anolyte chamber.

Additionally, in a preferred embodiment, ultrasonic energy may be applied into the anolyte chamber to rupture the cell membranes of biological materials. The ultrasonic energy is absorbed in the cell wall and the local temperature is raised to above several thousand degrees, resulting in cell wall failure. This substantially increases the effectiveness of oxidation by the oxidation form of redox couple species present as well as the overall efficiency of the MEO process.

Additionally, ultrasonic energy is introduced into the anolyte chamber. Implosion of the microscopic bubbles formed by the rapidly oscillating pressure waves emanating from the sonic horn generate shock waves capable of producing extremely short lived and localized conditions of 4800° C. and 1000 atmospheres pressure within the anolyte. Under these conditions water molecules decompose into hydrogen atoms and hydroxyl radicals. Upon quenching of the localized thermal spike, the hydroxyl radicals undergo the aforementioned reactions with the animal waste or combine with each other to form another hydrogen peroxide molecule which then itself oxidizes additional animal waste.

In another preferred embodiment, the destruction rate of non anolyte soluble animal waste is enhanced by affecting a reduction in the dimensions of the individual second (i.e., animal waste) phase entities present in the anolyte, thereby increasing the total waste surface area wetted by the anolyte and therefore the amount of waste oxidized per unit time. Immsicible liquids may be dispersed on an extremely fine scale within the aqueous anolyte by the introduction of suitable surfactants or emulsifying agents. Vigorous mechanical mixing such as with a colloid mill or the microscopic scale mixing affected by the aforementioned ultrasonic energy induced microscopic bubble implosion could also be used to affect the desired reduction in size of the individual second phase waste volumes dispersed in the anolyte. The vast majority of solid waste may be converted into a liquid phase, thus becoming treatable as above, using a variety of cell disruption methodologies. Examples of these methods are mechanical shearing using various rotor-stator homogenizers and ultrasonic devices (i.e., sonicators) where the aforementioned implosion generated shock wave, augmented by the 4800° C. temperature spike, shear the cell walls. Distributing the cell protoplasm throughout the anolyte produces an immediate reduction in the mass and volume of actual wastes as about 67 percent of protoplasm is ordinary water, which simply becomes part of the aqueous anolyte, requiring no further treatment.

If the amount of water released directly from the animal waste and/or formed as a reaction product from the oxidation of hydrogenous waste dilutes the anolyte to an unacceptable level, the anolyte can easily be reconstituted by simply raising the temperature and/or lowering the pressure in an optional evaporation chamber to affect removal of the required amount of water. The soluble constituents of the animal waste are rapidly dispersed throughout the anolyte on a molecular scale while the insoluble constituents are dispersed throughout the anolyte as an extremely fine second phase using any of the aforementioned dispersal methodologies, thereby vastly increasing the waste anolyte interfacial contact area beyond that possible with an intact solid configuration and thus the rate at which the animal waste is destroyed and the MEO efficiency.

In another preferred embodiment, increasing the surface area exposed to the anolyte enhances the destruction rate of non-anolyte solid organic waste. The destruction rate for any given concentration of oxidizer in solution in the anolyte is limited to the area of the solid with which the oxidizer can make contact. The embodiment used for solids contains a mechanism for multiply puncturing the solid when it is placed in the anolyte reaction chamber basket. The punctures allow the oxidizer to penetrate into the interior of the solid by-passing difficult to destroy surface layers (e.g., skin, membranes. etc.) and increase the rate of destruction.

MEO Process Augmented with Free Radicals

The principals of the oxidation process used in this invention in which a free radical (e.g., $O_2H$, $OH$, $SO_4$, $NO_3$,) cleaves and oxidize organic compounds resulting in the formation of successively smaller hydrocarbon compounds. The intermediate compounds so formed are easily oxidized to carbon dioxide and water during sequential reactions.

Inorganic radicals are be generated in aqueous solution variants of the MEO process in this invention. Inorganic free radicals have been derived from carbonate, azide, nitrite, nitrate, phosphate, phosphite, sulphite, sulphate, selenite, thiocyanate, chloride, bromide, iodide and formate ions. Organic free radicals, such as sulfhydryl, may be generated by the MEO process. When the MEO process in this invention is applied to organic materials they are broken down into organic compounds that are attacked by the aforementioned inorganic free radicals, producing organic free radicals, which contribute to the oxidation process and increase the efficiency of the MEO process.

Animal waste materials are introduced into an apparatus for contacting the waste with an electrolyte containing the oxidized form of one or more reversible redox couples, at least one of which is produced electrochemically by anodic oxidation at the anode of an electrochemical cell. The oxidized forms of any other redox couples present are produced either by similar anodic oxidation or reaction with the oxidized form of other redox couples present and capable of affecting the required redox reaction. The oxidized species of the redox couples oxidize the organic waste molecules and are themselves converted to their reduced form, whereupon they are reoxidized by either of the aforementioned mechanisms and the redox cycle continues until all oxidizable waste species, including intermediate reaction products, have undergone the desired degree of oxidation. The entire process takes place at temperatures between zero degrees centigrade and slightly below the boiling point of the electrolyte, thereby avoiding any possible formation of either dioxins or furans. The oxidation process may be enhanced by the addition of reaction enhancements, such as: ultrasonic energy and/or ultraviolet radiation.

These and further and other objects and features of the invention are apparent in the disclosure, which includes the above and ongoing written specification, with the characteristics and drawings.

BRIEF DESCRIPTION OF THE DRAWINGS

FIG. 1A is a representation of a general embodiment of the present invention (with the understanding that not all of the components shown therein must necessarily be employed in all situations and others may be added as needed for a particular application).

FIG. 2 is a representation of a general embodiment of a controller for the present invention shown in FIG. 3 (with the understanding that not all of the components shown therein must necessarily be employed in all situations and others may be added as needed for a particular application).

FIG. 4 MEO Model 5.$b$ Operational Steps is a schematic representation of the generalized steps of the process used in the MEO apparatus shown in FIG. 3 (with the understanding that not all of the components shown therein must necessarily be employed in all situations and others may be added as needed for a particular application).

DETAILED DESCRIPTION OF PREFERRED EMBODIMENTS

MEO Chemistry

Mediated Electrochemical Oxidation (MEO) process chemistry described in this patent uses oxidizer species (i.e., characteristic elements having atomic number below 90) as described in Table I (simple anions redox couple mediators); Type I IPAs formed by Mo, W, V, Nb, Ta, or mixtures there of as addenda atoms; Type I HPAs formed by incorporation into the aforementioned IPAs of any of the elements listed in Table II (heteroatoms) either singly or in combination thereof; or any HPA containing at least one heteroatom type (i.e., element) contained in both Table I and Table II; or combinations of mediator species from any or all of these generic groups. Since the anolyte and catholyte are completely separated entities, it is not necessary for both systems to contain the same electrolyte. Each electrolyte may, independent of the other, consist of an aqueous solution of acids, typically but not limited to nitric, sulfuric, of phosphoric; alkali, typically but not limited to sodium or potassium hydroxide; or neutral salt typically but not limited to sodium or potassium salts of the aforementioned strong mineral acids.

The MEO Apparatus is unique in that it accommodates the numerous choices of mediator ions and electrolytes by simply draining, flushing, and refilling the system with the mediator/electrolyte system of choice.

Because of redundancy and similarity in the description of the various mediator ions, only the iron and nitric acid combination is discussed in detail. However, it is to be understood that the following discussion of the ferric/ferrate, $(Fe^{+3})/(FeO_4^{-2})$ redox couple reaction in nitric acid ($HNO_3$) also applies to all the aforementioned oxidizer species and electrolytes described at the beginning of this section. Furthermore, the following discussions of the interaction of ferrate ions with aqueous electrolytes to produce the aforementioned free radicals also applies to all aforementioned mediators having an oxidation potential sufficient to be classified superoxidizers (SO). An SO has an oxidation potential at least equal to that of the redox couple $Ce^{+3}/Ce^{+4}$ which has a potential of approximately 1.7 volts at 1 molar, 25° C. and pH 1 in an acid electrolyte.

Figure 1A:
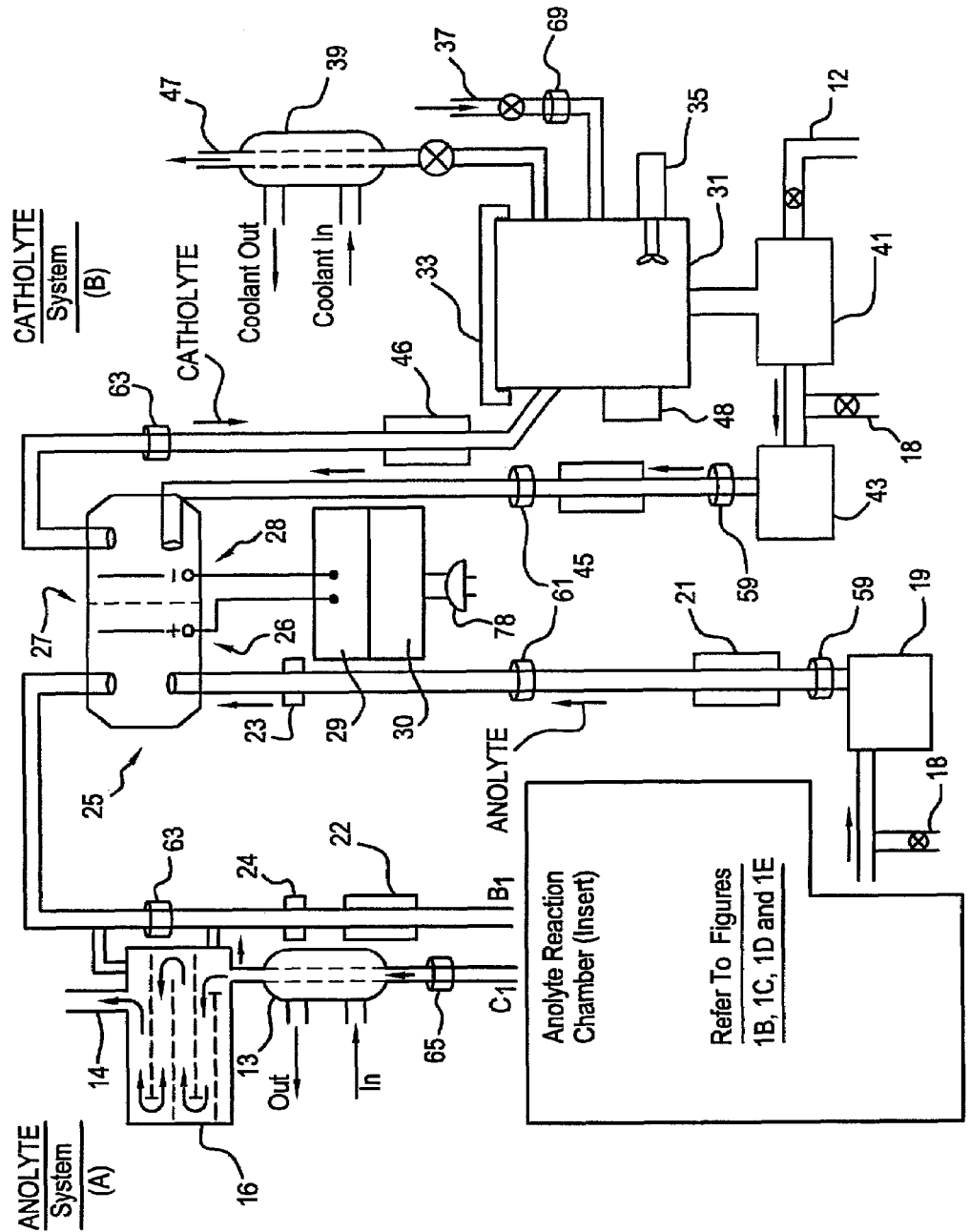
FIG. 1A MEO Apparatus Diagram is a schematic representation of a system for destroying animal waste materials.

FIG. 1A shows a MEO Apparatus in a schematic representation for destroying animal waste. At the anode of the electrochemical cell 25 Fe(III) ions ($Fe^{+3}$, ferric) are oxidized to Fe(VI) ions ($FeO_4^{-2}$, ferrate), $$Fe^{+3} + 4H_2O \rightarrow FeO_4^{-2} + 8H^+ + 3e^-$$

If the anolyte temperature is sufficiently high, typically above 50° C., the Fe(VI) species may undergo a redox reaction with the water in the aqueous anolyte. The oxidation of water proceeds by a sequence of reactions producing a variety of intermediate reaction products, some of which react with each other. A few of these intermediate reaction products are highly reactive free radicals including, but not limited to the hydroxyl ($\circ OH$) and hydrogen peroxy or perhydroxyl ($\circ HO_2$) radicals. Additionally, the mediated oxidizer species ions may interact with anions present in the acid or neutral salt electrolyte (e.g., $NO_3^-$, $SO_4^{-2}$, or $PO_4^{-3}$, etc.) to produce free radicals typified by, but not limited to $\circ NO_3$, or the anions may undergo direct oxidation at the anode(s) of the cell. The population of hydroxyl free radicals may be increased by ultraviolet irradiation of the anolyte (see ultraviolet source 11) in the reaction chambers 5(a,b,c) and buffer tank 20 to cleave the hydrogen peroxide molecules, and intermediate reaction products, into two such radicals. Free radical populations also be increased by ultrasonic vibration (see ultrasonic source 9) induced by the aforementioned implosion generated shock wave, augmented by the 4800° C. temperature spike and 1000 atmospheres pressure.

These secondary oxidation species are capable of oxidizing organic materials and thus act in consort with Fe(VI) ions to oxidize the organic materials.

The oxidizers react with the animal waste to produce $CO_2$ and water. These processes occur in the anolyte on the anode side of the system in the reaction chambers 5(a,b,c,d), buffer tank 20, and throughout the anolyte system when in solution.

Addition of ferric ions to non-iron-based MEO systems has the potential for increasing the overall rate of animal waste oxidation compared to the non-iron MEO system alone. (Again it is to be understood this discussion of the ferric/ferrate redox couple also applies to all the aforementioned oxidizer species described at the beginning of this section.) An example is consider a two step process the first of which is to electrochemically form an $FeO_4^{-2}$ ion. In the second step is the $FeO_4^{-2}$ ion oxidizes a mediator ion, from its reduced form (e.g., sulfate) to its oxidized form (e.g., peroxysulfate), faster than by the direct anodic oxidation of the sulfate ion itself. Thus there is an overall increase in the rate of animal waste destruction.

Membrane 27 separates the anode and the cathode chambers in the electrochemical cell 25. Hydrogen ions ($H^+$) or hydronium ions ($H_3O^+$) travel through the membrane 27 due to the electrical potential from the dc power supply 29 applied between the anode(s) 26 and cathodes(s) 28. In the catholyte the nitric acid is reduced to nitrous acid $$3HNO_3 + 6H^+ + 6e^- \rightarrow 3HNO_2 + H_2O$$

by the reaction between the $H^+$ ions and the nitric acid. Oxygen is introduced into the catholyte through the air sparge 37 located below the liquid surface, and the nitric acid is regenerated, $$3HNO_2 + 3/2O_2 \rightarrow 3HNO_3$$

In the case where the catholyte contain compounds other then nitrogen such as sulfuric or phosphoric acids or their salts, the hydrogen ions ($H^+$) or hydronium ions ($H_3O^+$) contact the cathode and hydrogen gas evolves. The hydrogen gas is diluted with the air from the air sparge and released to the atmosphere or the evolved hydrogen gas can be feed to devices that use hydrogen as a fuel such as the fuel cells. The hydrogen may under go purification prior to use (e.g., palladium diffusion, etc.) and/or solid state storage (e.g., adsorption in zirconium, etc.).

In some cases oxygen is evolved at the anode due to the over voltage necessary to create the oxidation species of some of the mediator ions. The efficiency of these mediators is somewhat less under those conditions. The evolved oxygen can be feed to the devices that use hydrogen as a fuel such as the fuel cells. Using the evolved oxygen to enrich the air above its nominal oxygen content of 20.9 percent increases the efficiency of fuel cells deriving their oxygen supply from ambient air.

The overall process results in the animal waste being converted to carbon dioxide, water, and a small amount of inorganic compounds in solution or as a precipitate, which may be extracted by the inorganic compound removal and treatment system 15.

The MEO process may proceed until complete destruction of the animal waste has been affected or modified to stop the process at a point where the destruction of the animal waste is incomplete but: a) the organic materials are benign and do not need further treatment, or b) the organic materials may be used in the form they have been reduced to and thus would be recovered for that purpose.

The entireties of U.S. Pat. Nos. 4,686,019; 4,749,519; 4,874,485; 4,925,643; 5,364,508; 5,516,972; 5,745,835; 5,756,874; 5,810,995; 5,855,763; 5,911,868; 5,919,350; 5,952,542; and 6,096,283 are included herein by reference for their relevant teachings.

MEO Apparatus

A schematic drawing of the MEO apparatus shown in FIG. 1A MEO Apparatus Diagram illustrates the application of the MEO process to the destruction of animal waste. The bulk of the anolyte resides in the anolyte reaction chambers 5(a,b,c) and the buffer tank 20. In the case where the animal waste is liquid only, the reaction chambers 5(a) is modified to have a continuous input device so that the liquid is pumped into the reaction chambers 5(a) without having to operate a hinged lid 1. The anolyte portion of the electrolyte solution contains for example $Fe^{+3}/FeO_4^{-2}$ redox couple anions and secondary oxidizing species (e.g., free radicals, $H_2O_2$, etc.).

The MEO apparatus is composed of two separate closed-loop systems containing an electrolyte solution composed of anolyte and catholyte solutions. The anolyte and catholyte solutions are contained in the anolyte (A) system and the catholyte (B) system, respectively. These two systems are discussed in detail in the following paragraphs.

Anolyte System (A)

Referring to FIG. 1A, the animal waste may be a liquid, solid, a mixture of solids and liquids, or combined waste. FIGS. 1B through 1E provide preferred embodiments of the anolyte reaction chambers 5(a), 5(b), 5(c), 5(d), and buffer tank 20.

Figure 1C:
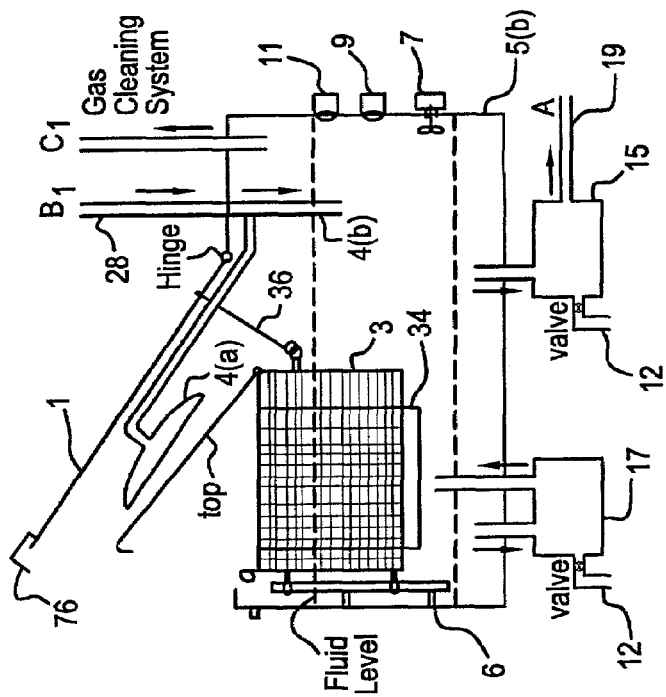
FIG. 1C Anolyte Reaction Chamber for Solids, Mixtures, and Larger Particulate and with Batch Operation is a schematic representation of the anolyte reaction chamber used for animal waste solids, and mixtures that include large particulate. This chamber may be used for batch mode processing of animal wastes.
Figure 1B:
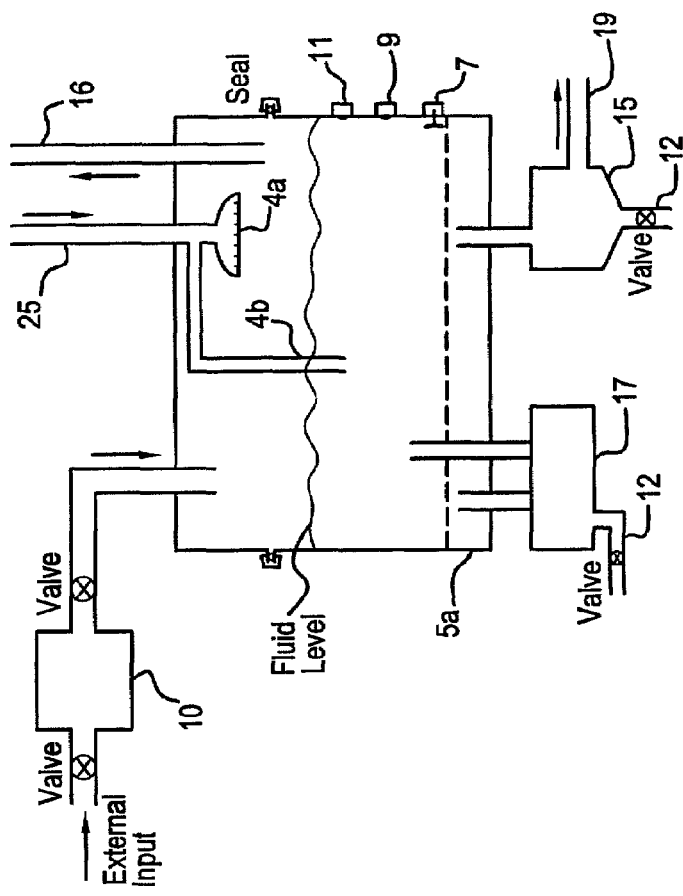
FIG. 1B Anolyte Reaction Chamber for Liquids, Mixtures, and Small Particulate and with Continuous Feed is a schematic representation of the anolyte reaction chamber used for animal waste fluids, and mixtures, which include small particulate. This chamber accommodates a continuous feed of these materials into the chamber.

The anolyte reaction chamber 5(a) in FIG. 1B is designed for liquids, small particulate and continuous feed operations. The animal waste is introduced into the anolyte reaction chamber 5(a) through the input pump 10 connected to the source of the animal waste to be destroyed. The animal waste is pumped into the chamber 5(a), which contains the anolyte used to destroy that animal waste. The apparatus continuously circulates the anolyte portion of the electrolyte directly from the electrochemical cell 25 through the reaction chamber 5(a) to maximize the concentration of oxidizing species contacting the waste. The anolyte is introduced into the anolyte reaction chamber 5(a) through the spray head 4(a) and stream head 4(b). The two heads are designed to increase the exposure of the animal waste to the anolyte by enhancing the mixing in the anolyte reaction chamber 5(a). Introducing the anolyte into the reaction chamber 5(a) as a spray onto the anolyte surface promotes contact with (i.e., oxidation of) any immiscible organic surface layers present. A filter 6 is located at the base of the reaction chamber 5(a) to limit the size of the solid particles to approximately 1 mm in diameter (i.e., smaller that the minimum dimension of the anolyte flow path in the electrochemical cell 25) thereby preventing solid particles large enough to clog the electrochemical cell 25 flow paths from exiting the reaction chamber 5(a). Contact of the oxidizing species with incomplete oxidation products that are gaseous at the conditions within the reaction chamber 5(a) may be further enhanced by using conventional techniques for promoting gas/liquid contact (e.g., ultrasonic vibration 9, mechanical mixing 7). An ultraviolet source 11 is introduced into the anolyte reaction chamber 5(a) to decompose the hydrogen peroxide formed by the MEO process into free hydroxyl radicals.

The anolyte reaction chamber 5(b) in FIG. 1C is designed for solids, mixtures and batch operations. The hinged lid 1 is lifted, and the top of the basket 3 is opened. The solid animal waste is introduced into the basket 3 in the reaction chamber 5(b) where the solid waste remains while the liquid portion of the waste flows into the anolyte. The basket 3 top is closed and the basket 3 is lowered by a lever 36 connected to the lid 1 into the anolyte such that all its contents are held submerged in the anolyte throughout the oxidization process. Lid 1 has a seal around the opening and it is locked before operation begins.

A mechanical device (penetrator 34) is incorporated into the basket 3 that create multiple perforations in the outer layers of the solid animal waste so that the anolyte can penetrate into the waste. This penetration speeds up the oxidation of the solid animal waste by increasing the surface area exposed to the anolyte oxidizer, and allowing said oxidizer immediate access to portions of the aforementioned waste that are encased in (i.e., protected by) more difficult to oxidize surrounding outer layers (e.g., hide, etc.).

The apparatus continuously circulates the anolyte portion of the electrolyte directly from the electrochemical cell 25 through the reaction chamber 5(b) to maximize the concentration of oxidizing species contacting the waste. The anolyte enter the reaction chamber 5(b) and is injected through two nozzles; one a spray head to distribute the anolyte throughout the reaction chamber 5(b), and the second is a stream head to promote circulation and turbulence in the anolyte in the chamber. Introducing the anolyte into the reaction chamber 5(b) as a spray onto the anolyte surface promotes contact with (i.e., oxidation of) any immiscible organic surface layers present. A filter 6 is located at the base of the reaction chamber 5(b) to limit the size of the solid particles to approximately 1 mm in diameter (i.e., smaller that the minimum dimension of the anolyte flow path in the electrochemical cell 25) thereby preventing solid particles large enough to clog the electrochemical cell 25 flow paths from exiting the reaction chamber 5(b). Contact of the oxidizing species with incomplete oxidation products that are gaseous at the conditions within the reaction chamber 5(b) may be further enhanced by using conventional techniques for promoting gas/liquid contact (e.g., ultrasonic vibration 9, mechanical mixing 7). An ultraviolet source 11 is introduced into the anolyte reaction chamber 5(b) to decompose the hydrogen peroxide formed by the MEO process into free hydroxyl radicals.

Figure 1D:
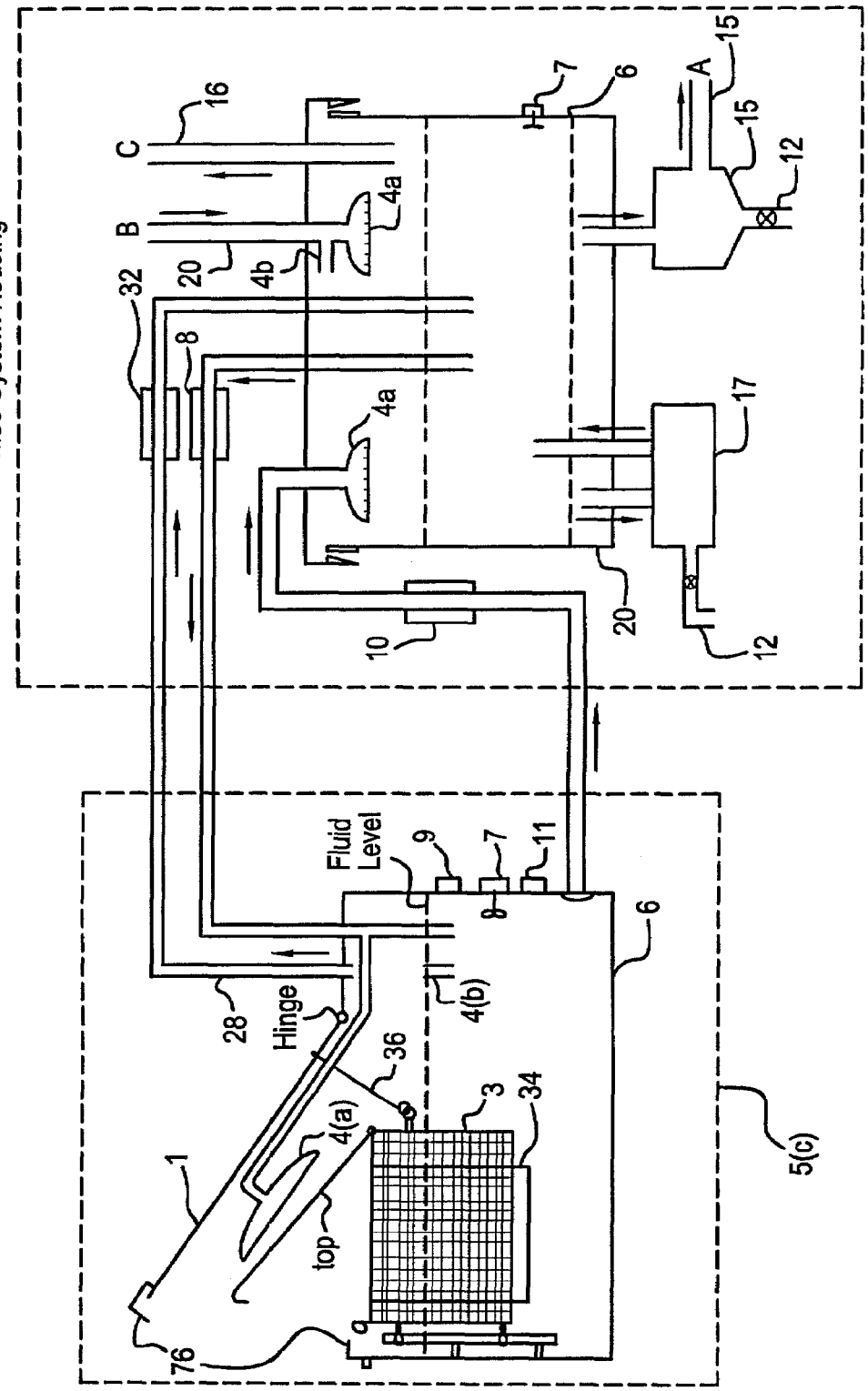
FIG. 1D Anolyte Reaction Chamber Remote is a schematic representation of the anolyte reaction chamber used for separating the anolyte reaction chamber from the basic MEO apparatus. This configuration allows the chamber to be a part of production line or similar use.

The anolyte reaction chamber 5(c) in FIG. 1D is designed to use an anolyte reaction chamber that is exterior to the basic MEO apparatus. The chamber may be integrated into a production process to be used to destroy animal waste as a part of the process. The chamber may be connected to the basic MEO apparatus through tubing and a pumping system. The anolyte is pumped from the buffer tank 20 in the basic MEO apparatus by the pump 8 where it is introduced into the reaction chamber 5(c) through spray head XX as a spray onto the anolyte surface thereby promoting contact with (i.e., oxidation of) any immiscible organic surface layers present in addition to reacting with (i.e., oxidizing) the animal waste dissolved, suspended or submerged within the anolyte in the reaction chamber 5 (c). The inlet to pump 8 is protected by an in-line screen filter 6 which prevents solid particles large enough to clog the spray head 4(a) from exiting the buffer tank 20. Contact of the oxidizing species with incomplete oxidation products that are gaseous at the conditions within the reaction chamber 5(c) may be further enhanced by using conventional techniques for promoting gas/liquid contact (e.g., ultrasonic vibration 9, mechanical mixing 7). An ultraviolet source 11 is introduced into the anolyte reaction chamber 5(c) to decompose the hydrogen peroxide formed by the MEO process into free hydroxyl radicals. The input pump 10 pumps the anolyte and animal waste liquid in the anolyte reaction chamber back to the buffer tank in the basic MEO apparatus through a return tube protected by an in-line screen filter 6 which prevents solid particles large enough to clog the spray head 4(a) from exiting the reaction chamber 5(c). A third tube is connected to the reaction chamber 5(c) to pump out any gas that is present from the original contents or from the MEO process. The gas is pumped by the air pump 32. The return gas tube is submerged in the buffer tank 20 in the basic MEO system so as to oxidize any volatile organic compounds in the gas to $CO_2$ before release to the gas cleaning system 16. Contact of the oxidizing species with incomplete oxidation products that are gaseous at the conditions within the reaction chamber 5(c) may be further enhanced by using conventional techniques for promoting gas/liquid contact (e.g., ultrasonic vibration 9, mechanical mixing 7). The apparatus continuously circulates the anolyte portion of the electrolyte directly from the electrochemical cell 25 through the buffer tank 20 to maximize the concentration of oxidizing species contacting the waste.

The hinged lid 1 is lifted, and the top of the basket 3 is opened. The organic waste is introduced into the basket 3 in the reaction chamber 5(c) where the solid waste remains while the liquid portion of the waste flows into the anolyte. The basket 3 top and the lid 1 are closed and lid 1 has a seal around the opening and it is locked before operation begins. With basket 3 lid closed, the basket 3 is lowered by a lever 36 connected to the lid 1 into the anolyte such that all of its contents are held submerged in the anolyte throughout the oxidization process.

A mechanical device (penetrator 34) may be incorporated into the basket 3 in the anolyte reaction chamber 5(*c*) that create multiple perforations in the outer portion of the solid animal waste so that the anolyte can rapidly penetrate into the interior of the waste. The penetrator 34 serves the same purpose it does in the anolyte reaction chamber 5(*b*) described in the foregoing section. A filter 6 is located at the base of the buffer tank 20 to limit the size of the solid particles to approximately 1 mm in diameter (i.e., smaller that the minimum dimension of the anolyte flow path in the electrochemical cell 25) thereby preventing solid particles large enough to clog the electrochemical cell 25 flow paths from exiting the buffer tank (20).

Figure 1E:
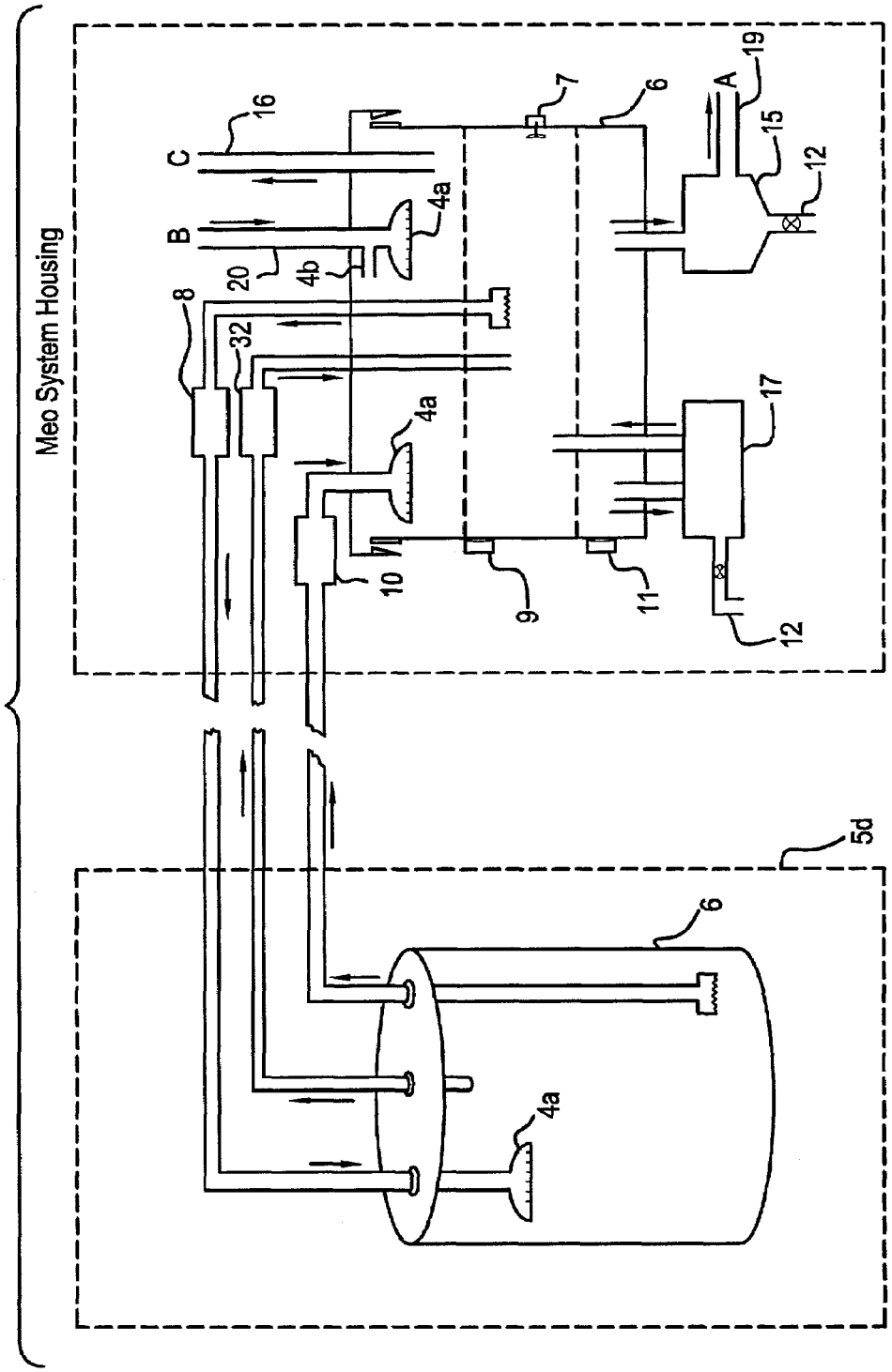
FIG. 1E Anolyte Reaction Chamber Exterior is a schematic representation of a container serving the role of the anolyte reaction chamber that is not a part of the MEO apparatus. Typical of such a container is a 50-gallon drum.

The anolyte reaction chamber 5(*d*) in FIG. 1E is designed to use a closed container exterior to the basic apparatus as the anolyte reaction chamber. FIG. 1E illustrates one example of an exterior container, which in this case is a metal vessel such as a 50-gallon steel drum containing animal waste. The drum may be connected to the basic MEO apparatus through tubing and a pumping system. The anolyte is pumped by the pump 8 from the buffer tank 20 in the basic MEO apparatus into the reaction chamber 5(*d*) where it reacts with the contents and oxidizes the animal waste. The anolyte stream is oscillated within the anolyte reaction chamber 5(*d*) to allow for thorough mixing and for cleaning of the walls of the chamber. The input pump 10 pumps the anolyte and animal waste liquid in the anolyte reaction chamber back to the buffer tank in the basic MEO apparatus through a return tube protected by an in-line screen filter 6 which prevents solid particles large enough to clog the spray head 4(*a*) from exiting the reaction chamber 5(*d*). A third tube is connected to the reaction chamber 5(*d*) through the air pump 32 to pump out any gas that is present from the original contents or from the MEO process. The return gas tube is submerged below the anolyte level in the buffer tank 20 in the basic MEO system so as to oxidize any volatile organic compounds in the gas to $CO_2$ before release to the gas cleaning system 16.

The anolyte from the electrochemical cell 25 is introduced into the buffer tank 20 through the spray head 4(*a*) and stream head 4(*b*). The two heads are designed to increase the exposure of the animal waste to the anolyte by enhancing the mixing in the anolyte reaction chambers 5(*a*,*b*). Introducing the anolyte into the buffer tank 20 as a spray onto the anolyte surface promotes contact with (i.e., oxidation of) any immiscible organic surface layers present.

The MEO apparatus continuously circulates the anolyte portion of the electrolyte directly from the electrochemical cell 25 into the buffer tank 20 to maximize the concentration of oxidizing species contacting the waste. A filter 6 is located at the base of the buffer tank 20 to limit the size of the solid particles to approximately 1 mm in diameter (i.e., smaller than the minimum dimension of the anolyte flow path in the electrochemical cell 25). Contact of the oxidizing species with incomplete oxidation products that are gaseous at the conditions within the buffer tank 20 may be enhanced by using conventional techniques for promoting gas/liquid contact (e.g., ultrasonic vibration 9, mechanical mixing 7). An ultraviolet source 11 is introduced into the buffer tank 20 to decompose the hydrogen peroxide formed by the MEO process into free hydroxyl radicals.

All surfaces of the apparatus in contact with the anolyte or catholyte are composed of stainless steel, glass, or nonreactive polymers (e.g., PTFE, PTFE lined tubing, etc). These materials provide an electrolyte containment boundary to protect the components of the MEO apparatus from being oxidized by the electrolyte.

The anolyte circulation system contains a pump 19 and a removal and treatment system 15 (e.g., filter, centrifuge, hydrocyclone, etc,) to remove any insoluble inorganic compounds that form as a result of mediator or electrolyte ions reacting with anions of or containing halogens, sulfur, phosphorous, nitrogen, etc. that may be present in the waste stream thus preventing formation of unstable compounds (e.g., perchlorates, etc.). The anolyte is then returned to the electrochemical cell 25, where the oxidizing species are regenerated, which completes the circulation in the anolyte system (A).

The residue of the inorganic compounds is flushed out of the treatment system 15 during periodic maintenance if necessary. If warranted, the insoluble inorganic compounds are converted to water-soluble compounds using any one of several chemical or electrochemical processes.

Waste is added to the reaction chambers 5(*a*,*b*,*c*) either continuously or in the batch mode depending on the anolyte reaction chamber configuration chosen.

The MEO system apparatus incorporates two methods that may control the rate of destruction of animal waste and control the order in which organic molecular bonds are broken. In the first method the anolyte temperature is initially at or below the operating temperature and subsequently increased by the thermal controls 21 and 22 until the desired operating temperature for the specific waste stream is obtained. In the second method the animal waste is introduced into the apparatus, with the concentration of electrochemically generated oxidizing species in the anolyte being limited to some predetermined value between zero and the maximum desired operating concentration for the waste stream by controlling the electric current in the electrochemical cell 25 with the DC power supply 29 and subsequently increased to the desired operating concentration. These two methods can be used in combination.

The electrolyte is composed of an aqueous solution of mediator species and electrolytes appropriate for the species selected and is operated within the temperature range from approximately 0° C. to slightly below the boiling point of the electrolytic solution, usually less then 100° C., at a temperature or temperature profile most conducive to the desired waste destruction rate (e.g., most rapid, most economical, etc.). The acid, alkaline, or neutral salt electrolyte used is determined by the conditions in which the species may exist.

Considerable attention has been paid to halogens, especially chlorine and their deleterious interactions with silver mediator ions, however this is of much less concern or importance to this invention for the following two reasons. First, the biological waste considered herein typically contains relatively small amounts of these halogen elements compared to the halogenated solvents and nerve agents addressed in the cited patents. Second, the wide range of properties (e.g., oxidation potential, solubility of compounds, cost, etc.) of the mediator species claimed in this patent allows selection of a single or mixture of mediators either avoiding formation of insoluble compounds, easily recovering the mediator from the precipitated materials, or being sufficiently inexpensive so as to allow the simple disposal of the insoluble compounds as waste, while still maintaining the capability to oxidize (i.e., destroy) the animal waste economically.

The waste destruction process may be monitored by several electrochemical and physical methods. First, various cell voltages (e.g., open circuit, anode vs. reference electrode, ion specific electrode, etc.) yield information about the ratio of oxidized to reduced mediator ion concentrations which may be correlated with the amount of reducing agent (i.e., animal waste) either dissolved in or wetted by the anolyte. Second, if a color change accompanies the transition of the mediator species between its oxidized and reduced states (e.g., heteropoly blues, etc.), the rate of decay of the color associated with the oxidized state, under zero current conditions, could be used as a gross indication of the amount of reducing agent (i.e., oxidizable waste) present. If no color change occurs in the mediator, it may be possible to select another mediator to simply serve as the oxidization potential equivalent of a pH indicator. Such an indicator is required to have an oxidation potential between that of the working mediator and the organic species, and a color change associated with the oxidization state transition.

The anolyte reaction chambers $5(a,b,c,d)$ and buffer tank 20 off-gas consists of $CO_2$ and CO from complete and incomplete combustion (i.e., oxidation) of the carbonaceous material in the animal waste, and possibly oxygen from oxidation of water molecules at the anode. Standard anesthesiology practice requires these three gases to be routinely monitored in real time under operating room conditions, while many other respiratory related medical practices also require real time monitoring of these gases. Thus, a mature industry exists for the production of miniaturized gas monitors directly applicable to the continuous quantitative monitoring of anolyte off-gas for the presence of combustion products. Although usually not as accurate and requiring larger samples, monitors for these same gasses are used in the furnace and boiler service industry for flue gas analysis.

The anolyte is circulated into the reaction chambers $5(a,b,)$ and buffer tank 20 through the electrochemical cell 25 by pump 19 on the anode 26 side of the membrane 27. A membrane 27 in the electrochemical cell 25 separates the anolyte portion and catholyte portion of the electrolyte.

Small thermal control units 21 and 22 are connected to the flow stream to heat or cool the anolyte to the selected temperature range. If warranted a heat exchanger 23 can be located immediately upstream from the electrochemical cell 25 to lower the anolyte temperature within the cell to the desired level. Another heat exchanger 24 can be located immediately upstream of the anolyte reaction chamber inlet to control the anolyte temperature in the reaction chamber to within the desired temperature range to affect the desired chemical reactions at the desired rates.

The electrochemical cell 25 is energized by a DC power supply 29, which is powered by the AC power supply 30. The DC power supply 29 is low voltage high current supply usually operating below 4 v DC but not limited to that range. The AC power supply 30 operates off a typical 110 v AC line for the smaller units and 240 v AC for the larger units.

The oxidizer species population produced by electrochemical generation (i.e., anodic oxidation) of the oxidized form of the redox couples referenced herein can be enhanced by conducting the process at low temperatures, thereby reducing the rate at which thermally activated parasitic reactions consume the oxidizer.

Reaction products resulting from the oxidation processes occurring in the anolyte system (A) that are gaseous at the anolyte operating temperature and pressure are discharged to the condenser 13. The more easily condensed products of incomplete oxidation are separated in the condenser 13 from the anolyte off-gas stream and are returned to the anolyte reaction chamber $5(a,b)$ or the buffer tank 20 for further oxidation. The non-condensable incomplete oxidation products (e.g., low molecular weight organics, carbon monoxide, etc.) are reduced to acceptable levels for atmospheric release by a gas cleaning system 16. The gas cleaning system 16 is not a necessary component of the MEO apparatus for the destruction of most types of animal waste.

If the gas cleaning system 16 is incorporated into the MEO apparatus, the anolyte off-gas is contacted in a counter current flow gas scrubbing system in the off-gas cleaning system 16, wherein the noncondensibles from the condenser 13 are introduced into the lower portion of the column through a flow distribution system of the gas cleaning system 16, and a small side stream of freshly oxidized anolyte direct from the electrochemical cell 25 is introduced into the upper portion of the column. This results in the gas phase continuously reacting with the oxidizing mediator species as it rises up the column past the downflowing anolyte. Under these conditions the gas about to exit the top of the column will have the lowest concentration of oxidizable species and also be in contact with the anolyte having the highest concentration of oxidizer species, thereby promoting reduction of any air pollutants present down to levels acceptable for release to the atmosphere. Gas-liquid contact within the column may be promoted by a number of well established methods (e.g., packed column, pulsed flow, ultrasonic mixing, etc,) that does not result in any meaningful backpressure within the anolyte flow system. Anolyte exiting the bottom of the countercurrent scrubbing column is discharged into the anolyte reaction chamber $5(a,b,c)$ or buffer tank 20 and mixed with the remainder of the anolyte. Unique waste compositions may result in the generation of unusual gaseous products that could more easily be removed by more traditional air pollution technologies. Such methodologies could be used in series with the afore described system as a polishing process treating the gaseous discharge from the countercurrent column, or if advantageous, instead of it. The major products of the oxidation process are $CO_2$, water, and minor amounts of CO and inorganic salts, where the $CO_2$ is vented 14 out of the system.

An optional inorganic compound removal and treatment systems 15 is used should there be more than trace amount of halogens, or other precipitate forming anions present in the animal waste being processed, thereby precluding formation of unstable oxycompounds (e.g., perchlorates, etc.).

The MEO process proceeds until complete destruction of the animal waste has been affected or be modified to stop the process at a point where the destruction of the animal waste is incomplete. The reason for stopping the process is that: a) the organic materials are benign and do not need further treatment, or b) the organic materials may be used in the form they have been reduced and thus would be recovered for that purpose. The organic compounds recovery system 17 is used to perform this process.

Catholyte System (B)

The bulk of the catholyte is resident in the catholyte reaction chamber 31. The catholyte portion of the electrolyte is circulated by pump 43 through the electrochemical cell 25 on the cathode 28 side of the membrane 27. The catholyte portion of the electrolyte flows into a catholyte reservoir 31. Small thermal control units 45 and 46 are connected to the catholyte flow stream to heat or cool the catholyte to the selected temperature range.

External air is introduced through an air sparge 37 into the catholyte reservoir 31. In the case where nitrogen compounds (such as nitrates) are used in the catholyte, the oxygen contained in the air oxidizes any nitrous acid and the small amounts of nitrogen oxides ($NO_x$), produced by the cathode reactions. Contact of the oxidizing gas with nitrogen compounds (nitrous acid) may be enhanced by using conventional techniques for promoting gas/liquid contact such as ultrasonic vibration 48, mechanical mixing 35, etc. Systems using non-nitric acid catholytes may also require air sparging to dilute and remove off-gas such as hydrogen. An off-gas cleaning system 39 is used to remove any unwanted gas products (e.g. $NO_2$, etc.). The cleaned gas stream, combined with the unreacted components of the air introduced into the system is discharged through the atmospheric vent 47.

Optional anolyte recovery system 41 is positioned on the catholyte side. Some mediator oxidizer ions may cross the membrane 27 and this option is available if it is necessary to remove them through the anolyte recovery system 41 to maintain process efficiency or cell operability, or their economic worth necessitates their recovery. Operating the electrochemical cell 25 at higher than normal membrane 27 current densities (i.e., above about 0.5 amps/cm$^2$) increases the rate of waste destruction, but also result in increased mediator ion transport through the membrane into the catholyte. It may be economically advantageous for the electrochemical cell 25 to be operated in this mode. It is advantageous whenever the replacement cost of the mediator species or removal/recovery costs are less than the cost benefits of increasing the waste throughput (i.e., oxidation rate) of the electrochemical cell 25. Increasing the capitol cost of expanding the size of the electrochemical cell 25 can be avoided by using this operational option.

MEO Controller

Figure 2:
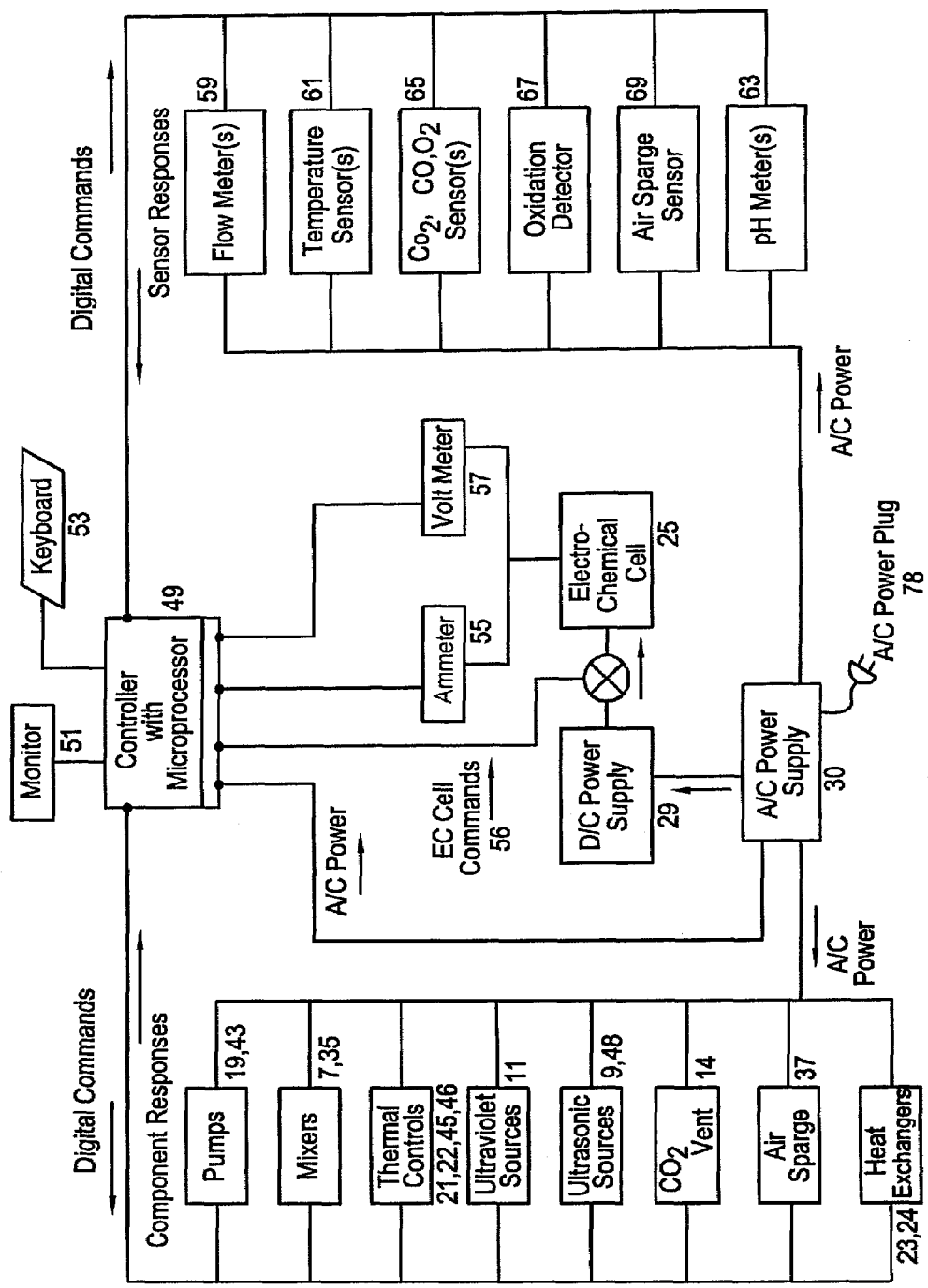
FIG. 2 MEO Controller for System Model 5.$b$ is a schematic representation of the MEO electrical and electronic systems.

An operator runs the MEO Apparatus (FIG. 1A) by using the MEO Controller depicted in FIG. 2 MEO Controller. The controller 49 with microprocessor is connected to a monitor 51 and a keyboard 53. The operator inputs commands to the controller 49 through the keyboard 53 responding to the information displayed on the monitor 51. The controller 49 runs a program that sequences the steps for the operation of the MEO apparatus. The program has pre-programmed sequences of standard operations that the operator may follow or may choose his own sequences of operations. The controller 49 allows the operator to select his own sequences within limits that assure a safe and reliable operation. The controller 49 sends digital commands that regulates the electrical power (AC 30 and DC 29) to the various components in the MEO apparatus; pumps 19 and 43, mixers 7 and 35, thermal controls 21, 22, 45, 46, ultraviolet sources 11, ultrasonic sources 9 and 48, $CO_2$ vent 14, air sparge 37, and electrochemical cell 25. The controller receives component response and status from the components. The controller sends digital commands to the sensors to access sensor information through sensor responses. The sensors in the MEO apparatus provide digital information on the state of the various components. Sensors measure flow rate 59, temperature 61, pH 63, $CO_2$, CO, $O_2$, venting 65, degree of oxidation 67, air sparge sensor 69, etc. The controller 49 receives status information on the electrical potential (voltmeter 57) across the electrochemical cell, or individual cells if a multi-cell configuration, and between the anode(s) and reference electrodes internal to the cell(s) 25 and the current (ammeter 55) flowing between the electrodes within each cell.

Example System Model

Figure 3:
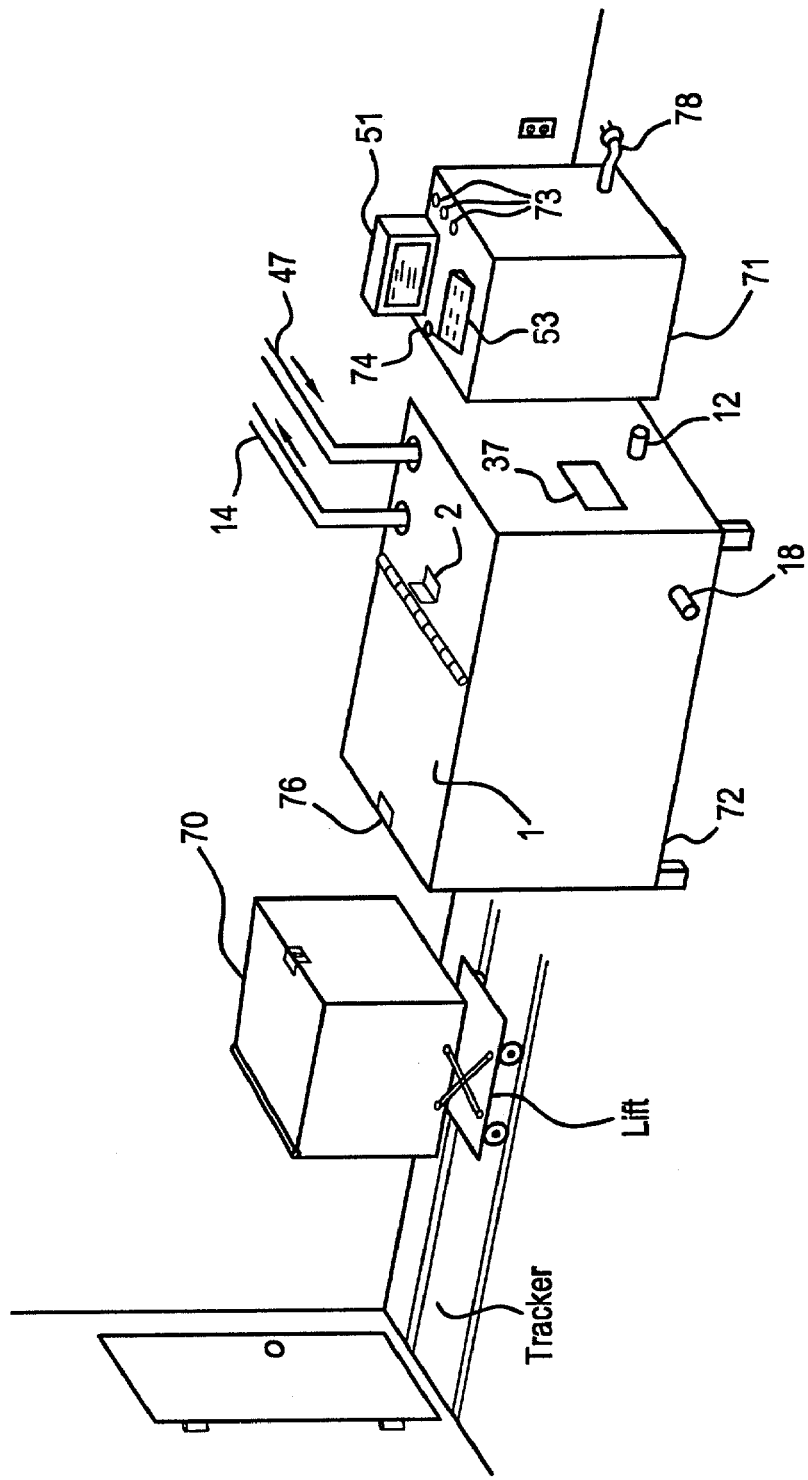
FIG. 3 MEO System Model 5.$b$ is a schematic representation of a preferred embodiment.

A preferred embodiment, MEO System Model 5.$b$ (shown in FIG. 3 MEO System Model 5.($b$) is sized for use for a small to mid-size application for the destruction of solids and mixtures of solids and liquid animal waste being batch feed. This embodiment depicts a configuration using the system apparatus presented in FIGS. 1A and 1C. Other preferred embodiments (representing FIGS. 1B, 1D, and 1E) have differences in the external configuration and size but are essentially the same in internal function and components as depicted in FIGS. 1A and 1C. The preferred embodiment in FIG. 3 comprises a housing 72 constructed of metal or high strength plastic surrounding the electrochemical cell 25, the electrolyte and the foraminous basket 3. The AC power is provided to the AC power supply 30 by the power cord 78. A monitor screen 51 is incorporated into the housing 72 for displaying information about the system and about the waste being treated. Additionally, a control keyboard 53 is incorporated into the housing 72 for inputting information into the system. The monitor screen 51 and the control keyboard 53 may be attached to the system without incorporating them into the controller housing 71. In a preferred embodiment, status lights 73 are incorporated into the housing 72 for displaying information about the status of the treatment of the animal waste material. An air sparge 37 is incorporated into the housing 72 to allow air to be introduced into the catholyte reaction chamber 31 below the surface of the catholyte. In addition, a $CO_2$ vent 14 is incorporated into the housing 72 to allow for $CO_2$ release from the anolyte reaction chamber via the gas cleaning system 16 housed within. In a preferred embodiment, the housing includes means for cleaning out the MEO waste treatment system, including a flush(s) 18 and drain(s) 12 through which the anolyte and catholyte pass. The preferred embodiment further comprises an atmospheric vent 47 facilitating the releases of gases into the atmosphere from the catholyte reaction chamber 31 via the gas cleaning system 39. Other preferred embodiment systems are similar in nature but are scaled up in size to handle a larger capacity of waste, such as a incinerator replacement units.

The system has a control keyboard 53 for input of commands and data. The On/Off button 74 is used to turn the apparatus power on and off. There is a monitor screen 51 to display the systems operation and functions. Below the keyboard 53 and monitor screen 51 are the status lights 73 for on, off, and standby.

Animal waste is introduced into the anolyte reaction chambers 5($b$) as depicted in FIG. 1C. In the case of solid, mixtures, and batch feed operation, the hinged lid 1 is opened and the animal waste is deposited in the basket 3 in the chamber 5($b$). The top of basket 3 is closed and the basket 3 is lowered by a lever 36 attached to lid 1 so that the animal waste is totally submerged in the anolyte. Lid 1 is closed and lid stop 2 keeps the lid opening controlled. The hinged lid 1 is equipped with a locking latch 76 that is operated by the controller 49. A penetrator 34 attached to the basket 3 punctures the solids in the basket 3 thus increasing the surface area exposed to the oxidizer and providing mediator flow paths into the interior of the solid waste.

In the chamber 5($b$) is the aqueous acid, alkali, or neutral salt electrolyte and mediated oxidizer species solution in which the oxidized form of the mediator redox couple initially may be present or may be generated electrochemically after introduction of the waste and application of DC power 29 to the electrochemical cell 25. Similarly, the waste may be introduced when the anolyte is at or below room temperature, operating temperature or some optimum intermediate temperature. DC power supply 29 provides direct current to an electrochemical cell 25. Pump 19 circulates the anolyte portion of the electrolyte and the animal waste material is rapidly oxidized at temperatures below 100° C. and at ambient pressure. An in-line filter 6 prevents solid particles large enough to clog the electrochemical cell 25 flow paths from exiting this reaction chambers 5(*b*). The oxidation process continues to break the materials down into smaller and smaller molecules until the products are $CO_2$, water, and some CO and inorganic salts. Any residue is pacified in the form of a salt and may be periodically removed through the Inorganic Compound Removal and Treatment System 15 and drain outlets 12. The basic design of the MEO apparatus permits the user to change the type of electrolyte without having to alter the equipment in the apparatus. The changing of the electrolyte is accomplished by using the drain(s) 12 and flush(s) 18 or by opening the anolyte reaction chamber 5(*b*) and catholyte reaction chamber 31 to introduce the electrolyte(s). The ability to change the type of electrolyte(s) allows the user to tailor the MEO process to differing waste properties. The catholyte reservoir 31 has a screwed top 33 (shown in FIG. 1A), which allow access to the reservoir 31 for cleaning and maintenance by service personnel.

The MEO process advantageous properties of low power consumption and very low loses of the mediated oxidizer species and electrolyte, provide as an option for the device to be operated at a low power level during the day to achieve a slow rate of destruction of the animal waste throughout the day. While the MEO apparatus is in this mode, animal waste is added as it is generated throughout the day and the unit placed in full activation during non-business hours.

The compactness of the device makes it ideal for small and mid-size applications as well as being suitable for use with high volume inputs of industrial processes activities. The process operates at low temperature and ambient atmospheric pressure and does not generate toxic compounds during the destruction of the animal waste, making the process indoors compatible. The system is scalable to a unit large enough to handle a major commercial operation. The $CO_2$ oxidation product from the anolyte system A is vented out the $CO_2$ vent 14. The off-gas products from the catholyte system B is vented through the atmospheric air vent 47.

Steps of the Operation of the MEO System Model 5.*b*

The steps of the operation of the MEO process are depicted in FIG. 4 MEO System Model 5.*b* Operational Steps. These operational steps are presented to illustrate the operation of one of the MEO apparatus' from the four configurations previously discussed for oxidizing the various types of animal waste. When other anolyte reaction chambers 5(*a,c,d*) configurations are used the series of steps would be similar to the ones for FIG. 1C which covers solids, mixtures of solids and liquids being processed in a batch feed mode.

This MEO apparatus is contained in the housing 72. The MEO system is started 81 by the operator engaging the 'ON' button 74 on the control keyboard 53. The system controller 49, which contains a microprocessor, runs the program that controls the entire sequence of operations 82. The monitor screen 51 displays the steps of the process in the proper sequence. The status lights 73 on the panel provide the status of the MEO apparatus (e.g. on, off, ready, standby).

The animal waste is introduced into the anolyte reaction chambers 5(*b*) as depicted in FIG. 1C. In the case of solids, mixtures, and batch operation, lid 1 is opened and the animal waste (which can be in liquid, solid, and a mixture) is placed 83 in the basket 3, whereupon the solid portion of the waste is retained and the liquid portion flows through the basket and into the anolyte. The locking latch 76 is activated.

The pumps 19 and 43 begin circulation 85 of the anolyte 87 and catholyte 89, respectively. As soon as the electrolyte circulation is established throughout the system, the mixers 7 and 35 begin to operate 91 and 93. Depending upon waste characteristics (e.g., reaction kinetics, heat of reaction, etc.) it may be desirable to introduce the waste into a room temperature or cooler anolyte system with little or none of the mediator redox couple in the oxidized form. Once flow is established the thermal controls units 21, 22, 45, and 46 are turned on 95/97, initiating predetermined anodic oxidation and electrolyte heating programs.

The electrochemical cell 25 is energized 94 (by electrochemical cell commands 56) to apply the correct voltage and current as is monitored by the voltmeter 57 and ammeter 55 determined by the controller program. By using programmed electrical power levels and electrolyte temperature it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions.

The ultrasonic sources 9 and 48 and ultraviolet systems 11 are activated 99 and 101 in the anolyte reaction chambers 5(*b*) and catholyte reaction chamber 31 respectively, if those options are chosen in the controller program.

The $CO_2$ vent 14 is activated 103 to release $CO_2$ from the animal waste oxidation process in the anolyte reaction chambers 5(*b*). Air sparge 37 draws air 105 into the catholyte reservoir 31, and the air is discharged out the atmospheric vent 47. The progress of the destruction process may be monitored in the controller (oxidation sensor 67) by various cell voltages and currents 55, 57 (e.g., open circuit, anode vs. reference electrode, ion specific electrodes, etc,) as well as monitoring anolyte off-gas (using the sensor 65) composition for $CO_2$, CO and oxygen content.

When the oxidation sensors 65 and 67 determine the desired degree of waste destruction has been obtained 107, the system goes to standby 109. The system operator executes system shutdown 111 using the controller keyboard 53.

EXAMPLES

The following examples illustrate the application of the process and the apparatus.

Example (1) Destruction of Swine Manure

The environmental effects of swine manure storage systems and application methods are a concern, particularly with respect to surface water and ground water quality and to air quality as affected by odors and gaseous emissions from large-scale swine production operations. Over 50% of the swine production is done in confined quarters and the resulting manure is placed in anaerobic lagoons. The manure nitrogen is converted into ammonia in these lagoons and is lost to the atmosphere.

The swine diet is formulated with corn and/or grain sorghum and soy meal. Vitamins and minerals are added to the feed to makeup for any deficiency in the basic grain composition. The manure is a relatively homogeneous composition for the swine in confined areas. A sample of both air-dried and fresh moist manure was collected for test purposes. Each of the two samples was tested in the MEO apparatus separately. The MEO apparatus was operated at 50° C. for both samples. The swine manure was totally destroyed producing water and $CO_2$. There was a small amount of inorganic salt remaining in the settling tank of the MEO apparatus after completion of the destruction.

Example (2) Efficient and Environmentally Safe Products

The MEO process produces $CO_2$, water, and trace inorganic salts all of which are considered benign for introduction into the environment by regulatory agencies. The cost of using the MEO process in this invention is competitive with both the incineration and landfill methodologies. The MEO process is uniquely suited for destruction of animal waste because water, which constitutes a major portion of this waste (e.g., tissue, bodies fluids, etc.) is either benign or actually a source of secondary oxidizing species, rather than parasitic reactions competing for the mediator oxidizing species. Furthermore, the energy that must be provided in the MEO process to heat the waste stream water component from ambient to the electrolyte operating temperature (i.e., 80° C. maximum temperature increase) is trivial compared to the water enthalpy increase required in autoclave or incineration based processes.

Example (3) Benign In-door Operation

The system is unique relative to earlier art, since it is built to operate in an indoor environment such as a production or assembly line where it must be compatible with people working in close proximity to the system. The system is suitable for indoor use in spaces inhabited by personnel as well as for industrial workspaces similar to an incinerator building.

Example (4) Inheritantly Safe Operation

The system is built to require limited operating skill. The system controller is programmed to guide the operator through the normal operating cycle as well as the various options available. The system is accessible during its operating cycle so that additional animal waste may be added to waste in process, while remaining compatible with the room environment. When new animal waste is to be added to the system during operation the operator selects that option. The system controller recycles the system operational steps back to step 83. It deactivates steps 85, 87, 89, 91, 93, 94, 95, 97, 99, 101 and maintains steps 103 and 105 in their active mode. The controller releases the locking latch 76 and the operator adds additional animal waste. After he has completed the addition he selects the restart option. The system recycles back through these steps to continue the processing of the waste.

Example (5) Chemical Reactions are Safe

The system is built to operate with materials that are safe to handle in the environment in which it is to be used. The animal waste contains little or no substances that react with our choice of electrolytes to produce volatile compounds that offer a problem in the room environment. The system may operate at temperatures from approximately 0° C. to slightly less then the boiling point of the electrolyte (i.e., usually less then 100° C.) and at ambient atmospheric pressure, which adds to the indoor compatibility.

Example (6) A Green Machine

The simplicity of the new system built for use with animal waste produces a system more economically to operate and cleaner to use than existing waste treatments. The system complexity is reduced by comparison to previous MEO systems, since there is not a requirement to deal with large quantities of halogens. The system is truly a 'green machine' in the sense of an environmentally benign system.

Example (7) System Flexibility

The system is built so that the composition of the electrolyte may be changed to adapt the system to a selected composition of the animal waste stream. Different types of animal waste can be processed by the same system by either using the same electrolyte or replacing the mediator and electrolyte (either or both the catholyte and anolyte) more suitable for the alternative animal waste. The system is configured with ports to flush and drain the anolyte and catholyte separately

Example (8) System By-Products are Safe

The system flexibility provides for the introduction of more then one mediator ion resulting in marked improvement in the efficiency of the electrolyte. Furthermore, the wide choice of mediators listed in Table I or available as POMs, and electrolytes in this patent, desensitizes the system to the formation of participates in solution (i.e. allows increased ease in preventing formation of unstable oxy compounds).

While the invention has been described with reference to specific embodiments, modifications and variations of the invention may be constructed without departing from the scope of the invention, which is defined in the following characteristics and features.

The invention provides the following new characteristics and features:

1. A process for treating and oxidizing animal waste materials comprising disposing an electrolyte in an electrochemical cell, separating the electrolyte into an anolyte portion and a catholyte portion with an ion-selective membrane or semipermeable membrane applying a direct current voltage between the anolyte portion and the catholyte portion, placing the animal waste materials in the anolyte portion, and oxidizing the animal waste materials in the anolyte portion with a mediated electrochemical oxidation (MEO) process, wherein the anolyte portion further comprises a mediator in aqueous solution and the electrolyte is an acid, neutral or alkaline aqueous solution.

2. The process of paragraph 1, wherein:

a. the anolyte portion further comprises one or more simple anions mediator ion species selected from the group described in Table I (in the aqueous solution and the electrolyte is an acid, neutral or alkaline solution;

b. the oxidizing species are selected from one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

c. the oxidizing species are selected from one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

d. the oxidizing species are selected from one or more of any heteropolyanions containing at least one heteroatom type (i.e., element) contained in both Table I and Table II in the aqueous solutions and the electrolyte is an acid, neutral, or alkaline aqueous solution;

e. the oxidizing species are selected from combinations of anion redox couple mediators from any or all of the previous four subparagraphs (2a., 2b., 2c., and 2d.);

f. adding stabilizing compounds to the electrolyte such as tellurate or periodate ions which serve to overcome and stabilize the short lifetime of the oxidized form of the higher oxidation state species of the simple and complex anion redox couple mediators;

g. each of the species has normal valence states and higher valence oxidizing states and further comprising creating the higher valence oxidizing states of the oxidizing species by stripping electrons from normal valence state species in the electrochemical cell;

h. the oxidizing species are "super oxidizers" (SO) typically exhibit oxidation potentials at least equal to that of the $Ce^{+3}/Ce^{+4}$ redox couple (i.e., 1.7 volts at 1 molar, 25° C. and pH 1) which are redox couple species that have the capability of producing free radicals such as hydroxyl or perhydroxyl and further comprising creating secondary oxidizers by reacting the SO's with water;

i. using an alkaline solution for aiding decomposing of the animal waste materials derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution;

j. using an alkaline anolyte solution that absorbs $CO_2$ forming from oxidation of the animal waste sodium bicarbonate/carbonate solution which subsequently circulates through the electrochemical cell, producing a percarbonate oxidizer;

k. using oxidizing species from the MEO process inorganic free radicals generated in aqueous solutions from species such as but not limited to carbonate, azide, nitrite, nitrate, phosphite, phosphate, sulfite, sulfate, selenite, thiocyanate, chloride, bromide, iodide, and formate oxidizing species;

l. the regeneration of the oxidizer part of the redox couple in the anolyte portion is done within the electrochemical cell;

m. the membrane (separator between anolyte and catholyte solutions) can be microporous plastic, sintered glass frit, etc.;

n. the impression of an AC voltage upon the DC voltage to retard the formation of cell performance limiting surface films on the electrode;

o. disposing a foraminous basket in the anolyte;

p. adding oxygen (this is necessary only for $HNO_3^-$ or $NO_3^-$ salts) to the catholyte portion;

q. the oxidizer species addressed in this patent are described in: Table I (simple anions); Type I isopolyanions containing tungsten, molybdenum, vanadium, niobium, tantalum, or combinations thereof as addenda atoms; Type I heteropolyanions formed by incorporation into the aforementioned isoopolyanions, as heteroatoms, any of the elements listed in Table II, either singly or in combinations thereof; or any heteropolyanions containing at least one heteroatom type (i.e., element) contained in both Table I and Table II;

r. lower the temperature (e.g. between 0° C. and room temperature) of the anolyte before it enters the electrochemical cell to enhance the generation of the oxidized form of the anion redox couple mediator;

s. raise the temperature of the anolyte entering the anolyte reaction chamber to affect the desired chemical reactions at the desired rates following the lowering of the temperature of the anolyte entering the electrochemical cell;

t. the evolved oxygen from the anode is feed to a hydrogen fuel apparatus to increase the percentage oxygen available from the ambient air.

3. The process of paragraph 1, wherein:

a. introducing an ultrasonic energy into the anolyte portion rupturing cell membranes in the biological waste materials by momentarily raising local temperature within the cell membranes with the ultrasonic energy to above several thousand degrees and causing cell membrane failure;

b. introducing ultraviolet energy into the anolyte portion and decomposing hydrogen peroxide and ozone into hydroxyl free radicals therein, thereby increasing efficiency of the MEO process by converting products of electron consuming parasitic reactions (i.e., ozone and hydrogen peroxide) into viable free radical (i.e., secondary) oxidizers without the consumption of additional electrons;

c. using a surfactant to be added to the anolyte promote dispersion of the animal waste or intermediate stage reaction products within the aqueous solution when these animal waste or reaction products are not water-soluble and tend to form immisible layers;

d. using simple and/or complex redox couple mediators, and attacking specific organic molecules with the oxidizing species while operating at low temperatures thus preventing the formation of dioxins and furans;

e. breaking down animal waste materials into organic compounds and attacking the organic compounds using either the simple and/or complex anion redox couple mediator or inorganic free radicals to generating organic free radicals;

f. raising normal valence state anions to a higher valence state and stripping the normal valence state anions of electrons in the electrochemical cell; [The oxidized forms of any other redox couples present are produced either by similar anodic oxidation or reaction with the oxidized form of other redox couples present. The oxidized species of the redox couples oxidize the animal waste molecules and are themselves converted to their reduced form, whereupon they are reoxidized by either of the aforementioned mechanisms and the redox cycle continues]

g. circulating anions through an electrochemical cell to affect the anodic oxidation of the reduced form of the reversible redox couple into the oxidized form;

h. contacting anions with animal waste materials in the anolyte portion;

i. circulating anions through the electrochemical cell;

j. involving anions with an oxidation potential above a threshold value of 1.7 volts (i.e., super oxidizer) in a secondary oxidation process and producing oxidizers;

k. adding a ultraviolet (UV) energy source to the anolyte portion and augmenting secondary oxidation processes, breaking down hydrogen peroxide and ozone into hydroxyl free radicals, and thus increasing the oxidation processes; and l. the oxidizer species addressed in this patent are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups.

4. The process of paragraph 1, further comprising:

a. using oxidizer species that are found in situ in the, waste to be destroyed, by circulating the waste-anolyte mixture through an electrochemical cell where the oxidized form of the in situ reversible redox couple formed by anodic oxidation or alternately reacting with the oxidized form of a more powerful redox couple, if added to the anolyte and anodically oxidized in the electrochemical cell, thereby destroying the animal waste material;

b. using an alkaline electrolyte, such as but not limited to NaOH or KOH with mediator species wherein the reduced form of said mediator redox couple displays sufficient solubility in said electrolyte to allow the desired oxidation of the animal waste to proceed at a practical rate. The oxidation potential of redox reactions producing hydrogen ions (i.e., both mediator species and organic waste molecules reactions) are inversely proportional to the electrolyte pH, thus with the proper selection of a mediator redox couple, it is possible, by increasing the electrolyte pH, to minimize the electric potential required to affect the desired oxidation process, thereby reducing the electric power consumed per unit mass of animal waste destroyed;

c. the aqueous solution is chosen from acids such as but not limited to nitric acid, sulfuric acid, or phosphoric acid, or mixtures thereof; or alkalines such as but not limited to of sodium hydroxide or potassium hydroxide, or mixtures thereof, or neutral electrolytes, such as but not limited to sodium or potassium nitrates, sulfates, or phosphates or mixtures thereof; and d. the use of ultrasonic energy induce microscopic bubble implosion which is used to affect a desired reduction in sized of the individual second phase waste volumes dispersed in the anolyte.

5. The process of paragraph 1, further comprising:

a. interchanging oxidizing species in a preferred embodiment without changing equipment; and b. the electrolyte is acid, neutral, or alkaline in aqueous solution.

6. The process of paragraph 1, further comprising:

a. separating the anolyte portion and the catholyte portion with a ion-selective or semi-permeable membrane, or microporous polymer membrane, ceramic membrane, or sintered glass frit, or other similar membrane;

b. applying an externally induced electrical potential induced between the anode(s) and cathode(s) plates of the electrochemical cell at a electrical potential sufficient to form the oxidized form of the redox couple having the highest oxidation potential in the anolyte;

c. introducing animal waste materials into the anolyte portion;

d. forming the reduced form of one or more reversible redox couples by contacting with oxidizable molecules, the reaction with which oxidizes the oxidizable material with the concuminent reduction of the oxidized form of the reversible redox couples to their reduced form;

e. the ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidation processes;

f. oxidation potentials of redox reactions producing hydrogen ions are inversely related to pH;

g. the process is performed at a temperature from slightly above 0° C. to slightly below the boiling point of the electrolyte usually less then 100° C.;

h. the temperature at which the process is performed is varied;

i. the treating and oxidizing animal waste comprises treating and oxidizing solid waste;

j. the treating and oxidizing animal waste comprises treating and oxidizing liquid waste;

k. the treating and oxidizing animal waste comprises treating and l. removing and treating precipitates resulting from combinations of oxidizing species and other species released from the animal waste during destruction.

7. The process of paragraph 1, further comprising that it is not necessary for both the anolyte and catholyte solutions to contain the same electrolyte rather each electrolyte system may be independent of the other, consisting of an aqueous solution of acids, typically but not limited to nitric, sulfuric or phosphoric; alkali, typically but not limited to sodium or potassium hydroxide; or neutral salt, typically but not limited to sodium or potassium salts of the afore mentioned strong acids.

8. The process of paragraph 1, further comprising the operating of the electrochemical cell at a current density greater then 0.5 amp per square centimeter across the membrane, eventhough this is the limit over which there is the possibility that metallic anions may leak through the membrane in small quantities, and recovering the metallic anions through a devise such as a resin column thus allowing a greater rate of destruction of materials in the anolyte chamber.

9. The process of paragraph 1, wherein:

a. the catholyte solution further comprises an aqueous solution and the electrolyte in the solution is composed of acids, typically but not limited to nitric, sulfuric or phosphoric; or alkali, typically but not limited to sodium or potassium hydroxide; or neutral salt, typically but not limited to sodium or potassium salts of the afore mentioned strong acids;

b. adding oxygen (this is necessary only for $HNO_3^-$ or $NO_3^-$ salts) to the catholyte portion;

c. concentration of electrolyte in the catholyte is governed by its effect upon the conductivity of the catholyte solution desired in the electrochemical cell;

d. ultrasonic energy induced microscopic bubble implosion is used to affect vigorous mixing in the catholyte solution where it is desirable to oxidize nitric acid and the small amounts of nitrogen oxides when nitric acid is used in the catholyte electrolyte;

e. mechanical mixing is used to affect vigorous mixing in the catholyte solution where it is desirable to oxidize nitric acid and the small amounts of nitrogen oxides;

f. air is introduced into the catholyte solution to promote oxidation of nitric acid and the small amounts of nitrogen oxides when nitric acid is used in the catholyte electrolyte;

g. air is introduced into the catholyte solution to dilute any hydrogen produced in the catholyte solution before being released; and h. hydrogen gas evolving from the cathode is feed to an apparatus that uses hydrogen as a fuel such as a proton exchange membrane (PEM) fuel cell.

10. An apparatus for treating and oxidizing animal waste materials comprising an electrochemical cell, an electrolyte disposed in the electrochemical cell, an ion-selective or semipermeable membrane, disposed in the electrochemical cell for separating the cell into anolyte and catholyte chambers and separating the electrolyte into anolyte and catholyte portions, electrodes further comprising an anode(s) and a cathode(s) disposed in the electrochemical cell respectively in the anolyte and catholyte chambers and in the anolyte and catholyte portions of the electrolyte, a power supply connected to the anode(s) and the cathode(s) for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution and the electrolyte is an acid, neutral or alkaline aqueous solution.

11. The apparatus of paragraph 10, wherein:

a. adding stabilizing compounds to the electrolyte such as tellurate or periodate ions which serve to overcome and stabilize the short lifetime of the oxidized form of the higher oxidation state species of the simple and complex anion redox couple mediators;

b. the oxidizer species addressed in this patent are described in Table I (simple anions redox couple mediators);

c. the oxidizer species addressed in this patent are; Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II;

d. the oxidizer species addressed in this patent are combinations mediator species from any or all of these generic groups;

e. the oxidizing species are super oxidizers and further comprising creating secondary oxidizers by reacting the super oxidizers with the aqueous anolyte;

f. an alkaline solution for aiding decomposing the animal waste materials;

g. an alkaline solution for absorbing $CO_2$ and forming alkali metal bicarbonate/carbonate for circulating through the electrochemical cell for producing a percarbonate oxidizer;

h. using oxidizing species from the MEO process inorganic free radicals generated in aqueous solutions derived from carbonate, azide, nitrite, nitrate, phosphite, phosphate, sulfite, sulfate, selenite, thiocyanate, chloride, bromide, iodide, and formate oxidizing species;

i. organic free radicals for aiding the MEO process and breaking down the organic waste materials into simpler (i.e., smaller molecular structure) organic compounds;

j. anions with an oxidation potential above a threshold value of 1.7 volts (i.e., super oxidizer) for involving in a secondary oxidation process for producing oxidizers;

k. the use of Ultrasonic energy induce microscopic bubble implosion which is used to affect a desired reduction in sized of the individual second phase waste volumes dispersed in the anolyte;

l. membrane is ion-selective or semi-permeable (i.e., microporous plastic, ceramic, sintered glass frit, etc.);

m. with the possible impression of an AC voltage upon the DC voltage to retard the formation of cell performance limiting surface films on the electrode; and n. external air is introduced through an air sparge into the catholyte reservoir where oxygen contained in the air oxidizes nitrogen compounds produced by the cathode reactions (this is necessary only when nitrogen compounds can occur in the catholyte).

12. The apparatus of paragraph 10, wherein:

a. each of the oxidizing species has normal valence states (i.e., reduced form of redox couple) and higher valence oxidizing states and further comprising creating the higher valence oxidizing states (i.e., oxidized form of redox couple) of the oxidizing species by stripping and reducing electrons off normal valence state species in the electrochemical cell;

b. using species that are usable in alkaline solutions since oxidation potentials of redox reactions producing hydrogen ions are inversely related to pH which reduces the electrical power required to destroy the animal waste;

c. further oxidizing species, and attacking specific organic molecules with the oxidizing species while operating at temperatures sufficiently low so as to preventing the formation of dioxins and furans;

d. energizing the electrochemical cell at a voltage level sufficient to form the oxidized form of the redox couple having the highest oxidation potential in the anolyte;

e. lower the temperature (e.g. between 0° C. and room temperature) of the anolyte with the heat exchanger before it enters the electrochemical cell to enhance the generation of the oxidized form of the anion redox couple mediator; and f. raise the temperature of the anolyte entering the anolyte reaction chamber with the heat exchanger to affect the desired chemical reactions at the desired rates following the lowering of the temperature of the anolyte entering the electrochemical cell.

13. The apparatus of paragraph 10, wherein:

a. the oxidizing species are one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

b. the oxidizing species are one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

c. the oxidizing species are one or more of any heteropolyanions containing at least one heteroatom type (i.e., element) contained in both Table I and Table II in the aqueous solutions and the electrolyte is an acid, neutral, or alkaline aqueous solution;

d. the oxidizing species are combinations of anion redox couple mediators from any or all of the previous three sub-paragraphs (13a., 13b., 13c);

e. the oxidizing species are higher valence state of species found in situ for destroying the animal waste material; and f. the electrolyte is an acid, neutral, or alkaline aqueous solution.

14. The apparatus of paragraph 10, further comprising:

a. the aqueous solution is chosen from acids such as but not limited to nitric acid, sulfuric acid, or phosphoric acid; alkalines such as but not limited to sodium hydroxide or potassium hydroxide; or neutral electrolytes such as but not limited to sodium or potassium nitrates, sulfates, or phosphates;

b. with a ion-selective or semi-permeable (i.e., microporous plastic, ceramic, sintered glass frit, etc.). membrane for separating the anolyte portion and the catholyte portion while allowing hydrogen or hydronium ion passage from the anolyte to the catholyte;

c. oxidation potentials of redox reactions producing hydrogen ions are inversely related to pH;

d. the animal waste is liquid waste;

e. the animal waste is solid waste e. the animal waste is a combination of liquids and solids and non-animal waste; and f. oxidizing species may be interchanged in a preferred embodiment without changing equipment.

15. The apparatus of paragraph 10, further comprising:

a. a anolyte reaction chamber(s) 5(*b,c*) and buffer tank 20 housing the bulk of the anolyte portion and the foraminous basket 3;

b. a anolyte reaction chamber 5(*a*) housing the bulk of the anolyte portion;

c. a anolyte reaction chamber 5(*d*) and buffer tank 20 housing the bulk of the anolyte portion;

d. an input pump 10 is attached to the anolyte reaction chamber 5(*a*) to enter liquid animal waste into the anolyte reaction chamber 5(*a*);

e. a spray head 4(*a*) and a stream head 4(*b*) attached to the tubing coming from the electrochemical cell 25 that inputs the anolyte containing the oxidizer into the anolyte reaction chamber(s) 5(*a,b,c*) and buffer tank 20 in such a manner as to promote mixing of the incoming anolyte with the anolyte already in the anolyte reaction chambers(s) 5(*a,b,c*);

f. a anolyte reaction chamber(s) 5(*b,c*) houses a foraminous basket 3 with a top that holds solid forms of the animal waste in the electrolyte;

g. a hinged lid 1 attached to the anolyte reaction chamber(s) 5(*a,b,c*) allowing insertion of waste into the anolyte portion as liquid, solid, or a mixture of liquids and solids;

h. the lid 1 contains an locking latch 76 to secure the anolyte reaction chamber(s) 5(*a,b,c*) during operation;

i. a suction pump 8 is attached to buffer tank 20 to pump anolyte to the anolyte reaction chamber(s) 5(*c,d*);

j. an input pump 10 to pump anolyte from the anolyte reaction chamber(s) 5(*c,d*) back into the buffer tank 20; and k. an air pump 32 to pump off gases from the anolyte reaction chamber(s) 5(*c,d*) back into the buffer tank 20 for further oxidation.

16. The apparatus of paragraph 10, further comprising:

a. an ultraviolet source 11 connected to the anolyte reaction chamber(s) 5(*a,b,c*) and buffer tank 20 and decomposing hydrogen peroxide and ozone into hydroxyl free radicals therein and increasing efficiency of the MEO process by recovering energy through the oxidation of the animal waste materials in the anolyte chamber by these secondary oxidizers;

b. an ultrasonic source 9 connected to the anolyte reaction chamber(s) 5(*a,b,c*) and buffer tank 20 for augmenting secondary oxidation processes by heating the hydrogen peroxide containing electrolyte to produce extremely short lived and localized conditions of 4800° C. and 1000 atmospheres pressure within the anolyte to dissociate hydrogen peroxide into hydroxyl free radicals thus increasing the oxidation processes;

c. an ultrasonic energy 9 source connected into the anolyte reaction chamber(s) 5(*a,b,c*) and buffer tank 20 for irradiating cell membranes in animal waste materials by momentarily raising temperature within the cell membranes and causing cell membrane fail and rupture thus creating greater exposure of cell contents to oxidizing species in the anolyte;

d. the use of ultrasonic energy for mixing material in the anolyte, via the ultrasonic energy source 9, to induce microscopic bubble implosion which is used to affect a desired reduction in sized of the individual second phase waste volumes and disperse throughout the anolyte;

e. a mixer 35 for stirring the anolyte connected to the anolyte reaction chamber(s) 5(*a,b,c*) and the buffer tank 20;

f. a $CO_2$ vent 14 for releasing $CO_2$ atmospherically;

g. the penetrator 34 is attached to the basket 3 in anolyte reaction chamber(s) 5(*b,c*) to puncture any solids;

h. an inorganic compounds removal and treatment system 15 connected to the anolyte reaction chamber(s) 5(*a,b,c*) and buffer tank 20 is used should there be more than trace amount of chlorine, or other precipitate forming anions present in the animal waste being processed, thereby precluding formation of unstable oxycompounds (e.g., perchlorates, etc.);

i. an gas cleaning system 16 comprises scrubber/absorption columns;

j. the condenser 13 connected to the anolyte reaction chamber(s) 5(*a,b,c*) and buffer tank 20;

k) non-condensable incomplete oxidation products (e.g., low molecular weight organics, carbon monoxide, etc.) are reduced to acceptable levels for atmospheric release by a gas cleaning system 16;

l. gas cleaning system 16 is not a necessary component of the MEO apparatus for the destruction of most types of animal waste;

m. when the gas cleaning system 16 is incorporated into the MEO apparatus, the anolyte off-gas is contacted in a gas cleaning system 16 wherein the noncondensibles from the condenser 13 are introduced into the lower portion of the gas cleaning system 16 through a flow distribution system and a small side stream of freshly oxidized anolyte direct from the electrochemical cell 25 is introduced into the upper portion of the column, this results in the gas phase continuously reacting with the oxidizing mediator species as it rises up the column past the downflowing anolyte;

n. external drain 12, for draining to the organic compound removal system 17 and the inorganic compounds removal and treatment system 15, and for draining the anolyte system;

o. organic compounds recovery system 17 is used to recover a) organic materials that are benign and do not need further treatment, and b) organic materials that is used in the form they have been reduced and thus would be recovered for that purpose;

p. small thermal control units 21 and 22 are connected to the flow stream to heat or cool the anolyte to the selected temperature range;

q. anolyte is circulated into the anolyte reaction chamber(s) 5(*a,b,c,d*) and buffer tank 20 through the electrochemical cell 25 by pump 19 on the anode 26 side of the membrane 27;

r. a flush(s) 18 for flushing the anolyte and catholyte systems;

s. filter 6 is located at the base of the anolyte reaction chambers 5(*a,b,c,d*) and buffer tank 20 to limit the size of the solid particles to approximately 1 mm in diameter;

t. membrane 27 in the electrochemical cell 25 separates the anolyte portion and catholyte portion of the electrolyte;

u. electrochemical cell 25 is energized by a DC power supply 29, which is powered by the AC power supply 30;

v. DC power supply 29 is low voltage high current supply usually operating below 4 v DC but not limited to that range;

w. AC power supply 29 operates off a typical 110 v AC line for the smaller units and 240 v AC for the larger units;

x. electrolyte containment boundary is composed of materials resistant to the oxidizing electrolyte (e.g., stainless steel, PTFE, PTFE lined tubing, glass, etc.); and y. an electrochemical cell 25 connected to the anolyte reaction chamber(s) 5(*a,b,c*) and buffer tank 20.

17. The apparatus of paragraph 10, wherein:

a. in the anolyte reaction chambers 5(*a,b,c*) and buffer tank 20 is the aqueous acid, alkali, or neutral salt electrolyte and mediated oxidizer species solution in which the oxidizer form of the mediator redox couple initially may be present or may be generated electrochemically after introduction of the waste and application of DC power 29 to the electrochemical cell 25;

b. waste is introduced when the anolyte is at room temperature, operating temperature or some optimum intermediate temperature;

c. DC power supply 29 provides direct current to an electrochemical cell 25;

d. pump 19 circulates the anolyte portion of the electrolyte and the animal waste material is rapidly oxidized at temperatures below 100° C. and ambient pressure;

e. in-line filter 6 prevents solid particles large enough to clog the electrochemical cell 25 flow paths from exiting this reaction chambers 5(*a,b,c,d*) and buffer tank 20;

f. residue is pacified in the form of a salt and may be periodically removed through the Inorganic Compound Removal and Treatment System 15 and drain outlets 12;

g. electrolyte may be changed through this same plumbing for introduction into the reaction chambers 5(*a,b,c*) and buffer tank 20 and 31;

h. the process operates at low temperature and ambient atmospheric pressure and does not generate toxic compounds during the destruction of the animal waste, making the process indoors compatible;

i. the system is scalable to a unit large for a large industrial application; and j. $CO_2$ oxidation product from the anolyte system A is vented out the $CO_2$ vent 14.

18. The apparatus of paragraph 10, wherein:

a. an anolyte recovery system 41 connected to the catholyte pump (43);

b. a thermal control unit 45 connected to the catholyte reservoir for varying the temperature of the catholyte portion;

c. a catholyte reservoir 31 connected to the cathode portion of the electrochemical cell;

d. bulk of the catholyte is resident in the catholyte reaction chamber 31;

e. catholyte portion of the electrolyte flows into a catholyte reservoir 31;

f. an air sparge 37 connected to the catholyte reservoir 31 for introducing air into the catholyte reservoir 31;

g. an anolyte recovery system 41 for capturing the anions and for reintroducing the anions into the anolyte chamber(s) 5(a,b,c) and buffer tank 20 or disposal from the catholyte electrolyte;

h. an off gas cleaning system 39 for cleaning gases before release into the atmosphere connected to the catholyte reservoir 31;

i. an atmospheric vent 47 for releasing gases into the atmosphere connected to the off gas cleaning system 39;

j. cleaned gas from the off gas cleaning system 39 is combined with unreacted components of the air introduced into the system and discharged through the atmospheric vent 47;

k. a catholyte reservoir 31 has a screwed top 33 (shown in FIG. 1A), which allow access to the reservoir 31 for cleaning and maintenance by service personnel;

l. a mixer 35 for stirring the catholyte connected to the catholyte reservoir 31;

m. a catholyte pump 43 for circulating catholyte back to the electrochemical cell 25 connected to the catholyte reservoir 31;

n. a drain 12 for draining catholyte;

o. a flush 18 for flushing the catholyte system;

p. an air sparge 37 connected to the housing for introducing air into the catholyte reaction chamber 31;

q. catholyte portion of the electrolyte is circulated by pump 43 through the electrochemical cell 25 on the cathode 28 side of the membrane 27;

r. small thermal control units 45 and 46 are connected to the catholyte flow stream to heat or cool the catholyte to the selected temperature range;

s. contact of the oxidizing gas with the catholyte electrolyte may be enhanced by using conventional techniques for promoting gas/liquid contact by a ultrasonic vibration 48, a mechanical mixer 35, etc.;

t. operating the electrochemical cell 25 at higher than normal membrane 27 current densities (i.e., above about 0.5 amps/cm$^2$) will increase the rate of waste destruction, but also result in increased mediator ion transport through the membrane into the catholyte;

u. optional anolyte recovery system 41 is positioned on the catholyte side;

v. systems using non-nitric acid catholytes may also require air sparging to dilute and/or remove off-gas such as hydrogen;

w. some mediator oxidizer ions may cross the membrane 27 and this option is available if it is necessary to remove them through the anolyte recovery system 41 to maintain process efficiency or cell operability, or their economic worth necessitates their recovery;

x. using the anolyte recovery system 41 the capitol cost of expanding the size of the electrochemical cell 25 can be avoided; and y. operating the electrochemical cell 25 at higher than normal membrane current density (i.e., above about 0.5 amps per centimeter squared) improves economic efficiency.

19. The apparatus of paragraph 10, wherein:

a. operator runs the MEO Apparatus (FIG. 1A) and FIG. 1B by using the MEO Controller depicted in FIG. 2 MEO Controller;

b. controller 49 with microprocessor is connected to a monitor 51 and a keyboard 53;

c. operator inputs commands to the controller 49 through the keyboard 53 responding to the information displayed on the monitor 51;

d. controller 49 runs a program that sequences the steps for the operation of the MEO apparatus;

e. program has pre-programmed sequences of standard operations that the operator may follow or may choose his own sequences of operations;

f. controller 49 allows the operator to select his own sequences within limits that assure a safe and reliable operation;

g. controller 49 sends digital commands that regulates the electrical power (AC 30 and DC 29) to the various components in the MEO apparatus: pumps 19 and 43, mixers 7 and 35, thermal controls 21, 22, 45, 46, heat exchangers 23 and 24, ultraviolet sources 11, ultrasonic sources 9 and 48, $CO_2$ vent 14, air sparge 37, and electrochemical cell 25;

h. controller receives component response and status from the components;

i. controller sends digital commands to the sensors to access sensor information through sensor responses;

j. sensors in the MEO apparatus provide digital information on the state of the various components;

k. sensors measure flow rate 59, temperature 61, pH 63, $CO_2$ venting 65, degree of oxidation 67, air sparge sensor 69, etc; and l. controller 49 receives status information on the electrical potential (voltmeter 57) across the electrochemical cell or individual cells if a multi-cell configuration and between the anode(s) and reference electrodes internal to the cell(s) 25 and the current (ammeter 55) flowing between the electrodes within each cell.

20. The apparatus of paragraph 10, wherein:

a. preferred embodiment, MEO System Model 5.b is sized for use in a small to mid-size application; other preferred embodiments have differences in the external configuration and size but are essentially the same in internal function and components as depicted in FIGS. 1B, 1D, and 1E;

b. preferred embodiment in FIG. 3 comprises a housing 72 constructed of metal or high strength plastic surrounding the electrochemical cell 25, the electrolyte and the foraminous basket 3;

c. AC power is provided to the AC power supply 30 by the power cord 78;

d. monitor screen 51 is incorporated into the housing 72 for displaying information about the system and about the waste being treated;

e. control keyboard 53 is incorporated into the housing 72 for inputting information into the system;

f. monitor screen 51 and the control keyboard 53 may be attached to the system without incorporating them into the housing 72;

g. system model 5.b has a control keyboard 53 for input of commands and data;

h. monitor screen 51 to display the systems operation and functions;

i. status lights 73 for on, off and standby, are located above the keyboard 53 and monitor screen 51;

j. in a preferred embodiment, status lights 73 are incorporated into the housing 72 for displaying information about the status of the treatment of the animal waste material;

k. air sparge 37 is incorporated into the housing 72 to allow air to be introduced into the catholyte reaction chamber 31 below the surface of the catholyte;

l. a $CO_2$ vent 14 is incorporated into the housing 72 to allow for $CO_2$ release from the anolyte reaction chamber housed within;

m. in a preferred embodiment, the housing includes means for cleaning out the MEO waste treatment system, including a flush(s) 18 and drain(s) 12 through which the anolyte and catholyte pass;

n. the preferred embodiment further comprises an atmospheric vent 47 facilitating the releases of gases into the atmosphere from the catholyte reaction chamber 31;

o. hinged lid 1 is opened and the solid animal waste is deposited in the basket 3 in the chamber 5(b);

p. lid stop 2 keeps lid opening controlled; and q. hinged lid 1 is equipped with a locking latch 76 that is operated by the controller 49.

21. The apparatus of paragraph 10, wherein:

a. MEO apparatus is contained in the housing 72;

b. MEO system is started 81 by the operator engaging the 'ON' button 74 on the control keyboard 53;

c. system controller 49, which contains a microprocessor, runs the program that controls the entire sequence of operations 82;

d. monitor screen 51 displays the steps of the process in the proper sequence;

e. status lights 73 on the panel provide the status of the MEO apparatus (e.g. on, off, ready, standby);

f. lid 1 is opened and the animal waste is placed 83 in the anolyte reaction chamber 5(b) in basket 3 as a liquid, solid, or a mixture of liquids and solids, whereupon the solid portion of the waste is retained and the liquid portion flows through the basket and into the anolyte;

g. locking latch 76 is activated after waste is placed in basket;

h. pumps 19 and 43 are activated which begins circulation 85 of the anolyte 87 and catholyte 89, respectively;

i. once the electrolyte circulation is established throughout the system, the mixers 7 and 35 begin to operate 91 and 93;

j. depending upon waste characteristics (e.g., reaction kinetics, heat of reaction, etc.) it may be desirable to introduce the waste into a room temperature or cooler system with little or none of the mediator redox couple in the oxidizer form;

k. once flow is established the thermal controls units 21, 22, 45, and 46 are turned on 95/97, initiating predetermined anodic oxidation and electrolyte heating programs;

l. the electrochemical cell 25 is energized 94 (by cell commands 56) to the electric potential 57 and current 55 density determined by the controller program;

m. by using programmed electrical power and electrolyte temperature ramps it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions;

n. the ultrasonic sources 9 and 48 and ultraviolet systems 11 are activated 99 and 101 in the anolyte reaction chambers 5(a,b,c) and buffer tank 20 and catholyte reaction chamber 31 if those options are chosen in the controller program;

o. $CO_2$ vent 14 is activated 103 to release $CO_2$ from the animal waste oxidation process in the anolyte reaction chambers 5(a,b,c) and buffer tank 20;

p. air sparge 37 and atmospheric vent 47 are activated 105 in the catholyte system;

q. progress of the destruction process is monitored in the controller (oxidation sensor 67) by various cell voltages and currents 55, 57 (e.g., open circuit, anode vs. reference electrode, ion specific electrodes, etc,) as well as monitoring $CO_2$, CO, and $O_2$ gas 65 composition for $CO_2$, CO and oxygen content;

r. animal waste is being decomposed into water and $CO_2$ the latter being discharged 103 out of the $CO_2$ vent 14;

s. air sparge 37 draws air 105 into the catholyte reservoir 31, and excess air is discharged out the atmospheric vent 47;

t. when the oxidation sensor 67 determine the desired degree of waste destruction has been obtained 107, the system goes to standby 109;

u. MEO apparatus as an option may be placed in a standby mode with animal waste being added as it is generated throughout the day and the unit placed in full activation during non-business hours; and v. system operator executes system shutdown 111 using the controller keyboard 53.

TABLE I

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species |
| | | | | $HCuO_2$ (bicuprite) | +3 Species/+4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^1$ (argentous) | +1 Species/+2, +3 Species |
| | | | | $AgO^-$ (argentite) | +2 Species/+3 Species |
| | | | +2 | $Ag^{-2}$ (argentic) | |
| | | | | AgO (argentic oxide) | |
| | | | +3 | $AgO^1$ (argentyl) | |
| | | | | $Ag_2O_3$ (sesquioxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Gold (Au) | +1 | $Au^1$ (aurous) | +1 Species/+3, +4 Species |
| | | | +3 | $Au^{+3}$ (auric) | +3 Species/+4 Species |
| | | | | $AuO^-$ (auryl) | |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^2$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{-2}$ (zincic) | +2 Species/+4 Species |
| | | | | $ZnOH^1$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/+4 Species |
| | | | | $Hg(OH)_2$ (mercuric hydroxide) | |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/+4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^{-}/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O^{-2}$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/+3 or +3.33 Species |
| | | | +3 | $Tl^3$ (thallic) | +3 Species/+3.33 Species |
| | | | | $T^+$, $TlOH^{+2}$, $Tl(OH)_2^+$ (thallyl) | |
| | | | | $Tl_2O_3$ (sesquioxide) | |
| | | | | $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/+5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/+6 Species |
| | | | | $HGeO_3^-$ (bigermaniate) | |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/+7 Species |
| | | | | $HSnO_3^-$ (bistannate) | |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4$ (perstannate) | |
| | | Lead (Pb) | +2 | $Pb^{+2}$ (plumbous) | +2, +2.67, +3 Species/+4 Species |
| | | | | $HPbO_2^-$ (biplumbite) | |
| | | | | $PbOH+$ | |
| | | | | $PbO_2^{-2}$ (plumbite) | |
| | | | | $PbO$ (plumbus oxide) | |
| | | | +2.67 | $Pb_3O_4$ (plumbo-plumbic oxide) | |
| | | | +3 | $Pb_2O_3$ (sequioxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
|  | B | Titanium | +4 | $TiO^{+2}$ (pertitanyl)<br>$HTiO_4^-$ (titanate)<br>$TiO_2$ (dioxide) | +4 Species/+6 Species |
|  |  |  | +6 | $TiO_2^{+2}$ (pertitanyl)<br>$HTiO_4^-$ (acid pertitanate)<br>$TiO_4^{-2}$ (pertitanate)<br>$TiO_3$ (peroxide) |  |
|  |  | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
|  |  |  | +5 | $Zr_2O_5$ (pentoxide) |  |
|  |  |  | +6 | $ZrO_3$ (peroxide) |  |
|  |  |  | +7 | $Zr_2O_7$ (heptoxide) |  |
|  |  | Hafnium (Hf) | +4 | $Hf^{-4}$ (hafnic)<br>$HfO^{+2}$ (hafnyl) | +4 Species/+6 Species |
|  |  |  | +6 | $Hfo_3$ (peroxide) |  |
| V | A | Nitrogen | +5 | $HNO_3$ (nitric acid)<br>$NO_3^-$ (nitrate) | +5 species/+7 Species |
|  |  |  | +7 | $HNO_4$ (pernitric acid) |  |
|  |  | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
|  |  |  | +7 | $H_3PO_5$ (monoperphosphoric acid) |  |
|  |  | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
|  |  |  | +7 | $AsO_3^+$ (perarsenyl) |  |
|  |  | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/+3.5, +4, +5 Species |
|  |  |  | +3.5 | $Bi_4O_7$ (oxide) |  |
|  |  |  | +4 | $Bi_2O_4$ (tetroxide) |  |
|  |  |  | +5 | $BiO_3^-$ (metabismuthite)<br>$Bi_2O_5$ (pentoxide) |  |
|  | B | Vanadium (V)<br>(See also POM<br>Complex Anion<br>Mediators) | +5 | $VO_2^-$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | +5 Species/+7, +9 Species |
|  |  |  | +7 | $VO_4^-$ (pervanadate) |  |
|  |  |  | +9 | $VO_5^-$ (hypervanadate) |  |
| V | B | Niobium (Nb)<br>(See also POM<br>Complex Anion<br>Mediators) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |
|  |  |  | +7 | $NbO_4^-$ (perniobate)<br>$Nb_2O_7$ (perniobic oxide)<br>$HNbO_4$ (perniobic acid) |  |
|  |  | Tantalum (Ta)<br>(See also POM<br>Complex Anion<br>Mediators) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7 species |
|  |  |  | +7 | $TaO_4^-$ (pentantalate)<br>$Ta_2O_7$ (pertantalate)<br>$HTaO_4 \cdot H_2O$ (pertantalic acid) |  |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| VI | A | Sulfur (S) | +6 | $H_2SO_4$ (sulfuric acid) $HSO_4^-$ (bisulfate) $SO_4^{-2}$ (sulfate) | +6 Species/+7, +8 Species |
| | | | +7 | $S_2O_8^-$ (dipersulfate) | |
| | | | +8 | $H_2SO_5$ (momopersulfuric acid) | |
| | | Selenium (Se) | +6 | $H_2Se_2O_4$ (selenic acid) $HSeO_4^-$ (biselenate) $SeO_4^{-}2$ (selenate) | +6 species/+7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}, Cr(OH)_2^+$ (chromyls) $CrO_2^-, CrO_3^{-3}$ (chromites) $Cr_2O_3$ (chromic oxide) $Cr(OH)_3$ (chromic hydroxide) | +3 Species/+4, +6 Species +4 Species/+6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) (See also POM Complex Anion Mediators) | +6 | $HMoO_4^-$ (bimolybhate) $MoO_4^{-2}$ (molydbate) $MoO_3$ (molybdic trioxide) $H_2MoO_4$ (molybolic acid) | +6 Species/+7 Species |
| | | | +7 | $MoO_4^-$ (permolybdate) | |
| | | Tungsten (W) (See also POM Complex Anion Mediators) | +6 | $WO_4^{-2}$ tungstic) $WO_3$ (trioxide) $H_2WO_4$ (tungstic acid) | +6 Species/+8 Species |
| | | | +8 | $WO_5^{-2}$ (pertungstic) $H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid) $ClO^-$ (hypochlorite) | +1 Species/+3, +5, +7 Species +3 Species/+5, +7 Species |
| | | | +3 | $HClO_2$ (chlorous acid) $ClO_2^-$ (chlorite) | +5 Species/+7 Species |
| | | | +5 | $HClO_3$ (chloric acid) $ClO_3^-$ (chlorate) | |
| | | | +7 | $HClO_4$ (perchloric acid) $ClO_4^-, HClO_5^{-2}, ClO_5^{-3}, Cl_2O_9^{-4}$ (perchlorates) | |
| VII | A | Bromine (Br) | −1 | Br (bromide) | −1 Species/+1, +3, +5, +7 Species |
| | | | +1 | HBrO (hypobromous acid) $BrO^-$ (hypobromitee) | +1 Species/+3, +5, +7 Species +3 Species/+5, +7 Species |
| | | | +3 | $HBrO_2$ (bromous acid) $BrO2^-$ (bromite) | +5 Species/+7 Species |
| | | | +5 | $HBrO_3$ (bromic acid) $BrO_3^-$ (bromate) | |
| | | | +7 | $HBrO_4$ (perbromic acid) $BrO_4^-, HBrO_5^{-2}, BrO_5^{-3}, Br_2O_9^{-4}$ (prebromates) | |
| | | Iodine | −1 | $I^-$ (iodide) | −1 Species/+1, +3, +5, +7 Species |
| | | | +1 | HIO (hypoiodus acid) $IO^-$ (hypoiodite) | +1 Species/+3, +5, +7 Species +3 Species/+5, +7 Species |
| | | | +3 | $HIO_2$ (iodous acid) $IO_2^-$ (iodite) | +5 Species/+7 Species |
| | | | +5 | $HIO_3$ (iodic acid) $IO_3^-$ (iodate) | |
| | | | +7 | $HIO_4$ (periodic acid) $IO_4^-, HIO_5^{-2}, IO_5^{-3}, I_2O_9^{31\ 4}$ (periodates) | |
| | B | Manganese (Mn) | +2 | $Mn^{+2}$ (manganeous) $HMnO_2^-$ (dimanganite) | +2 Species/+3, +4, +6, +7 Species +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| VIII | Period 4 | Iron (Fe) | +2 | $Fe^{+2}$ (ferrous) | +2 Species/+3, +4, +5, +6 Species |
| | | | | $HFeO_2^-$ (dihypoferrite) | +3 Species/+4, +5, +6 Species |
| | | | +3 | $Fe^{+3}$, $FeOH^{+2}$, $Fe(OH)_{2+}$ (ferric) | +4 Species/+5, +6 Species |
| | | | | $FeO_2^-$ (ferrite) | +5 Species/+6 Species |
| | | | +4 | $FeO^{+2}$ (ferryl) | |
| | | | | $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) | +2 Species/+3, +4 Species |
| | | | | $HCoO_2^-$ (dicobaltite) | +3 Species/+4 Species |
| | | | +3 | $Co^{+3}$ (cobaltic) | |
| | | | | $Co_2O_3$ (cobaltic oxide) | |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, +4, +6 Species |
| | | | | $NiOH^+$ | +3 Species/+4, +6 Species |
| | | | | $HNiO_2^-$ (dinickelite) | +4 Species/+6 Species |
| | | | | $NiO_2^{-2}$ (nickelite) | |
| | | | +3 | $Ni^{+3}$ (nickelic) | |
| | | | | $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species |
| | | | +3 | $Ru^{+3}$ | +3 Species/+4, +5, +6, +7, +8 Species |
| | | | | $Ru_2O_3$ (sesquioxide) | +4 Species/+5, +6, +7, +8 Species |
| | | | | $Ru(OH)_3$ (hydroxide) | +5 Species/+6, +7, +8 Species |
| | | | +4 | $RU^{+4}$ ruthenic) | +6 Species/+7, +8 Species |
| | | | | $RuO_2$ (ruthenic dioxide) | +7 Species/+8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) | |
| | | | | $RuO_2^{+2}$ (ruthenyl) | |
| | | | | $RuO_3$ (trioxide) | |
| | | | +7 | $RuO_4^-$ (perruthenate) | |
| | | | +8 | $H_2RuO_4$ (hyperuthenic acid) | |
| | | | | $HRuO_5^-$ (diperruthenate) | |
| | | | | $RuO_4$ (ruthenium tetraxide) | |
| | | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) | +3 Species/+4, +6 Species |
| | | | | $Rh_2O_3$ (sesquioxide) | +4 Species/+6 Species |
| | | | +4 | $RhO_2$ (rhodic oxide) | |
| | | | | $Rh(OH)_4$ (hydroxide) | |
| | | | +6 | $RhO_4^{-2}$ (rhodate) | |
| | | | | $RhO_3$ (trioxide) | |
| | | Palladium | +2 | $Pd^{+2}$ (palladous) | +2 Species/+3, +4, +6 Species |
| | | | | $PdO_2^{-2}$ (palladite) | +3 Species/+4, +6 Species |
| | | | +3 | $Pd_2O_3$ (sesquioxide) | +4 Species/+6 Species |
| | | | +4 | $PdO_3^{-2}$ (palladate) | |
| | | | | $PdO_2$ (dioxide) | |
| | | | | $Pd(OH)_4$ (hydroxide) | |
| | | | +6 | $PdO_3$ (peroxide) | |
| VIII | Period 6 | Iridium (Ir) | +3 | $Ir^{+3}$ (iridic) | +3 Species/ +4, +6 Species |
| | | | | $Ir_2O_3$ (iridium sesquioxide) | +4 Species/+6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}$, $Ce(OH)^{+3}$, $Ce(OH)_2^{+2}$, | |
| | | | | $Ce(OH)_3^+$ (ceric) | |
| | | | | $CeO_2$ (ceric oxide) | |
| | | | +6 | $CeO_3$ (peroxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Praseodymium (Pr) | +3 | $Pr^{+3}$ (praseodymous) $Pr_2O_3$ (sesquioxide) $Pr(OH)_3$ (hydroxide) | +3 species/+4 species |
| | | | +4 | $Pr^{+4}$ (praseodymic) $PrO_2$ (dioxide) | |
| | | Neodymium | +3 | $Nd^{+3}$ $Nd_2O_3$ (sesquioxide) | +3 Species/+4 Species |
| | | | +4 | $NdO_2$ (peroxide) | |
| | | Terbium (Tb) | +3 | $Tb^{+3}$ $Tb_2O_3$ (sesquioxide) | +3 Species/+4 Species |
| | | | +4 | $TbO_2$ (peroxide) | |
| IIIB | Actinides | Thorium (Th) | +4 | $Th^{+4}$ (thoric) $ThO^{+2}$ (thoryl) $HThO^-$ (thorate) | +4 Species/+6 Species |
| | | | +6 | $ThO_3$ (acid peroxide) | |
| | | Uranium (U) | +6 | $UO_2^{+2}$ (uranyl) $UO_3$ (uranic oxide) | +6 Species/+8 Species |
| | | | +8 | $HUO_5^{-2}$ $UO_5^{-2}$ (peruranates) $UO_4$ (peroxide) | |
| | | Neptunium (Np) | +5 | $NpO_2^-$ (hyponeptunyl) $Np_2O_5$ (pentoxide) | +5 Species/+6, +8 Species +6 Species/+8 Species |
| | | | +6 | $NpO_2^{+2}$ (neptunyl) $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) $PuO_2$ (dioxide) | +4 Species/+5, +6 Species +5 Species/+6 Species |
| | | | +5 | $PuO_2^+$ (hypoplutonyl) $Pu_2O_5$ (pentoxide) | |
| | | | +6 | $PuO_2^{+2}$ (plutonyl) $PUO_3$ (peroxide) | |
| | | Americium (Am) | +3 | $Am^{+3}$ (hypoamericious) | |
| | | | +4 | $Am^{+4}$ (americous) $AmO_2$ (dioxide) $Am(OH)_4$ (hydroxide) | |
| | | | +5 | $AmO_2^+$ (hypoamericyl) $Am_2O_5$ (pentoxide) | |
| | | | +6 | $AmO_2^{+2}$ (americyl) $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All |

We claim:

1. A process for treating and oxidizing animal waste materials comprising disposing an electrolyte in an electrochemical cell, separating the electrolyte into an anolyte portion and a catholyte portion with an ion-selective membrane or semipermeable membrane applying a direct current voltage between the anolyte portion and the catholyte portion, placing the animal waste materials in the anolyte portion, and oxidizing the animal waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, further comprising introducing an ultrasonic energy into the anolyte portion, rupturing cell membranes of biological cells in the animal waste materials by momentarily raising local temperature within the biological cells with the ultrasonic energy to above several thousand degrees, and causing cell membrane failure.

2. The process of claim 1, wherein the membrane is an ion-selective membrane, or semi permeable membrane, microporous polymer membrane, porous ceramic membrane, or glass frit.

3. A process for treating and oxidizing animal waste materials comprising disposing an electrolyte in an electrochemical cell, separating the electrolyte into an anolyte portion and a catholyte portion with an ion-selective membrane or semi-permeable membrane applying a direct current voltage between the anolyte portion and the catholyte portion, placing the animal waste materials in the anolyte portion, and oxidizing the animal waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, further comprising adding a surfactant to the anolyte portion for promoting dispersion of the animal waste materials or intermediate stage reaction products within the aqueous solution when the animal waste materials or reaction products are not water-soluble and tend to form immiscible layers.

4. The process of claim 3, wherein the membrane is an ion-selective membrane, or semi permeable membrane, microporous polymer membrane, porous ceramic membrane, or glass frit.

5. A process for treating and oxidizing animal waste, comprising circulating ions of mediator oxidizing species in an electrolyte through an electrochemical cell and affecting anodic oxidation of reduced forms of reversible redox couples into oxidized forms, contacting the ions with the animal waste in an anolyte portion of the electrolyte in a primary oxidation process, involving superoxidizer ions, having an oxidation potential above a threshold value of 1.7 volts at 1 molar, 25° C. and pH1, wherein when said superoxidizers are present there is a free radical oxidizer driven secondary oxidation process, adding energy from an energy source to the anolyte portion and augmenting the secondary oxidation processes, breaking down hydrogen peroxide and ozone in the anolyte portion into hydroxyl free radicals, and increasing an oxidizing effect of the secondary oxidation processes, wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| 1 | A | None | | | |
| | B | Copper (Cu) | +2 | $Cu^{-2}$ (cupric) | +2 Species/+3, +4 |
| | | | | $HCuO_2^-$ (bicuprite) | Species; |
| | | | | $CuO_2^{-2}$ (cuprite) | +3 Species/+4 Species |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^+$ (argentous) | +1 Species/+2, +3 |
| | | | | $AgO^-$ (argentite) | Species; |
| | | | +2 | $Ag^{-2}$ (argentic) | +2 Species/+3 Species |
| | | | | AgO (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/+3, +4 |
| | | | +3 | $Au^{+3}$ (auric) | Species; |
| | | | | $AuO^-$ (auryl) | +3 Species/+4 Species |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/ +4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| II | B | Zinc (Zn) | +2 | $Zn^{+2}$ (zincic)<br>$ZnOH^+$ (zincyl)<br>$HZnO_2^-$ (bizincate)<br>$ZnO_2^{-2}$ (zincate) | +2 Species/<br>+4 Species |
| | | | +4 | $ZnO_2$ (peroxide) | |
| | | Mercury (Hg) | +2 | $Hg^{+2}$ (mercuric)<br>$Hg(OH)_2$ (mercuric hydroxide)<br>$HHgO_2^-$ (mercurate) | +2 Species/<br>+4 Species |
| | | | +4 | $HgO_2$ (peroxide) | |
| III | A | Boron | +3 | $H_3BO_3$ (orthoboric acid)<br>$H_2BO_3^-$, $HBO_3^{-2}$, $BO_3^{-3}$ (orthoborates)<br>$BO_2^-$ (metaborate)<br>$H_2B_4O_7$ (tetraboric acid)<br>$HB_4O_7^-/B_4O_7^{-2}$ (tetraborates)<br>$B_2O_4^{-2}$ (diborate)<br>$B_6O_{10}^{-2}$ (hexaborate) | +3 Species/<br>+4.5, 5 Species |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/<br>+3 or +3.33 Species;<br>+3 Species/<br>+3.33 Species |
| | | | +3 | $Tl^{+3}$ (thallic)<br>$TlO^+$, $TlOH^{+2}$, $Tl(OH)_2^+$ (thallyl)<br>$Tl_2O_3$ (sesquioxide)<br>$Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid)<br>$HCO_3^-$ (bicarbonate)<br>$CO_3^{-2}$ (carbonate) | +4 Species/<br>5, +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid)<br>$HGeO_3^-$ (bigermaniate)<br>$GeO_3^{-4}$ (germinate)<br>$Ge_4^{+4}$ (germanic)<br>$GeO_4^{-4}$<br>$H_2Ge_2O_5$ (digermanic acid)<br>$H_2Ge_4O_9$ (tetragermanic acid)<br>$H_2Ge_5O_{11}$ (pentagermanic acid)<br>$HGe_5O_{11}^-$ (bipentagermanate) | +4 Species/<br>+6 Species |
| | | | +6 | $Ge_5O_{11}^-$ (pentagermanate) | |
| | | Tin (Sn) | +4 | $Sn^{+4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/<br>+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^-$ (plumbite)<br>$PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| IV | B | Titanium | +4 | $TiO^{+2}$ (pertitanyl)<br>$HTiO_4^-$ titanate)<br>$TiO_2$ (dioxide) | +4 Species/<br>+6 Species |
| | | | +6 | $TiO_2^{+2}$ (pertianyl)<br>$HTiO_4^-$ (acid pertitanate)<br>$TiO_4^{-2}$ (pertitanate)<br>$TiO_3$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/+6 Species |
| | | | +6 | $HfO_3$ (peroxide) | |
| V | A | Nitrogen | +5 | $HNO_3$ (nitric acid)<br>$NO_3^-$ (nitrate) | +5 species/+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
| | | | +7 | $H_3PO_5$ (monoperphosphoric acid) | |
| V | A | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | 5 Species/+7, +9 Species |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |
| | | | +7 | $NbO_4^-$ (perniobate)<br>$Nb_2O_7$ (perniobic acid)<br>$HNbO_4$ (perniobic acid) | |
| | | Tantalum (Ta) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7 species |
| | | | +7 | $TaO_4^-$ (pentantalate)<br>$Ta_2O_7$ (pertantalate)<br>$HTaO_4 \cdot H_2O$ (pertantalic acid) | |
| VI | A | Sulfur (S) | +6 | $H_2SO_4$ (sulfuric acid)<br>$HSO_4^-$ (bisulfate)<br>$SO_4^{-2}$ (sulfate) | +6 Species/+7, +8 Species |
| | | | +7 | $S_2O_8^{-2}$ (sulfate) | |
| | | | +8 | $H_2SO_5$ (momopersulfuric acid) | |
| | | Selenium (Se) | +6 | $H_2Se_2O_4$ (selenic acid)<br>$HSeO_4^-$ (biselenate)<br>$HSeO_4^-$ (biselenate)<br>$SeO_4^{-2}$ (selenate) | +6 species/+7 Species |
| | | | +7 | $H_2Se_2O_8$ (perdiselenic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tellurium (Te) | +6 | $H_2TeO_4$ (tellenic acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/ +4, +6 Species; +4 Species/ +6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/ +7 Species |
| | | | +7 | $MoO_4^-$ (permolybdate) | |
| | | Tungsten (W) | +6 | $WO_4^{-2}$ tungstic $WO_3$ (trioxide) $H_2WO_4$ (tungstic acid) | +6 Species/ +8 Species |
| | | | +8 | $WO_4^{-2}$ (pertungstic) $H_2WO_5$ (pertungstic acid) | |
| VII | A | Chlorine (Cl) | +1 | HClO (hypochlorous acid) $ClO^-$ (hypochlorite) | +1 Species/ +3, +5, +7 Species; |
| | | | +3 | $HClO_2$ (chlorous acid) $ClO_2^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid) $BrO^-$ (hypobromitee) | +1 Species/+3, +5, +7 Species; |
| | | | +3 | $HBrO_2$ (bromous acid) $BrO2^-$ (bromite) | +3 Species/+5, +7 Species; |
| | | | +5 | $HBrO_3$ (bromic acid) $BrO_3^-$ (bromate) | +5 Species/+7 Species |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | +1 | HIO (hypoiodus acid) $IO^-$ (hypoiodite) | +1 Species/+3, +5, +7 Species; |
| | | | +3 | $HIO_2$ (iodous acid) $IO_2^-$ (iodite) | +3 Species/+5, +7 Species; |
| | | | +5 | $HIO_3$ (iodic acid) $IO_3^-$ (iodate) | +5 Species/+7 Species |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species; |
| | | | +3 | $Mn^{+3}$ (manganic) | |
| | | | +4 | $MnO_2$ (dioxide) | +3 Species/+4, +6, +7 Species; |
| | | | +6 | $MnO_4^{-2}$ (manganate) | +4 Species/+6, +7 Species; |
| | | | +7 | $MnO_4^-$ (permanganate) | +6 Species/+7 Species |
| VIII | Period 4 | Iron (Fe) | +3 | $FeO^{+3}$ (ferric) $Fe(OH)^{+2}$ $Fe(OH)_2^+$ $FeO_2^{-2}$ (ferrite) | +3 Species/+4, +5, +6 Species; +4 Species/ +5, +6 Species; |
| VIII | Period 4 | Iron (Fe) | +4 | $FeO^{+2}$ (ferryl) $FeO_2^{-2}$ (perferrite) | +5 Species/ +6 Species |
| | | | +5 | $FeO_2^+$ (perferryl) | |
| | | | +6 | $FeO_4^{-2}$ (ferrate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Cobalt (Ca) | +2 | $Co^{+2}$ (cobalous) | +2 Species/ |
| | | | | $HCoO_2^-$ (dicobaltite) | +3, +4 Species; |
| | | | +3 | $Co^{+3}$ (cobaltic) | +3 Species/ |
| | | | | $Co_2O_3$ (cobaltic oxide) | +4 Species |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, |
| | | | | $NiOH^+$ | +4, +6 Species; |
| | | | | $HNiO_2^-$ (dinickelite) | +3 Species/ |
| | | | | $NiO_2^{-2}$ (nickelite) | +4, +6 Species; |
| | | | +3 | $Ni^{+3}$ (nickelic) | +4 Species/ |
| | | | | $Ni_2O_3$ (nickelic oxide) | +6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3 |
| | | | +3 | $Ru^{+3}$ | +4, +5, +6, +7, |
| | | | | $Ru_2O_3$ (sesquioxide) | +8 Species; |
| | | | | $Ru(OH)_3$ (hydroxide) | +3 Species/+4, |
| | | | +4 | $Ru^{+4}$ (ruthenic) | +5, +6, +7, +8 |
| | | | | $RuO_2$ (ruthenic dioxide) | Species; |
| | | | | $Ru(OH)_4$ (ruthenic hydroxide) | +4 Species/ |
| | | | +5 | $Ru_2O_5$ (pentoxide) | +5, +6, +7, +8 |
| | | | +6 | $RuO_4^{-2}$ (ruthenate) | Species; |
| | | | | $RuO_2^{+2}$ (ruthenyl) | +5 Species/+6, |
| | | | | $RuO_3$ (trioxide) | +7, +8 Species; |
| | | | +7 | $RuO_4^-$ (perruthenate) | +6 Species |
| | | | +8 | $H_2RuO_4$ (hyperuthenic acid) | +7, +8 Species; |
| | | | | $HRuO_5^-$ (diperruthenate) | +7 Species/ |
| | | | | $RuO_4$ (ruthenium tetroxide) | +8 Species |
| | | Rhodium (Rh) | +1 | $Rh^+$ (hyporhobus) | +1 Species/+2, |
| | | | +2 | $Rh^{+2}$ (rhodous) | +3, +4, +6 |
| | | | +3 | $Rh^{+3}$ (rhodic) | Species; |
| | | | | $Rh_2O_3$ (sesquioxide) | +2 Species/+3, |
| | | | +4 | $RhO_2$ (rhodic oxide) | +4, +6 Species; |
| | | | | $Rh(OH)_4$ (hydroxide) | +3 Species/+4, |
| | | | +6 | $RhO_4^{-2}$ (rhodate) | +6 Species; |
| | | | | $RhO_3$ (trioxide) | +4 Species/+6 Species |
| | | Palladium | +2 | $Pd^{+2}$ (palladous) | +2 Species/+3, |
| | | | | $PdO_2^{-2}$ (palladite) | +4, +6 Species; |
| | | | +3 | $Pd_2O_3$ (sesquioxide) | +3 Species/ |
| | | | +4 | $PdO_3^{-2}$ (palladate) | +4, +6 Species; |
| | | | | $PdO_2$ (dioxide) | +4 Species/ |
| | | | | $Pd(OH)_4$ (hydroxide) | +6 Species |
| | | | +6 | $PdO_3$ (peroxide) | |
| VIII | Period 6 | Iridium (Ir) | +3 | $Ir^{+3}$ (iridic) | +3 Species/ |
| | | | | $Ir_2O_3$ (iridium sesquioxide) | +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| | | | +6 | $PtO_4^{-2}$ (Perplatinate) | |
| | | | | $PtO_3$ (perplatinix oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}$, $Ce(OH)^{+3}$, $Ce(OH)_2^{+2}$, | +6 Species |
| | | | | $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species; |
| | | | | $Np_2O_5$ (pentoxide) | |
| | | | +6 | $NpO_2^{+2}$ (neptunyl) | +6 Species/+8 Species |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) | +4 Species/+5, +6 Species; |
| | | | | $PuO_2$ (dioxide) | |
| | | | +5 | $PuO_2^+$ (hypoplutonyl) | +5 Species/+6 Species |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericous) | +3 Species/+4, +5, +6 Species; |
| | | | +4 | $Am^{+4}$ (americous) | +4 Species/+5, +6 Species; |
| | | | | $AmO_2$ (dioxide) | |
| | | | | $Am(OH)_4$ (hydroxide) | |
| | | | +5 | $AmO_2^+$ (hypoamericyl) | +5 Species/+6 Species |
| | | | | $Am_2O_5$ (pentoxide) | |
| | | | +6 | $AmO_2^{+2}$ (americyl) | |
| | | | | $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | further comprising an ultraviolet source connected to the anolyte chamber for decomposing hydrogen peroxide into hydroxyl free radicals as secondary oxidizers and increasing efficiency of the process by recovering energy through the oxidation of the animal waste materials in the anolyte chamber by secondary oxidizers.

6. Apparatus for treating and oxidizing animal waste materials comprising an electrochemical cell, an aqueous electrolyte disposed in the electrochemical cell, a semi permeable membrane, ion selective membrane, microporous polymer, porous ceramic or glass frit membrane disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising an anolyte reaction chamber and buffer tank housing the bulk of the anolyte solution, an input pump to enter liquid animal waste into the anolyte reaction chamber, a spray head and stream head to introduce the anolyte from the electrochemical cell into the anolyte reaction chamber in such a manner as to promote mixing of the incoming anolyte and the anolyte mixture in the anolyte reaction chamber, a hinged lid to allow insertion of waste into the anolyte portion as liquid, solid of combination of both, a locking latch to secure the lid during operation of the system, a suction pump attached to the buffer tank to pump anolyte from the buffer tank to the anolyte reaction chamber, a input pump to pump anolyte from the anolyte reaction chamber back to the buffer tank, and an air pump to pump off gases from the anolyte reaction chamber back to the buffer tank for further oxidation.

7. Apparatus for treating and oxidizing animal waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising an ultrasonic source connected to the anolyte for augmenting secondary oxidation processes by heating hydrogen peroxide containing electrolyte to 4800° C., at 1000 atmospheres for dissociating hydrogen peroxide into hydroxyl free radicals and thus increasing concentration of oxidizing species and rate of waste destruction and for irradiating biological cell membranes in animal materials to momentarily raise the temperature within the biological cell membranes to above several thousand degrees, causing biological cell membrane failure, and creating greater exposure of biological cell contents to oxidizing species in the anolyte.

8. The apparatus of claim 7, wherein the membrane is an ion-selective membrane, or semi permeable membrane, microporous polymer membrane, porous ceramic membrane, or glass frit.

9. Apparatus for treating and oxidizing animal waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising an anolyte reaction chamber holding most of the anolyte portion and a foraminous basket, a penetrator attached to the basket to puncture solids increasing the exposed area, and further comprising an external $CO_2$ vent connected to the reaction chamber for releasing $CO_2$ into the atmosphere, a hinged lid attached to the reaction chamber allowing insertion of waste into the anolyte portion as liquid, solid, or mixtures of liquids and solids, an anolyte pump connected to the reaction chamber, an inorganic compounds removal and treatment system connected to the anolyte pump for removing chlorides, and other precipitate forming anions present in the animal waste being processed, thereby precluding formation of unstable oxycompounds, further comprising thermal control units connected to heat or cool the anolyte to a selected temperature range when anolyte is circulated into the reaction chamber through the electrochemical cell by the anolyte pump on the anode chamber side of the membrane, a flush for flushing the anolyte, and a filter is located at the base of the reaction chamber to limit the size of exiting solid particles to approximately 1 mm in diameter.

10. The apparatus of claim 9, wherein the membrane is an ion-selective membrane, or semi permeable membrane, microporous polymer membrane, porous ceramic membrane, or glass frit.

11. Apparatus for treating and oxidizing animal waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising an anolyte recovery system connected to a catholyte pump, a catholyte reservoir connected to the cathode portion of the electrochemical cell, a thermal control unit connected to the catholyte reservoir for varying the temperature of the catholyte portion, a bulk of the catholyte portion being resident in a catholyte reservoir, wherein the catholyte portion of the electrolyte flows into a catholyte reservoir, and further comprising an air sparge connected to the catholyte reservoir for introducing air into the catholyte reservoir.

12. The apparatus of claim 11, further comprising an anolyte recovery system for capturing the anions and for reintroducing the anions into the anolyte chamber upon collection from the catholyte electrolyte, an off-gas cleaning system connected to the catholyte reservoir for cleaning gases before release into the atmosphere, and an atmospheric vent connected to the off-gas cleaning system for releasing gases into the atmosphere, wherein cleaned gas from the off-gas cleaning system is combined with unreacted components of the air introduced into the system and discharged through the atmospheric vent 47.

13. The apparatus of claim 11, further comprising a screwed top on the catholyte reservoir to facilitate flushing out the catholyte reservoir, a mixer connected to the catholyte reservoir for stirring the catholyte, a catholyte pump connected to the catholyte reservoir for circulating catholyte back to the electrochemical cell, a drain for draining catholyte, a flush for flushing the catholyte system, and an air sparge connected to the housing for introducing air into the catholyte reservoir, wherein the catholyte portion of the electrolyte is circulated by pump through the electrochemical cell on the cathode side of the membrane, and wherein contact of oxidizing gas with the catholyte portion of the electrolyte is enhanced by promoting gas/liquid contact by mechanical and/or ultrasonic mixing.

14. The apparatus of claim 11, wherein the membrane is an ion-selective membrane, or semi permeable membrane, microporous polymer membrane, porous ceramic membrane, or glass frit.

15. Apparatus for treating and oxidizing animal waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the electrochemical cell is operated at high membrane current densities above about 0.5 amps/cm$^2$ for increasing a rate of waste destruction, also results in increased mediator ion transport through the membrane into the catholyte, and further comprising an anolyte recovery system positioned on the catholyte side, air sparging on the catholyte side to dilute and remove off-gas and hydrogen, wherein some mediator oxidizer ions cross the membrane and are removed through the anolyte recovery system to maintain process efficiency or cell operability.

16. The apparatus of claim 15, wherein the membrane is an ion-selective membrane, or semi permeable membrane, microporous polymer membrane, porous ceramic membrane, or glass frit.

17. Apparatus for treating and oxidizing animal waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising a controller, a microprocessor, a monitor and a keyboard connected to the cell for inputting commands to the controller through the keyboard responding to the information displayed on the monitor, a program in the controller sequencing the steps for operation of the apparatus, program having pre-programmed sequences of operations the operator follows or chooses other sequences of operations, the controller allows the operator to select sequences within limits that assure a safe and reliable operation, the controller sends digital commands that regulate electrical power to pumps, mixers, thermal controls, ultraviolet sources, ultrasonic sources, $CO_2$ vents, air sparge, and the electrochemical cell, the controller receives component response and status from the components, the controller sends digital commands to the sensors to access sensor information through sensor responses, sensors in the apparatus provide digital information on the state of components, sensors measure flow rate, temperature, pH, $CO_2$ venting, degree of oxidation, and air sparging, the controller receives status information on electrical potential across the electrochemical cell or individual cells in a multi-cell configuration and between the anodes and reference electrodes internal to the cells and the current flowing between the electrodes within each cell.

18. The apparatus of claim 17, wherein the membrane is an ion-selective membrane, or semi permeable membrane, microporous polymer membrane, porous ceramic membrane, or glass frit.

19. A animal waste destruction system, comprising a housing constructed of metal or high strength plastic surrounding an electrochemical cell, with electrolyte and a foraminous basket, an AC power supply with a power cord, a DC power supply connected to the AC power supply, the DC power supply providing direct current to the electrochemical cell, a control keyboard for input of commands and data, a monitor screen to display the systems operation and functions, an anolyte reaction chamber with a basket, status lights for displaying information about the status of the treatment of the animal waste material, an air sparge for introducing air into a catholyte reservoir below a surface of a catholyte, a $CO_2$ vent incorporated into the housing to allow for $CO_2$ release from the anolyte reaction chamber, an atmospheric vent facilitating the releases of gases into the atmosphere from the catholyte reservoir, a hinged lid for opening and depositing the animal waste in the basket in the anolyte reaction chamber, a locking latch connected to the hinged lid, and in the anolyte reaction chamber an aqueous acid, alkali, or neutral salt electrolyte and mediated oxidizer species solution in which an oxidizer form of a mediator redox couple initially may be present or may be generated electrochemically after introduction of the waste and application of DC power to the electrochemical cell.

20. The system of claim 19, wherein the waste is introduced when the anolyte is at room temperature, operating temperature or intermediate temperature, and the animal waste material is rapidly oxidized at temperatures below boiling point of anolyte at ambient pressure, and further comprising a pump circulating an anolyte portion of an electrolyte, an in-line filter preventing solid particles large enough to clog electrochemical cell flow paths from exiting the reaction chamber, an inorganic compound removal and treatment system and drain outlets connected to the anolyte reaction chamber, whereby residue is pacified in the form of a salt and may be periodically removed, and a removable top connected to a catholyte reservoir allowing access to the reservoir for cleaning and maintenance.

21. A animal waste oxidizing process, comprising an operator engaging an 'ON' button on a control keyboard, a system controller which contains a microprocessor, running a program and controlling a sequence of operations, a monitor screen displaying process steps in proper sequence, status lights on the panel providing status of the process, opening a lid and placing the animal waste in a basket as a liquid, solid, or a mixture of liquids and solids, retaining a solid portion of the waste and flowing a liquid portion through the basket and into an anolyte reaction chamber, activating a locking latch after the waste is placed in the basket, activating pumps which begins circulating the anolyte and a catholyte, once the circulating is established throughout the system, operating mixers, once flow is established, turning on thermal control units, and initiating anodic oxidation and electrolyte heating programs, energizing an electrochemical cell to electric potential and current density determined by the controller program, using programmed electrical power and electrolyte temperature ramps for maintaining a predetermined waste destruction rate profile as a relatively constant reaction rate as more reactive waste components are oxidized, thus resulting in the remaining waste becoming less and less reactive, thereby requiring more and more vigorous oxidizing conditions, activating ultrasonic and ultraviolet systems in the anolyte reaction chamber and catholyte reservoir, releasing $CO_2$ from the animal waste oxidizing process in the anolyte reaction chamber, activating air sparge and atmospheric vent in a catholyte system, monitoring progress of the process in the controller by cell voltages and currents, monitoring $CO_2$, CO, and $O_2$ gas composition for $CO_2$, CO and oxygen content, decomposing the animal waste into water and $CO_2$, the latter being discharged out of the $CO_2$ vent, air sparging drawing air into a catholyte reservoir, and discharging excess air out of an atmospheric vent, determining with an oxidation sensor that desired degree of waste destruction has been obtained, setting the system to standby, and executing system shutdown using the controller keyboard system operator.

22. The process of claim 21, further comprising placing the system in a standby mode during the day and adding animal waste as it is generated throughout the day, placing the system in full activation during non-business hours, operating the system at low temperature and ambient atmospheric pressure and not generating toxic compounds during the destruction of the animal waste, making the process indoors compatible, scaling the system between units small enough for use by a single practitioner and units large enough to replace hospital incinerators, releasing $CO_2$ oxidation product from the anolyte system out through the $CO_2$ vent, and venting off-gas products from the catholyte reservoir through the atmospheric vent.

23. The process of claim 21, further comprising introducing the waste into a room temperature or cooler system with little or none of the mediator redox couple in the oxidizer form, depending upon reaction kinetics, heat of reaction and similar waste characteristics.

24. A process for treating and oxidizing animal waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the animal waste materials in the anolyte portion, and oxidizing the animal waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof; or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| 1 | A | None | | | |
|   | B | Copper (Cu) | +2 | $Cu^{-2}$ (cupric) | +2 Species/+3, +4 Species; |
|   |   |   |   | $HCuO_2$ (bicuprite) |   |
|   |   |   |   | $CuO_2^{-2}$ (cuprite) | +3 Species/+4 Species |
|   |   |   | +3 | $Cu^{+3}$ |   |
|   |   |   |   | $CuO_2^-$ (cuprate) |   |
|   |   |   |   | $Cu_2O_3$ (sesquioxide) |   |
|   |   |   | +4 | $CuO_2$ (peroxide) |   |
|   |   | Silver (Ag) | +1 | $Ag^+$ (argentous) | +1 Species/+2, +3 Species; |
|   |   |   |   | $AgO^-$ (argentite) |   |
|   |   |   | +2 | $Ag^{+2}$ (argentic) | +2 Species/+3 Species |
|   |   |   |   | AgO (argentic oxide) |   |
|   |   |   | +3 | $AgO^+$ (argentyl) |   |
|   |   |   |   | $Ag_2O_3$ (sesquioxide) |   |
|   |   | Gold (Au) | +1 | $Au^+$ (aurous) | +1 Species/+3, +4 Species; |
|   |   |   | +3 | $Au^{+3}$ (auric) |   |
|   |   |   |   | $AuO^-$ (auryl) | +3 Species/+4 Species |
|   |   |   |   | $H_3AuO_3^-$ (auric acid) |   |
|   |   |   |   | $H_2AuO_3^-$ (monoauarate) |   |
|   |   |   |   | $HAuO_3^{-2}$ (diaurate) |   |
|   |   |   |   | $AuO_3^{-3}$ (triaurate) |   |
|   |   |   |   | $Au_2O_3$ (auric oxide) |   |
|   |   |   |   | $Au(OH)_3$ (auric hydroxide) |   |
|   |   |   | +4 | $AuO_2$ (peroxide) |   |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| II | A | Magnesium (Mg) | +2 | $Mg^{+2}$ (magnesic) | +2 Species/+4 Species |
|  |  |  | +4 | $MgO_2$ (peroxide) |  |
|  |  | Calcium (Ca) | +2 | $Ca^{+2}$ | +2 Species/+4 Species |
|  |  |  | +4 | $CaO_2$ (peroxide) |  |
|  |  | Strontium | +2 | $Sr^{+2}$ | +2 Species/ +4 Species |
|  |  |  | +4 | $SrO_2$ (peroxide) |  |
|  |  | Barium (Ba) | +2 | $Ba^{+2}$ | +2 Species/+4 Species |
|  |  |  | +4 | $BaO_2$ (peroxide) |  |
| II | B | Zinc (Zn) | +2 | $Zn^{+2}$ (zincic) | +2 Species/ +4 Species |
|  |  |  |  | $ZnOH^+$ (zincyl) |  |
|  |  |  |  | $HZnO_2^-$ (bizincate) |  |
|  |  |  |  | $ZnO_2^{-2}$ (zincate) |  |
|  |  |  | +4 | $ZnO_2$ (peroxide) |  |
|  |  | Mercury (Hg) | +2 | $Hg^{+2}$ (mercuric) | +2 Species/ +4 Species |
|  |  |  |  | $Hg(OH)_2^-$ (mercuric hydroxide) |  |
|  |  |  |  | $HHgO_2^-$ (mercurate) |  |
|  |  |  | +4 | $HgO_2$ (peroxide) |  |
| III | A | Boron | +3 | $H_3BO_3$ (orthoboric acid) | +3 Species/ +4.5, 5 Species |
|  |  |  |  | $H_2BO_3^-$, $HBO_3^{-2}$, $BO_3^{-3}$ (orthoborates) |  |
|  |  |  |  | $BO_2^-$ (metaborate) |  |
|  |  |  |  | $H_2B_4O_7$ (tetraboric acid) |  |
|  |  |  |  | $HB_4O_7^-/B_4O_7^{-2}$ (tetraborates) |  |
|  |  |  |  | $B_2O_4^{-2}$ (diborate) |  |
|  |  |  |  | $B_6O_{10}^{-2}$ (hexaborate) |  |
|  |  |  | +4.5 | $B_2O_5^-$ (diborate) |  |
|  |  |  | +5 | $BO_3^-/BO_2^- \cdot H_2O$ (perborate) |  |
|  |  | Thallium (Tl) | +1 | $Tl^{+1}$ (thallous) | +1 Species/ +3 or +3.33 Species; +3 Species/ +3.33 Species |
|  |  |  | +3 | $Tl^{+3}$ (thallic) |  |
|  |  |  |  | $TlO^+$, $TlOH^{+2}$, $Tl(OH)_2^+$ (thallyl) |  |
|  |  |  |  | $Tl_2O_3$ (sesquioxide) |  |
|  |  |  |  | $Tl(OH)_3$ (hydroxide) |  |
|  |  |  | +3.33 | $Tl_3O_5$ (peroxide) |  |
|  | B | See Rare Earths and Actinides |  |  |  |
| IV | A | Carbon (C) | +4 | $H_2CO_3$ (carbonic acid) | +4 Species/ 5, +6 Species |
|  |  |  |  | $HCO_3^-$ (bicarbonate) |  |
|  |  |  |  | $CO_3^{-2}$ (carbonate) |  |
|  |  |  | +5 | $H_2C_2O_6$ (perdicarbonic acid) |  |
|  |  |  | +6 | $H_2CO_4$ (permonocarbonic acid) |  |
|  |  | Germanium (Ge) | +4 | $H_2GeO_3$ (germanic acid) | +4 Species/ +6 Species |
|  |  |  |  | $HGeO_3^-$ (bigermaniate) |  |
|  |  |  |  | $GeO_3^{-4}$ (germinate) |  |
|  |  |  |  | $Ge_4^{+4}$ (germanic) |  |
|  |  |  |  | $GeO_4^{-4}$ |  |
|  |  |  |  | $H_2Ge_2O_5$ (digermanic acid) |  |
|  |  |  |  | $H_2Ge_4O_9$ (tetragermanic acid) |  |
|  |  |  |  | $H_2Ge_5O_{11}$ (pentagermanic acid) |  |
|  |  |  |  | $HGe_5O_{11}^-$ (bipentagermanate) |  |
|  |  |  | +6 | $Ge_5O_{11}^{-2}$ (pentagermanate) |  |
|  |  | Tin (Sn) | +4 | $Sn^{+4}$ (stannic) | +4 Species/ +7 Species |
|  |  |  |  | $HSnO_3^-$ (bistannate) |  |
|  |  |  |  | $SnO_3^{-2}$ (stannate) |  |
|  |  |  |  | $SnO_2$ (stannic oxide) |  |
|  |  |  |  | $Sn(OH)_4$ (stannic hydroxide) |  |
|  |  |  | +7 | $SnO_4^-$ (perstannate) |  |
|  |  | Lead (Pb) | +2 | $Pb^{+2}$ (plumbous) | +2, +2.67, +3 Species/+4 Species |
|  |  |  |  | $HPbO_2^-$ (biplumbite) |  |
|  |  |  |  | $PbOH^+$ |  |
|  |  |  |  | $PbO_2^{-2}$ (plumbite) |  |
|  |  |  |  | $PbO$ (plumbus oxide) |  |
|  |  |  | +2.67 | $Pb_3O_4$ (plumbo-plumbic oxide) |  |
|  |  |  | +3 | $Pb_2O_3$ (sesquioxide) |  |
| IV | A | Lead (Pb) | +4 | $Pb^{+4}$ (plumbic) | +2, +2.67, +3 Species/+4 Species |
|  |  |  |  | $PbO_3^{-2}$ (metaplumbate) |  |
|  |  |  |  | $HPbO_3^-$ (acid metaplumbate) |  |
|  |  |  |  | $PbO_4^{-4}$ (orthoplumbate) |  |
|  |  |  |  | $PbO_2$ (dioxide) |  |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| IV | B | Titanium | +4 | $TiO^{+2}$ (pertitanyl) <br> $HTiO_4^-$ titanate) <br> $TiO_2$ (dioxide) | +4 Species/ <br> +6 Species |
| | | | +6 | $TiO_2^{+2}$ (pertianyl) <br> $HTiO_4^-$ (acid pertitanate) <br> $TiO_4^{-2}$ (pertitanate) <br> $TiO_3$ (peroxide) | |
| | | Zirconium (Zr) | +4 | $Zr^{+4}$ (zirconic) <br> $ZrO^{+2}$ (zirconyl) <br> $HZrO_3^-$ (zirconate) | +4 Species/+5, <br> +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafhic) <br> $HfO^{+2}$ (hafnyl) | +4 Species/ <br> +6 Species |
| | | | +6 | $HfO_3$ (peroxide) | |
| V | A | Nitrogen | +5 | $HNO_3$ (nitric acid) <br> $NO_3^-$ (nitrate) | +5 species/ <br> +7 Species |
| | | | +7 | $HNO_4$ (pernitric acid) | |
| | | Phosphorus (P) | +5 | $H_3PO_4$ (orthophosphoric acid) <br> $H_2PO_4^-$ (monoorthophosphate) <br> $HPO_4^{-2}$ (diorthophosphate) <br> $PO_4^{-3}$ (triorthophosphate) <br> $HPO_3$ (metaphosphoric acid) <br> $H_4P_2O_7$ (pryophosphoric acid) <br> $H_5P_3O_{10}$ (triphosphoric acid) <br> $H_6P_4O_{13}$ (tetraphosphoric acid) | +5 Species/ <br> +6, +7 species |
| V | A | Phosphorus (P) | +6 | $H_4P_2O_8$ (perphosphoric acid) | +5 Species/ |
| | | | +7 | $H_3PO_5$ (monoperphosphoric acid) | +6, +7 Species |
| V | A | Arsenic (As) | +5 | $H_3AsO_4$ (ortho-arsenic acid) <br> $H_2AsO_4^-$ (mono ortho-arsenate) <br> $HAsO_4^{-2}$ (di-ortho-arsenate) <br> $AsO_4^{-3}$ (tri-ortho-arsenate) <br> $AsO_2^+$ (arsenyl) | +5 Species/ <br> +7 species |
| | | | +7 | $AsO_3^+$ (perarsenyl) | |
| | | Bismuth (Bi) | +3 | $Bi^{+3}$ (bismuthous) <br> $BiOH^{+2}$ (hydroxybismuthous) <br> $BiO^+$ (bismuthyl) <br> $BiO_2^-$ (metabismuthite) | +3 Species/ <br> +3.5, +4, +5 <br> Species |
| | | | +3.5 | $Bi_4O_7$ (oxide) | |
| | | | +4 | $Bi_2O_4$ (tetroxide) | |
| | | | +5 | $BiO_3^-$ (metabismuthite) <br> $Bi_2O_5$ (pentoxide) | |
| | B | Vanadium (V) | +5 | $VO_2^+$ (vanadic) <br> $H_3V_2O_7^-$ (pyrovanadate) <br> $H_2VO_4^-$ (orthovanadate) <br> $VO_3^-$ (metavanadate) <br> $HVO_4^{-2}$ (orthovanadate) <br> $VO_4^{-3}$ (orthovanadate) <br> $V_2O_5$ (pentoxide) <br> $H_4V_2O_7$ (pyrovanadic acid) <br> $HVO_3$ (metavanadic acid) <br> $H_4V_6O_{17}$ (hexavanadic acid) | 5 Species/ <br> +7, +9 Species |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) <br> $NbO_4^{-3}$ (orthoniobate) <br> $Nb_2O_5$ (pentoxide) <br> $HNbO_3$ (niobid acid) | +5 Species/+7 <br> species |
| | | | +7 | $NbO_4^-$ (perniobate) <br> $Nb_2O_7$ (perniobic acid) <br> $HNbO_4$ (perniobic acid) | |
| | | Tantalum (Ta) | +5 | $TaO_3^-$ (metatantalate) <br> $TaO_4^{-3}$ (orthotanatalate) <br> $Ta_2O_5$ (pentoxide) <br> $HTaO_3$ (tantalic acid) | +5 species/+7 <br> species |
| | | | +7 | $TaO_4^-$ (pentantalate) <br> $Ta_2O_7$ (pertantalate) <br> $HTaO_4 \cdot H_2O$ (pertantalic acid) | |
| VI | A | Sulfur (S) | +6 | $H_2SO_4$ (sulfuric acid) <br> $HSO_4^-$ (bisulfate) <br> $SO_4^{-2}$ (sulfate) | +6 Species/+7, <br> +8 Species |
| | | | +7 | $S_2O_8^{-2}$ (dipersulfate) | |
| | | | +8 | $H_2SO_5$ (momopersulfuric acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Selenium (Se) | +6 | $H_2Se_2O_4$ (selenic acid)<br>$HSeO_4^-$ (biselenate)<br>$SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid)<br>$HTeO_4^-$ (bitellurate)<br>$TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/ |
| | | | +4 | $PoO_3^{-2}$ (polonate) | +6 Species |
| | | | +6 | $PoO_3$ (peroxide) | |
| VI | B | Chromium | +3 | $Cr^{+3}$ (chromic)<br>$CrOH^{+2}$, $Cr(OH)_2^+$ (chromyls)<br>$CrO_2^-$, $CrO_3^{-3}$ (chromites)<br>$Cr_2O_3$ (chromic oxide)<br>$Cr(OH)_3$ (chromic hydroxide) | +3 Species/<br>+4, +6 Species;<br>+4 Species/<br>+6 Species |
| | | | +4 | $CrO_2$ (dioxide)<br>$Cr(OH)_4$ (hydroxide) | |
| | | | +6 | $H_2CrO_4$ (chromic acid)<br>$HCrO_4^-$ (acid chromate)<br>$CrO_4^{-2}$ (chromate)<br>$Cr_2O_7^{-2}$ (dichromate) | |
| | | Molybdenum (Mo) | +6 | $HMoO_4^-$ (bimolybhate)<br>$MoO_4^{-2}$ (molydbate)<br>$MoO_3$ (molybdic trioxide)<br>$H_2MoO_4$ (molybolic acid) | +6 Species/<br>+7 Species |
| | | | +7 | $MoO_4^-$ (permolybdate) | |
| | | Tungsten (W) | +6 | $WO_4^{-2}$ tungstic<br>$WO_3$ (trioxide)<br>$H_2WO_4$ (tungstic acid) | +6 Species/<br>+8 Species |
| | | | +8 | $WO_4^{-2}$ (pertungstic)<br>$H_2WO_5$ (pertungstic acid) | |
| VII | A | Chlorine (Cl) | +1 | HClO (hypochlorous acid)<br>$ClO^-$ (hypochlorite) | +1 Species/ +3,<br>+5, +7 Species; |
| | | | +3 | $HClO_2$ (chlorous acid)<br>$ClO_2^-$ (chlorite) | +3 Species/<br>+5, +7 Species; |
| | | | +5 | $HClO_3$ (chloric acid)<br>$ClO_3^-$ (chlorate) | +5 Species/<br>+7 Species |
| | | | +7 | $HClO_4$ (perchloric acid)<br>$ClO_4^-$, $HClO_5^{-2}$, $ClO_5^{-3}$, $Cl_2O_9^{-4}$<br>(perchlorates) | |
| VII | A | Bromine (Br) | +1 | HBrO (hypobromous acid)<br>$BrO^-$ (hypobromitee) | +1 Species/+3,<br>+5, +7 Species; |
| | | | +3 | $HBrO_2$ (bromous acid)<br>$BrO2^-$ (bromite) | +3 Species/+5,<br>+7 Species; |
| | | | +5 | $HBrO_3$ (bromic acid)<br>$BrO_3^-$ (bromate) | +5 Species/+7 Species |
| | | | +7 | $HBrO_4$ (perbromic acid)<br>$BrO_4^-$, $HBrO_5^{-2}$, $BrO_5^{-3}$, $Br_2O_9^{-4}$<br>(prebromates) | |
| | | Iodine | +1 | HIO (hypoiodus acid)<br>$IO^-$ (hypoiodite) | +1 Species/+3,<br>+5, +7 Species; |
| | | | +3 | $HIO_2$ (iodous acid)<br>$IO_2^-$ (iodite) | +3 Species/ +5,<br>+7 Species; |
| | | | +5 | $HIO_3$ (iodic acid)<br>$IO_3^-$ (iodate) | +5 Species/+7 Species |
| | | | +7 | $HIO_4$ (periodic acid)<br>$IO_4^-$, $HIO_5^{-2}$, $IO_5^{-3}$, $I_2O_9^{-4}$<br>(periodates) | |
| | B | Manganese (Mn) | +2 | $Mn^{+2}$ (manganeous)<br>$HMnO_2^-$ (dimanganite) | +2 Species/+3,<br>+4, +6, +7 Species; |
| | | | +3 | $Mn^{+3}$ (manganic) | |
| | | | +4 | $MnO_2$ (dioxide) | +3 Species/+4, |
| | | | +6 | $MnO_4^{-2}$ (manganate) | +6, +7 Species; |
| | | | +7 | $MnO_4^-$ (permanganate) | +4 Species/+6,<br>+7 Species;<br>+6 Species/+7 Species |
| VIII | Period 4 | Iron (Fe) | +3 | $FeO^{+3}$ (ferric)<br>$Fe(OH)^{+2}$<br>$Fe(OH)_2^+$<br>$FeO_2^{-2}$ (ferrite) | +3 Species/+4,<br>+5, +6 Species;<br>+4 Species/<br>+5, +6 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VIII | Period 4 | Iron (Fe) | +4 | $FeO^{+2}$ (ferryl) | +5 Species/ |
| | | | | $FeO_2^{-2}$ (perferrite) | +6 Species |
| | | | +5 | $FeO_2^+$ (perferryl) | |
| | | | +6 | $FeO_4^{-2}$ (ferrate) | |
| | | Cobalt (Ca) | +2 | $CO^{+2}$ (cobalous) | +2 Species/ |
| | | | | $HCoO_2^-$ (dicobaltite) | +3, +4 Species; |
| | | | +3 | $Co^{+3}$ (cobaltic) | +3 Species/ |
| | | | | $Co_2O_3$ (cobaltic oxide) | +4 Species |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, |
| | | | | $NiOH^+$ | +4, +6 Species; |
| | | | | $HNiO_2^-$ (dinickelite) | +3 Species/ |
| | | | | $NiO_2^{-2}$ (nickelite) | +4, +6 Species; |
| | | | +3 | $Ni^{+3}$ (nickelic) | +4 Species/ |
| | | | | $Ni_2O_3$ (nickelic oxide) | +6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3 |
| | | | +3 | $Ru^{+3}$ | +4, +5, +6, +7, |
| | | | | $Ru_2O_3$ (sesquioxide) | +8 Species; |
| | | | | $Ru(OH)_3$ (hydroxide) | +3 Species/+4, |
| | | | +4 | $Ru^{+4}$ (ruthenic) | +5, +6, +7, +8 |
| | | | | $RuO_2$ (ruthenic dioxide) | Species; |
| | | | | $Ru(OH)_4$ (ruthenic hydroxide) | +4 Species/ |
| | | | +5 | $Ru_2O_5$ (pentoxide) | +5, +6, +7, +8 |
| | | | +6 | $RuO_4^{-2}$ (ruthenate) | Species; |
| | | | | $RuO_2^{+2}$ (ruthenyl) | +5 Species/+6, |
| | | | | $RuO_3$ (trioxide) | +7, +8 Species; |
| | | | +7 | $RuO_4^-$ (perruthenate) | +6 Species/ |
| | | | +8 | $H_2RuO_4$ (hyperuthenic acid) | +7, +8 Species; |
| | | | | $HRuO_5^-$ (diperruthenate) | +7 Species/ |
| | | | | $RuO_4$ (ruthenium tetroxide) | +8 Species |
| | | Rhodium (Rh) | +1 | $Rh^+$ (hyporhobus) | +1 Species/+2, |
| | | | +2 | $Rh^{+2}$ (rhodous) | +3, +4, +6 |
| | | | +3 | $Rh^{+3}$ (rhodic) | Species; |
| | | | | $Rh_2O_3$ (sesquioxide) | +2 Species/+3, |
| | | | +4 | $RhO_2$ (rhodic oxide) | +4, +6 Species; |
| | | | | $Rh(OH)_4$ (hydroxide) | +3 Species/+4, |
| | | | +6 | $RhO_4^{-2}$ (rhodate) | +6 Species; |
| | | | | $RhO_3$ (trioxide) | +4 Species/+6 |
| | | | | | Species |
| | | Palladium | +2 | $Pd^{+2}$ (palladous) | +2 Species/+3, |
| | | | | $PdO_2^{-2}$ (palladite) | +4, +6 Species; |
| | | | +3 | $Pd_2O_3$ (sesquioxide) | +3 Species/ |
| | | | +4 | $Pd O_3^{-2}$ (palladate) | +4, +6 Species; |
| | | | | $PdO_2$ (dioxide) | +4 Species/ |
| | | | | $Pd(OH)_4$ (hydroxide) | +6 Species |
| | | | +6 | $PdO_3$ (peroxide) | |
| VIII | Period 6 | Iridium (Ir) | +3 | $Ir^{+3}$ (iridic) | +3 Species/ |
| | | | | $Ir_2O_3$ (iridium sesquioxide) | +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| | | | +6 | $PtO_4^{-2}$ (Perplatinate) | |
| | | | | $PtO_3$ (perplatinix oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}$, $Ce(OH)^{+3}$, $Ce(OH)_2^{+2}$, | +6 Species |
| | | | | $Ce(OH)_3^+$ (ceric) | |
| | | | | $CeO_2$ (ceric oxide) | |
| | | | +6 | $CeO_3$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Praseodymium (Pr) | +3 | $Pr^{+3}$ (praseodymous) $Pr_2O_3$ (sesquioxide) $Pr(OH)_3$ (hydroxide) | +3 species/+4 species |
| | | | +4 | $Pr^{+4}$ (praseodymic) $PrO_2$ (dioxide) | |
| | | Neodymium | +3 | $Nd^{+3}$ $Nd_2O_3$ (sesquioxide) | +3 Species/+4 Species |
| | | | +4 | $NdO_2$ (peroxide) | |
| | | Terbium (Tb) | +3 | $Tb^{+3}$ $Tb_2O_3$ (sesquioxide) | +3 Species/+4 Species |
| | | | +4 | $TbO_2$ (peroxide) | |
| IIIB | Actinides | Thorium (Th) | +4 | $Th^{+4}$ (thoric) $ThO^{+2}$ (thoryl) $HThO_3^-$ (thorate) | +4 Species/+6 Species |
| | | | +6 | $ThO_3$ (acid peroxide) | |
| | | Uranium (U) | +6 | $UO_2^{+2}$ (uranyl) $UO_3$ (uranic oxide) | +6 Species/+8 Species |
| | | | +8 | $HUO_5^-$, $UO_5^{-2}$ (peruranates) $UO_4$ (peroxide) | |
| | | Neptunium (Np) | +5 | $NpO_2^+$ (hyponeptunyl) $Np_2O_5$ (pentoxide) | +5 Species/+6, +8 Species; |
| | | | +6 | $NpO_2^{+2}$ (neptunyl) $NpO_3$ (trioxide) | +6 Species/+8 Species |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) $PuO_2$ (dioxide) | +4 Species/+5, +6 Species; |
| | | | +5 | $PuO_2^+$ (hypoplutonyl) $Pu_2O_5$ (pentoxide) | +5 Species/+6 Species |
| | | | +6 | $PuO_2^{+2}$ (plutonyl) $PuO_3$ (peroxide) | |
| | | Americium (Am) | +3 | $Am^{+3}$ (hypoamericous) | +3 Species/+4, +5, +6 Species; |
| | | | +4 | $Am^{+4}$ (americous) $AmO_2$ (dioxide) $Am(OH)_4$ (hydroxide) | +4 Species/+5, +6 Species; |
| | | | +5 | $AmO_2^+$ (hypoamericyl) $Am_2O_5$ (pentoxide) | +5 Species/+6 Species |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | further comprising adding stabilizing compounds to the electrolyte for overcoming and stabilizing the short lifetime of oxidized forms of higher oxidation state species of the mediator, wherein the stabilizing compounds are tellurate or periodate ions.

25. A process for treating and oxidizing animal waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the animal waste materials in the anolyte portion, and oxidizing the animal waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| 1 | A | None | | | |
|   | B | Copper (Cu) | +2 | $Cu^{-2}$ (cupric) | +2 Species/+3, +4 |
|   |   |   |   | $HCuO_2$ (bicuprite) | Species; |
|   |   |   |   | $CuO_2^{-2}$ (cuprite) | +3 Species/+4 Species |
|   |   |   | +3 | $Cu^{+3}$ | |
|   |   |   |   | $CuO_2^-$ (cuprate) | |
|   |   |   |   | $Cu_2O_3$ (sesquioxide) | |
|   |   |   | +4 | $CuO_2$ (peroxide) | |
|   |   | Silver (Ag) | +1 | $Ag^+$ (argentous) | +1 Species/+2, +3 |
|   |   |   |   | $AgO^-$ (argentite) | Species; |
|   |   |   | +2 | $Ag^{-2}$ (argentic) | +2 Species/+3 Species |
|   |   |   |   | AgO (argentic oxide) | |
|   |   |   | +3 | $AgO^+$ (argentyl) | |
|   |   |   |   | $Ag_2O_3$ (sesquioxide) | |
|   |   | Gold (Au) | +1 | $Au^+$ (aurous) | +1 Species/+3, +4 |
|   |   |   | +3 | $Au^{+3}$ (auric) | Species; |
|   |   |   |   | $AuO^-$ (auryl) | +3 Species/+4 Species |
|   |   |   |   | $H_3AuO_3^-$ (auric acid) | |
|   |   |   |   | $H_2AuO_3^-$ (monoauarate) | |
|   |   |   |   | $HAuO_3^{-2}$ (diaurate) | |
|   |   |   |   | $AuO_3^{-3}$ (triaurate) | |
|   |   |   |   | $Au_2O_3$ (auric oxide) | |
|   |   |   |   | $Au(OH)_3$ (auric hydroxide) | |
|   |   |   | +4 | $AuO_2$ (peroxide) | |
| II | A | Magnesium (Mg) | +2 | $Mg^{+2}$ (magnesic) | +2 Species/+4 Species |
|   |   |   | +4 | $MgO_2$ (peroxide) | |
|   |   | Calcium (Ca) | +2 | $Ca^{+2}$ | +2 Species/+4 Species |
|   |   |   | +4 | $CaO_2$ (peroxide) | |
|   |   | Strontium | +2 | $Sr^{+2}$ | +2 Species/ +4 Species |
|   |   |   | +4 | $SrO_2$ (peroxide) | |
|   |   | Barium (Ba) | +2 | $Ba^{+2}$ | +2 Species/+4 Species |
|   |   |   | +4 | $BaO_2$ (peroxide) | |
| II | B | Zinc (Zn) | +2 | $Zn^{+2}$ (zincic) | +2 Species/ |
|   |   |   |   | $ZnOH^+$ (zincyl) | +4 Species |
|   |   |   |   | $HZnO_2^-$ (bizincate) | |
|   |   |   |   | $ZnO_2^{-2}$ (zincate) | |
|   |   |   | +4 | $ZnO_2$ (peroxide) | |
|   |   | Mercury (Hg) | +2 | $Hg^{+2}$ (mercuric) | +2 Species/ |
|   |   |   |   | $Hg(OH)_2$ (mercuric hydroxide) | +4 Species |
|   |   |   |   | $HHgO_2^-$ (mercurate) | |
|   |   |   | +4 | $HgO_2$ (peroxide) | |
| III | A | Boron | +3 | $H_3BO_3$ (orthoboric acid) | +3 Species/ |
|   |   |   |   | $H_2BO_3^-, HBO_3^{-2}, BO_3^{-3}$ (orthoborates) | +4.5, 5 Species |
|   |   |   |   | $BO_2^-$ (metaborate) | |
|   |   |   |   | $H_2B_4O_7$ (tetraboric acid) | |
|   |   |   |   | $HB_4O_7^-/B_4O_7^{-2}$ (tetraborates) | |
|   |   |   |   | $B_2O_4^{-2}$ (diborate) | |
|   |   |   |   | $B_6O_{10}^{-2}$ (hexaborate) | |
|   |   |   | +4.5 | $B_2O_5^-$ (diborate) | |
|   |   |   | +5 | $BO_3^-/BO_2^- \cdot H_2O$ (perborate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Thallium (Tl) | +1 | $Tl^{+1}$ (thallous) | +1 Species/ +3 or +3.33 Species; +3 Species/ +3.33 Species |
| | | | +3 | $Tl^{+3}$ (thallic) $TlO^+$, $TlOH^{+2}$, $Tl(OH)_2^+$ (thallyl) $Tl_2O_3$ (sesquioxide) $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) $HCO_3^-$ (bicarbonate) $CO_3^{-2}$ (carbonate) | +4 Species/ 5, +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) $HGeO_3^-$ (bigermaniate) $GeO_3^{-4}$ (germinate) $Ge_4^{+4}$ (germanic) $GeO_4^{-4}$ $H_2Ge_2O_5$ (digermanic acid) $H_2Ge_4O_9$ (tetragermanic acid) $H_2Ge_5O_{11}$ (pentagermanic acid) $HGe_5O_{11}^-$ (bipentagermanate) | +4 Species/ +6 Species |
| | | | +6 | $Ge_5O_{11}^-$ (pentagermanate) | |
| | | Tin (Sn) | +4 | $Sn^{+4}$ (stannic) $HSnO_3^-$ (bistannate) $SnO_3^{-2}$ (stannate) $SnO_2$ (stannic oxide) $Sn(OH)_4$ (stannic hydroxide) | +4 Species/ +7 Species |
| | | | +7 | $SnO_4^-$ (perstannate) | |
| | | Lead (Pb) | +2 | $Pb^{+2}$ (plumbous) $HPbO_2^-$ (biplumbite) $PbOH^+$ $PbO_2^-$ (plumbite) $PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic) $PbO_3^{-2}$ (metaplumbate) $HPbO_3^-$ (acid metaplumbate) $PbO_4^{-4}$ (orthoplumbate) $PbO_2$ (dioxide) | +2, +2.67, +3 Species/+4 Species |
| IV | B | Titanium | +4 | $TiO^{+2}$ (pertitanyl) $HTiO_4^-$ titanate) $TiO_2$ (dioxide) | +4 Species/ +6 Species |
| | | | +6 | $TiO_2^{+2}$ (pertitanyl) $HTiO_4^-$ (acid pertitanate) $TiO_4^{-2}$ (pertitanate) $TiO_3$ (peroxide) | |
| | | Zirconium (Zr) | +4 | $Zr^{+4}$ (zirconic) $ZrO^{+2}$ (zirconyl) $HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) $HfO^{+2}$ (hafnyl) | +4 Species/ +6 Species |
| | | | +6 | $HfO_3$ (peroxide) | |
| V | A | Nitrogen | +5 | $HNO_3$ (nitric acid) $NO_3^-$ (nitrate) | +5 species/ +7 Species |
| | | | +7 | $HNO_4$ (pernitric acid) | |
| | | Phosphorus (P) | +5 | $H_3PO_4$ (orthophosphoric acid) $H_2PO_4^-$ (monoorthophosphate) $HPO_4^{-2}$ (diorthophosphate) $PO_4^{-3}$ (triorthophosphate) $HPO_3$ (metaphosphoric acid) $H_4P_2O_7$ (pryophosphoric acid) $H_5P_3O_{10}$ (triphosphoric acid) $H_6P_4O_{13}$ (tetraphosphoric acid) | +5 Species/ +6, +7 species |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| V | A | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/<br>+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/<br>+3.5, +4, +5<br>Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | 5 Species/<br>+7, +9 Species |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7<br>species |
| | | | +7 | $NbO_4^-$ (perniobate)<br>$Nb_2O_7$ (perniobic oxide)<br>$HNbO_4$ (perniobic acid) | |
| | | Tantalum (Ta) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7<br>species |
| | | | +7 | $TaO_4^-$ (pentantalate)<br>$Ta_2O_7$ (pertantalate)<br>$HTaO_4 \cdot H_2O$ (pertantalic acid) | |
| VI | A | Sulfur (S) | +6 | $H_2SO_4$ (sulfuric acid)<br>$HSO_4^-$ (bisulfate)<br>$SO_4^{-2}$ (sulfate) | +6 Species/+7,<br>+8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid)<br>$HSeO_4^-$ (biselenate)<br>$SeO_4^{-2}$ (selenate) | +6 species/+7<br>Species |
| | | | +7 | $H_2Se_2O_8$ (perdiselenic acid) | |
| | | Tellurium (Te) | +6 | $H_2TeO_4$ (telluric acid)<br>$HTeO_4^-$ (bitellurate)<br>$TeO_4^{-2}$ (tellurate) | +6 species/+7<br>species |
| | | | +7 | $H_2Te_2O_8$ (perditellenic acid) | |
| | | Polonium (Po) | +2 | $Po^{+2}$ (polonous) | +2, +4 species/<br>+6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic)<br>$CrOH^{+2}$, $Cr(OH)_2^+$ (chromyls)<br>$CrO_2^-$, $CrO_3^{-3}$ (chromites)<br>$Cr_2O_3$ (chromic oxide)<br>$Cr(OH)_3$ (chromic hydroxide) | +3 Species/<br>+4, +6 Species;<br>+4 Species/<br>+6 Species |
| | | | +4 | $CrO_2$ (dioxide)<br>$Cr(OH)_4$ (hydroxide) | |
| | | | +6 | $H_2CrO_4$ (chromic acid)<br>$HCrO_4^-$ (acid chromate)<br>$CrO_4^{-2}$ (chromate)<br>$Cr_2O_7^{-2}$ (dichromate) | |
| | | Molybdenum (Mo) | +6 | $HMoO_4^-$ (bimolybhate)<br>$MoO_4^{-2}$ (molydbate)<br>$MoO_3$ (molybdic trioxide)<br>$H_2MoO_4$ (molybolic acid) | +6 Species/<br>+7 Species |
| | | | +7 | $MoO_4^-$ (permolybdate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tungsten (W) | +6 | $WO_4^{-2}$ (tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | +1 | HClO (hypochlorous acid) $ClO^-$ (hypochlorite) | +1 Species/ +3, +5, +7 Species; |
| | | | +3 | $HClO_2$ (chlorous acid) $ClO_2^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-, HClO_5^{-2}, ClO_5^{-3}, Cl_2O_9^{-4}$ (perchlorates) | |
| VII | A | Bromine (Br) | +1 | HBrO (hypobromous acid) $BrO^-$ (hypobromitee) | +1 Species/+3, +5, +7 Species; |
| | | | +3 | $HBrO_2$ (bromous acid) $BrO2^-$ (bromite) | +3 Species/+5, +7 Species; |
| | | | +5 | $HBrO_3$ (bromic acid) $BrO_3^-$ (bromate) | +5 Species/+7 Species |
| | | | +7 | $HBrO_4$ (perbromic acid) $BrO_4^-, HBrO_5^{-2}, BrO_5^{-3}, Br_2O_9^{-4}$ (prebromates) | |
| | | Iodine | +1 | HIO (hypoiodus acid) $IO^-$ (hypoiodite) | +1 Species/+3, +5, +7 Species; |
| | | | +3 | $HIO_2$ (iodous acid) $IO_2^-$ (iodite) | +3 Species/+5, +7 Species; |
| | | | +5 | $HIO_3$ (iodic acid) $IO_3^-$ (iodate) | +5 Species/+7 Species |
| | | | +7 | $HIO_4$ (periodic acid) $IO_4^-, HIO_5^{-2}, IO_5^{-3}, I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species; |
| | | | +3 | $Mn^{+3}$ (manganic) | |
| | | | +4 | $MnO_2$ (dioxide) | +3 Species/+4, +6, +7 Species; |
| | | | +6 | $MnO_4^{-2}$ (manganate) | +4 Species/+6, +7 Species; |
| | | | +7 | $MnO_4^-$ (permanganate) | +6 Species/+7 Species |
| VIII | Period 4 | Iron (Fe) | +3 | $FeO^{+3}$ (ferric) $Fe(OH)^{+2}$ $Fe(OH)_2^+$ $FeO_2^-$ (ferrite) | +3 Species/+4, +5, +6 Species; +4 Species/ +5, +6 Species; |
| VIII | Period 4 | Iron (Fe) | +4 | $FeO^{+2}$ (ferryl) $FeO_2^{-2}$ (perferrite) | +5 Species/ +6 Species |
| | | | +5 | $FeO_2^+$ (perferryl) | |
| | | | +6 | $FeO_4^{-2}$ (ferrate) | |
| | | Cobalt (Ca) | +2 | $Co^{+2}$ (cobalous) $HCoO_2^-$ (dicobaltite) | +2 Species/ +3, +4 Species; |
| | | | +3 | $Co^{+3}$ (cobaltic) $Co_2O_3$ (cobaltic oxide) | +3 Species/ +4 Species |
| | | | +4 | $CoO_2$ (peroxide) $H_2CoO_3$ (cobaltic acid) | |
| | | Nickel (Ni) | +2 | $Ni^{+2}$ (nickelous) $NiOH^+$ $HNiO_2^-$ (dinickelite) $NiO_2^{-2}$ (nickelite) | +2 Species/+3, +4, +6 Species; +3 Species/ +4, +6 Species; |
| | | | +3 | $Ni^{+3}$ (nickelic) $Ni_2O_3$ (nickelic oxide) | +4 Species/ +6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3 |
| | | | +3 | $Ru^{+3}$ $Ru_2O_3$ (sesquioxide) $Ru(OH)_3$ (hydroxide) | +4, +5, +6, +7, +8 Species; +3 Species/+4, |
| | | | +4 | $Ru^{+4}$ (ruthenic) $RuO_2$ (ruthenic dioxide) $Ru(OH)_4$ (ruthenic hydroxide) | +5, +6, +7, +8 Species; +4 Species/ |
| | | | +5 | $Ru_2O_5$ (pentoxide) | +5, +6, +7, +8 Species; |
| | | | +6 | $RuO_4^{-2}$ (ruthenate) $RuO_2^{+2}$ (ruthenyl) $RuO_3$ (trioxide) | +5 Species/+6, +7, +8 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +7 | $RuO_4^-$ (perruthenate) | +6 Species/ |
| | | | +8 | $H_2RuO_4$ (hyperuthenic acid) | +7, +8 Species; |
| | | | | $HRuO_5^-$ (diperruthenate) | +7 Species/ |
| | | | | $RuO_4$ (ruthenium tetroxide) | +8 Species |
| | | Rhodium (Rh) | +1 | $Rh^+$ (hyporhobus) | +1 Species/+2, |
| | | | +2 | $Rh^{+2}$ (rhodous) | +3, +4, +6 |
| | | | +3 | $Rh^{+3}$ (rhodic) | Species; |
| | | | | $Rh_2O_3$ (sesquioxide) | +2 Species/+3, |
| | | | +4 | $RhO_2$ (rhodic oxide) | +4, +6 Species; |
| | | | | $Rh(OH)_4$ (hydroxide) | +3 Species/+4, |
| | | | +6 | $RhO_4^{-2}$ (rhodate) | +6 Species; |
| | | | | $RhO_3$ (trioxide) | +4 Species/+6 Species |
| | | Palladium | +2 | $Pd^{+2}$ (palladous) | +2 Species/+3, |
| | | | | $PdO_2^{-2}$ (palladite) | +4, +6 Species; |
| | | | +3 | $Pd_2O_3$ (sesquioxide) | +3 Species/ |
| | | | +4 | $PdO_3^{-2}$ (palladate) | +4, +6 Species; |
| | | | | $PdO_2$ (dioxide) | +4 Species/ |
| | | | | $Pd(OH)_4$ (hydroxide) | +6 Species |
| | | | +6 | $PdO_3$ (peroxide) | |
| VIII | Period 6 | Iridium (Ir) | +3 | $Ir^{+3}$ (iridic) | +3 Species/ |
| | | | | $Ir_2O_3$ (iridium sesquioxide) | +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| | | | +6 | $PtO_4^{-2}$ (Perplatinate) | |
| | | | | $PtO_3$ (perplatinix oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}$, $Ce(OH)^{+3}$, $Ce(OH)_2^{+2}$, $Ce(OH)_3^+$ (ceric) | +6 Species |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species; |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) | +4 Species/+5, +6 Species; |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Americium (Am) | +3 | $Am^{+3}$ (hypoamericous) | +3 Species/+4, +5, +6 Species; |
| | | | +4 | $Am^{+4}$ (americous) $AmO_2$ (dioxide) $Am(OH)_4$ (hydroxide) | +4 Species/+5, +6 Species; |
| | | | +5 | $AmO_2^+$ (hypoamericyl) $Am_2O_5$ (pentoxide) | +5 Species/+6 Species |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorus (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | wherein the oxidizing agents are super oxidizers, and further comprising generating inorganic free radicals in aqueous solutions from carbonate, azide, nitrite, nitrate, phosphite, phosphate, sulfite, sulfate, selenite, thiocyanate, chloride, and formate oxidizing species, wherein the super oxidizers have an oxidation potential above a threshold value of 1.7 volts at 1 molar, 25° C. and pH1.

26. Apparatus for treating and oxidizing animal waste materials comprising an electrochemical cell, an aqueous electrolyte disposed in the electrochemical cell, a semi permeable membrane, ion selective membrane, microporous membrane, porous ceramic or glass frit membrane disposed in the electrochemical cell for separating the cell into anolyte and catholyte chambers, and separating the anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| 1 | A | None | | | |
| | B | Copper (Cu) | +2 | $Cu^{-2}$ (cupric) $HCuO_2$ (bicuprite) $CuO_2^{-2}$ (cuprite) | +2 Species/+3, +4 Species; +3 Species/+4 Species |
| | | | +3 | $Cu^{+3}$ $CuO_2^-$ (cuprate) $Cu_2O_3$ (sesquioxide) | |
| | | | +4 | $CuO_2$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Silver (Ag) | +1 | $Ag^+$ (argentous)<br>$AgO^-$ (argentite) | +1 Species/+2, +3 Species; |
| | | | +2 | $Ag^{-2}$ (argentic)<br>AgO (argentic oxide) | +2 Species/+3 Species |
| | | | +3 | $AgO^+$ (argentyl)<br>$Ag_2O_3$ (sesquioxide) | |
| | | Gold (Au) | +1 | $Au^+$ (aurous) | +1 Species/+3, +4 Species; |
| | | | +3 | $Au^{+3}$ (auric)<br>$AuO^-$ (auryl)<br>$H_3AuO_3^-$ (auric acid)<br>$H_2AuO_3^-$ (monoauarate)<br>$HAuO_3^{-2}$ (diaurate)<br>$AuO_3^{-3}$ (triaurate)<br>$Au_2O_3$ (auric oxide)<br>$Au(OH)_3$ (auric hydroxide) | +3 Species/+4 Species |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/ +4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic)<br>$ZnOH^+$ (zincyl)<br>$HZnO_2^-$ (bizincate)<br>$ZnO_2^{-2}$ (zincate) | +2 Species/<br>+4 Species |
| | | | +4 | $ZnO_2$ (peroxide) | |
| | | Mercury (Hg) | +2 | $Hg^{+2}$ (mercuric)<br>$Hg(OH)_2$ (mercuric hydroxide)<br>$HHgO_2^-$ (mercurate) | +2 Species/<br>+4 Species |
| | | | +4 | $HgO_2$ (peroxide) | |
| III | A | Boron | +3 | $H_3BO_3$ (orthoboric acid)<br>$H_2BO_3^-$, $HBO_3^{-2}$, $BO_3^{-3}$ (orthoborates)<br>$BO_2^-$ (metaborate)<br>$H_2B_4O_7$ (tetraboric acid)<br>$HB_4O_7^-/B_4O_7^{-2}$ (tetraborates)<br>$B_2O_4^{-2}$ (diborate)<br>$B_6O_{10}^{-2}$ (hexaborate) | +3 Species/<br>+4.5, 5 Species |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{+1}$ (thallous) | +1 Species/<br>+3 or +3.33 Species; |
| | | | +3 | $Tl^{+3}$ (thallic)<br>$TlO^+$, $TlOH^{+2}$, $Tl(OH)_2^+$ (thallyl)<br>$Tl_2O_3$ (sesquioxide)<br>$Tl(OH)_3$ (hydroxide) | +3 Species/<br>+3.33 Species |
| | | | +3.33 | $Tl_3O_5$ (peroxide) | |
| | B | See Rare Earths and Actinides | | | |
| IV | A | Carbon (C) | +4 | $H_2CO_3$ (carbonic acid)<br>$HCO_3^-$ (bicarbonate)<br>$CO_3^{-2}$ (carbonate) | +4 Species/<br>5, +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid)<br>$HGeO_3^-$ (bigermaniate)<br>$GeO_3^{-4}$ (germinate)<br>$Ge_4^{+4}$ (germanic)<br>$GeO_4^{-4}$<br>$H_2Ge_2O_5$ (digermanic acid)<br>$H_2Ge_4O_9$ (tetragermanic acid)<br>$H_2Ge_5O_{11}$ (pentagermanic acid)<br>$HGe_5O_{11}^-$ (bipentagermanate) | +4 Species/<br>+6 Species |
| | | | +6 | $Ge_5O_{11}^-$ (pentagermanate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tin (Sn) | +4 | $Sn^{+4}$ (stannic) <br> $HSnO_3^-$ (bistannate) <br> $SnO_3^{-2}$ (stannate) <br> $SnO_2$ (stannic oxide) <br> $Sn(OH)_4$ (stannic hydroxide) | +4 Species/ <br> +7 Species |
| | | | +7 | $SnO_4^-$ (perstannate) | |
| | | Lead (Pb) | +2 | $Pb^{+2}$ (plumbous) <br> $HPbO_2^-$ (biplumbite) <br> $PbOH^+$ <br> $PbO_2^{-2}$ (plumbite) <br> $PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic) <br> $PbO_3^{-2}$ (metaplumbate) <br> $HPbO_3^-$ (acid metaplumbate) <br> $PbO_4^{-4}$ (orthoplumbate) <br> $PbO_2$ (dioxide) | +2, +2.67, +3 Species/+4 Species |
| IV | B | Titanium | +4 | $TiO^{+2}$ (pertitanyl) <br> $HTiO_4^-$ titanate) <br> $TiO_2$ (dioxide) | +4 Species/ <br> +6 Species |
| | | | +6 | $TiO_2^{+2}$ (pertitanyl) <br> $HTiO_4^-$ (acid pertitanate) <br> $TiO_4^{-2}$ (pertitanate) <br> $TiO_3$ (peroxide) | |
| | | Zirconium (Zr) | +4 | $Zr^{+4}$ (zirconic) <br> $ZrO^{+2}$ (zirconyl) <br> $HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafhic) <br> $HfO^{+2}$ (hafnyl) | +4 Species/ <br> +6 Species |
| | | | +6 | $HfO_3$ (peroxide) | |
| V | A | Nitrogen | +5 | $HNO_3$ (nitric acid) <br> $NO_3^-$ (nitrate) | +5 species/ <br> +7 Species |
| | | | +7 | $HNO_4$ (pernitric acid) | |
| | | Phosphorus (P) | +5 | $H_3PO_4$ (orthophosphoric acid) <br> $H_2PO_4^-$ (monoorthophosphate) <br> $HPO_4^{-2}$ (diorthophosphate) <br> $PO_4^{-3}$ (triorthophosphate) <br> $HPO_3$ (metaphosphoric acid) <br> $H_4P_2O_7$ (pryophosphoric acid) <br> $H_5P_3O_{10}$ (triphosphoric acid) <br> $H_6P_4O_{13}$ (tetraphosphoric acid) | +5 Species/ <br> +6, +7 species |
| V | A | Phosphorus (P) | +6 | $H_4P_2O_8$ (perphosphoric acid) | +5 Species/ |
| | | | +7 | $H_3PO_5$ (monoperphosphoric acid) | +6, +7 Species |
| V | A | Arsenic (As) | +5 | $H_3AsO_4$ (ortho-arsenic acid) <br> $H_2AsO_4^-$ (mono ortho-arsenate) <br> $HAsO_4^{-2}$ (di-ortho-arsenate) <br> $AsO_4^{-3}$ (tri-ortho-arsenate) <br> $AsO_2^+$ (arsenyl) | +5 Species/ <br> +7 species |
| | | | +7 | $AsO_3^+$ (perarsenyl) | |
| | | Bismuth (Bi) | +3 | $Bi^{+3}$ (bismuthous) <br> $BiOH^{+2}$ (hydroxybismuthous) <br> $BiO^+$ (bismuthyl) <br> $BiO_2^-$ (metabismuthite) | +3 Species/ <br> +3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite) <br> $Bi_2O_5$ (pentoxide) | |
| | B | Vanadium (V) | +5 | $VO_2^+$ (vanadic) <br> $H_3V_2O_7^-$ (pyrovanadate) <br> $H_2VO_4^-$ (orthovanadate) <br> $VO_3^-$ (metavanadate) <br> $HVO_4^{-2}$ (orthovanadate) <br> $VO_4^{-3}$ (orthovanadate) <br> $V_2O_5$ (pentoxide) <br> $H_4V_2O_7$ (pyrovanadic acid) <br> $HVO_3$ (metavanadic acid) <br> $H_4V_6O_{17}$ (hexavanadic acid) | 5 Species/ <br> +7, +9 Species |
| | | | +7 | $VO_4^-$ (pervanadate) | |
| | | | +9 | $VO_5^-$ (hypervanadate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| V | B | Niobium (Nb) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |
| | | | +7 | $NbO_4^-$ (perniobate)<br>$Nb_2O_7$ (perniobic oxide)<br>$HNbO_4$ (perniobic acid) | |
| | | Tantalum (Ta) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7 species |
| | | | +7 | $TaO_4^-$ (pentantalate)<br>$Ta_2O_7$ (pertantalate)<br>$HTaO_4 \cdot H_2O$ (pertantalic acid) | |
| VI | A | Sulfur (S) | +6 | $H_2SO_4$ (sulfuric acid)<br>$HSO_4^-$ (bisulfate)<br>$SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid)<br>$HSeO_4^-$ (biselenate)<br>$SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid)<br>$HTeO_4^-$ (bitellurate)<br>$TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic)<br>$CrOH^{+2}$, $Cr(OH)_2^+$ (chromyls)<br>$CrO_2^-$, $CrO_3^{-3}$ (chromites)<br>$Cr_2O_3$ (chromic oxide)<br>$Cr(OH)_3$ (chromic hydroxide) | +3 Species/ +4, +6 Species; +4 Species/ +6 Species |
| | | | +4 | $CrO_2$ (dioxide)<br>$Cr(OH)_4$ (hydroxide) | |
| | | | +6 | $H_2CrO_4$ (chromic acid)<br>$HCrO_4^-$ (acid chromate)<br>$CrO_4^{-2}$ (chromate)<br>$Cr_2O_7^{-2}$ (dichromate) | |
| | | Molybdenum (Mo) | +6 | $HMoO_4^-$ (bimolybhate)<br>$MoO_4^{-2}$ (molydbate)<br>$MoO_3$ (molybdic trioxide)<br>$H_2MoO_4$ (molybolic acid) | +6 Species/ +7 Species |
| | | | +7 | $MoO_4^-$ (permolybdate) | |
| | | Tungsten (W) | +6 | $WO_4^{-2}$ tungstic)<br>$WO_3$ (trioxide)<br>$H_2WO_4$ (tungstic acid) | +6 Species/ +8 Species |
| | | | +8 | $WO_4^{-2}$ (pertungstic)<br>$H_2WO_5$ (pertungstic acid) | |
| VII | A | Chlorine (Cl) | +1 | HClO (hypochlorous acid)<br>$ClO^-$ (hypochlorite) | +1 Species/ +3, +5, +7 Species; |
| | | | +3 | $HClO_2$ (chlorous acid)<br>$ClO_2^-$ (chlorite) | +3 Species/ +5, +7 Species; |
| | | | +5 | $HClO_3$ (chloric acid)<br>$ClO_3^-$ (chlorate) | +5 Species/ +7 Species |
| | | | +7 | $HClO_4$ (perchloric acid)<br>$ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid)<br>$BrO^-$ (hypobromitee) | +1 Species/+3, +5, +7 Species; |
| | | | +3 | $HBrO_2$ (bromous acid)<br>$BrO2^-$ (bromite) | +3 Species/+5, +7 Species; |
| | | | +5 | $HBrO_3$ (bromic acid)<br>$BrO_3^-$ (bromate) | +5 Species/+7 Species |
| | | | +7 | $HBrO_4$ (perbromic acid)<br>$BrO_4^-$, $HBrO_5^{-2}$, $BrO_5^{-3}$, $Br_2O_9^{-4}$ (prebromates) | |
| | | Iodine | +1 | HIO (hypoiodus acid)<br>$IO^-$ (hypoiodite) | +1 Species/+3, +5, +7 Species; |
| | | | +3 | $HIO_2$ (iodous acid)<br>$IO_2^-$ (iodite) | +3 Species/ +5, +7 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +5 | $HIO_3$ (iodic acid)<br>$IO_3^-$ (iodate) | +5 Species/+7 Species |
| | | | +7 | $HIO_4$ (periodic acid)<br>$IO_4^-$, $HIO_5^{-2}$, $IO_5^{-3}$, $I_2O_9^{-4}$ (periodates) | |
| | B | Manganese (Mn) | +2 | $Mn^{+2}$ (manganeous)<br>$HMnO_2^-$ (dimanganite) | +2 Species/+3, +4, +6, +7 Species; |
| | | | +3 | $Mn^{+3}$ (manganic) | +3 Species/+4, |
| | | | +4 | $MnO_2$ (dioxide) | +6, +7 Species; |
| | | | +6 | $MnO_4^{-2}$ (manganate) | +4 Species/+6, +7 Species; |
| | | | +7 | $MnO_4^-$ (permanganate) | +6 Species/+7 Species |
| VIII | Period 4 | Iron (Fe) | +3 | $FeO^{+3}$ (ferric)<br>$Fe(OH)^{+2}$<br>$Fe(OH)_2^+$<br>$FeO_2^{-2}$ (ferrite) | +3 Species/+4, +5, +6 Species; +4 Species/ +5, +6 Species; |
| VIII | Period 4 | Iron (Fe) | +4 | $FeO^{+2}$ (ferryl)<br>$FeO_2^{-2}$ (perferrite) | +5 Species/ +6 Species |
| | | | +5 | $FeO_2^+$ (perferryl) | |
| | | | +6 | $FeO_4^{-2}$ (ferrate) | |
| | | Cobalt (Ca) | +2 | $Co^{+2}$ (cobalous)<br>$HCoO_2^-$ (dicobaltite) | +2 Species/ +3, +4 Species; |
| | | | +3 | $Co^{+3}$ (cobaltic)<br>$Co_2O_3$ (cobaltic oxide) | +3 Species/ +4 Species |
| | | | +4 | $CoO_2$ (peroxide)<br>$H_2CoO_3$ (cobaltic acid) | |
| | | Nickel (Ni) | +2 | $Ni^{+2}$ (nickelous)<br>$NiOH^+$<br>$HNiO_2^-$ (dinickelite)<br>$NiO_2^{-2}$ (nickelite) | +2 Species/+3, +4, +6 Species; +3 Species/ +4, +6 Species; |
| | | | +3 | $Ni^{+3}$ (nickelic)<br>$Ni_2O_3$ (nickelic oxide) | +4 Species/ +6 Species |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3 |
| | | | +3 | $Ru^{+3}$<br>$Ru_2O_3$ (sesquioxide)<br>$Ru(OH)_3$ (hydroxide) | +4, +5, +6, +7, +8 Species; +3 Species/+4, |
| | | | +4 | $Ru^{+4}$ (ruthenic)<br>$RuO_2$ (ruthenic dioxide)<br>$Ru(OH)_4$ (ruthenic hydroxide) | +5, +6, +7, +8 Species; +4 Species/ |
| | | | +5 | $Ru_2O_5$ (pentoxide) | +5, +6, +7, +8 |
| | | | +6 | $RuO_4^{-2}$ (ruthenate)<br>$RuO_2^{+2}$ (ruthenyl)<br>$RuO_3$ (trioxide) | Species; +5 Species/+6, +7, +8 Species; |
| | | | +7 | $RuO_4^-$ (perruthenate) | +6 Species/ |
| | | | +8 | $H_2RuO_4$ (hyperuthenic acid)<br>$HRuO_5^-$ (diperruthenate)<br>$RuO_4$ (ruthenium tetroxide) | +7, +8 Species; +7 Species/ +8 Species |
| | | Rhodium (Rh) | +1 | $Rh^+$ (hyporhobus) | +1 Species/+2, |
| | | | +2 | $Rh^{+2}$ (rhodous) | +3, +4, +6 |
| | | | +3 | $Rh^{+3}$ (rhodic)<br>$Rh_2O_3$ (sesquioxide) | Species; +2 Species/+3, |
| | | | +4 | $RhO_2$ (rhodic oxide)<br>$Rh(OH)_4$ (hydroxide) | +4, +6 Species; +3 Species/+4, |
| | | | +6 | $RhO_4^{-2}$ (rhodate)<br>$RhO_3$ (trioxide) | +6 Species; +4 Species/+6 Species |
| | | Palladium | +2 | $Pd^{+2}$ (palladous)<br>$PdO_2^{-2}$ (palladite) | +2 Species/+3, +4, +6 Species; |
| | | | +3 | $Pd_2O_3$ (sesquioxide) | +3 Species/ |
| | | | +4 | $PdO_3^{-2}$ (palladate)<br>$PdO_2$ (dioxide)<br>$Pd(OH)_4$ (hydroxide) | +4, +6 Species; +4 Species/ |
| | | | +6 | $PdO_3$ (peroxide) | +6 Species |
| VIII | Period 6 | Iridium (Ir) | +3 | $Ir^{+3}$ (iridic)<br>$Ir_2O_3$ (iridium sesquioxide)<br>$Ir(OH)_3$ (iridium hydroxide) | +3 Species/ +4, +6 Species; +4 Species/ |
| | | | +4 | $IrO_2$ (iridic oxide)<br>$Ir(OH)_4$ (iridic hydroxide) | +6 Species |
| | | | +6 | $IrO_4^{-2}$ (iridate)<br>$IrO_3$ (iridium peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) | +4 Species/ |
| | | | | $PtO^{+2}$ (platinyl) | +6 Species |
| | | | | $Pt(OH)^{+3}$ | |
| | | | | $PtO_2$ (platonic oxide) | |
| | | | +6 | $PtO_4^{-2}$ (Perplatinate) | |
| | | | | $PtO_3$ (perplatinix oxide) | |
| IIIB | Rare earths | Cerium (Ce) | +3 | $Ce^{+3}$ (cerous) | +3 Species/ |
| | | | | $Ce_2O_3$ (cerous oxide) | +4, +6 Species; |
| | | | | $Ce(OH)_3$ (cerous hydroxide) | +4 Species/ |
| | | | +4 | $Ce^{+4}, Ce(OH)^{+3}, Ce(OH)_2^{+2}$, | +6 Species |
| | | | | $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-, UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species; |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) | +4 Species/+5, +6 Species; |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericous) | +3 Species/+4, +5, +6 Species; |
| | | | +4 | $Am^{+4}$ (americous) | +4 Species/+5, +6 Species; |
| | | | | $AmO_2$ (dioxide) | +5 Species/+6 Species |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |

TABLE II-continued

Elements Participating as Heteroatoms in Heteropolyanion Complex Anion Redox Couple Mediators

| GROUP | SUB GROUP | ELEMENT |
|---|---|---|
| V | A | Nitrogen (N), Phosphorous (P), Arsenic (As), Antimony (Sb), and Bismuth (Bi) |
|   | B | Vanadium (V), Niobium (Nb), and Tantalum (Ta) |
| VI | A | Sulfur (S), Selenium (Se), and Tellurium (Te) |
|   | B | Chromium (Cr), Molybdenum (Mo), and Tungsten (W) |
| VII | A | Fluorine (F), Chlorine (Cl), Bromine (Br), and Iodine (I) |
|   | B | Manganese (Mn), Technetium (Tc), and Rhenium (Re) |
| VIII | Period 4 | Iron (Fe), Cobalt (Co), and Nickel (Ni) |
|   | Period 5 | Ruthenium (Ru), Rhodium (Rh), and Palladium (Pd) |
|   | Period 6 | Osmium (Os), Iridium (Ir), and Platinum (Pt) |
| IIIB | Rare Earths | All | further comprising additives disposed in the electrolyte for contributing to kinetics of the mediated electrochemical processes while keeping it from becoming directly involved in the oxidizing of the animal waste materials, and stabilizer compounds disposed in the electrolyte for stabilizing higher oxidation state species of oxidized forms of the reversible redox couples used as the oxidizing species in the electrolyte, wherein the stabilizing compounds are tellurate or periodate ions.

27. Apparatus for treating and oxidizing animal waste materials comprising an electrochemical cell, an aqueous electrolyte disposed in the electrochemical cell, a semi permeable membrane, ion selective membrane, microporous membrane, porous ceramic or glass frit membrane disposed in the electrochemical cell for separating the cell into anolyte and catholyte chambers and separating the anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the animal waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
|   | B | Copper (Cu) | +2 | $Cu^{-2}$ (cupric) | +2 Species/+3, +4 Species; |
|   |   |   |   | $HCuO_2$ (bicuprite) | +3 Species/+4 Species |
|   |   |   |   | $CuO_2^{-2}$ (cuprite) | |
|   |   |   | +3 | $Cu^{+3}$ | |
|   |   |   |   | $CuO_2^{-}$ (cuprate) | |
|   |   |   |   | $Cu_2O_3$ (sesquioxide) | |
|   |   |   | +4 | $CuO_2$ (peroxide) | |
|   |   | Silver (Ag) | +1 | $Ag^{+}$ (argentous) | +1 Species/+2, +3 Species; |
|   |   |   |   | $AgO^{-}$ (argentite) | +2 Species/+3 Species |
|   |   |   | +2 | $Ag^{-2}$ (argentic) | |
|   |   |   |   | AgO (argentic oxide) | |
|   |   |   | +3 | $AgO^{+}$ (argentyl) | |
|   |   |   |   | $Ag_2O_3$ (sesquioxide) | |
|   |   | Gold (Au) | +1 | $Au^{+}$ (aurous) | +1 Species/+3, +4 Species; |
|   |   |   | +3 | $Au^{+3}$ (auric) | +3 Species/+4 Species |
|   |   |   |   | $AuO^{-}$ (auryl) | |
|   |   |   |   | $H_3AuO_3^{-}$ (auric acid) | |
|   |   |   |   | $H_2AuO_3^{-}$ (monoaurate) | |
|   |   |   |   | $HAuO_3^{-2}$ (diaurate) | |
|   |   |   |   | $AuO_3^{-3}$ (triaurate) | |
|   |   |   |   | $Au_2O_3$ (auric oxide) | |
|   |   |   |   | $Au(OH)_3$ (auric hydroxide) | |
|   |   |   | +4 | $AuO_2$ (peroxide) | |
| II | A | Magnesium (Mg) | +2 | $Mg^{+2}$ (magnesic) | +2 Species/+4 Species |
|   |   |   | +4 | $MgO_2$ (peroxide) | |
|   |   | Calcium (Ca) | +2 | $Ca^{+2}$ | +2 Species/+4 Species |
|   |   |   | +4 | $CaO_2$ (peroxide) | |
|   |   | Strontium | +2 | $Sr^{+2}$ | +2 Species/+4 Species |
|   |   |   | +4 | $SrO_2$ (peroxide) | |
|   |   | Barium (Ba) | +2 | $Ba^{+2}$ | +2 Species/+4 Species |
|   |   |   | +4 | $BaO_2$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| II | B | Zinc (Zn) | +2 | $Zn^{+2}$ (zincic) $ZnOH^+$ (zincyl) $HZnO_2^-$ (bizincate) $ZnO_2^{-2}$ (zincate) | +2 Species/+4 Species |
| | | | +4 | $ZnO_2$ (peroxide) | |
| | | Mercury (Hg) | +2 | $Hg^{+2}$ (mercuric) $Hg(OH)_2$ (mercuric hydroxide) $HHgO_2^-$ (mercurate) | +2 Species/+4 Species |
| | | | +4 | $HgO_2$ (peroxide) | |
| III | A | Boron | +3 | $H_3BO_3$ (orthoboric acid) $H_2BO_3^-$, $HBO_3^{-2}$, $BO_3^{-3}$ (orthoborates) $BO_2^-$ (metaborate) $H_2B_4O_7$ (tetraboric acid) $HB_4O_7^-/B_4O_7^{-2}$ (tetraborates) $B_2O_4^{-2}$ (diborate) $B_6O_{10}^{-2}$ (hexaborate) | +3 Species/+4.5, +5 Species |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/+3 or +3.33 Species; +3 Species/+3.33 Species |
| | | | +3 | $Tl^{+3}$ (thallic) $TlO^+$, $TlOH^{+2}$, $Tl(OH)_2^+$ (thallyl) $Tl_2O_3$ (sesquioxide) $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) $HCO_3^-$ (bicarbonate) $CO_3^{-2}$ (carbonate) | +4 Species/+5, +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) $H_2GeO_3^-$ (bigermaniate) $GeO_3^{-4}$ (germinate) $GeO^{+4}$ (germanic) $GeO_4^{-4}$ $H_2Ge_2O_5$ (digermanic acid) $H_2Ge_4O_9$ (tetragermanic acid) $H_2Ge_5O_{11}$ (pentagermanic acid) $HGe_5O_{11}^-$ (bipentagermanate) | +4 Species/+6 Species |
| | | | +6 | $Ge_5O_{11}^{-2}$ (pentagermanate) | |
| | | Tin (Sn) | +4 | $Sn^{+4}$ (stannic) $HSnO_3^-$ (bistannate) $SnO_3^{-2}$ (stannate) $SnO_2$ (stannic oxide) $Sn(OH)_4$ (stannic hydroxide) | +4 Species/+7 Species |
| | | | +7 | $SnO_4^-$ (perstannate) | |
| | | Lead (Pb) | +2 | $Pb^{+2}$ (plumbous) $HPbO_2^-$ (biplumbite) $PbOH^+$ $PbO_2^{-2}$ (plumbite) $PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic) $PbO_3^{-2}$ (metaplumbate) $HPbO_3^-$ (acid metaplumbate) $PbO_4^{-4}$ (orthoplumbate) $PbO_2$ (dioxide) | +2, +2.67, +3 Species/+4 Species |
| IV | B | Titanium | +4 | $TiO^{+2}$ (pertitanyl) $HTiO_4^-$ titanate) $TiO_2$ (dioxide) | +4 Species/+6 Species |
| | | | +6 | $TiO_2^{+2}$ (pertitanyl) $HTiO_4^-$ (acid pertitanate) $TiO_4^{-2}$ (pertitanate) $TiO_3$ (peroxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO_3$ (hafnyl) | +4 Species/+6 Species |
| | | | +6 | $HfO_3$ (peroxide) | |
| V | A | Nitrogen | +5 | $HNO_3$ (nitric acid)<br>$NO_3^-$ (nitrate) | +5 species/+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
| | | | +7 | $H_3PO_5$ (monoperphosphoric acid) | |
| V | A | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthaus)<br>$BiO^+$ (bismuthyl)<br>$BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | +5 Species/+7, +9 Species |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |
| | | | +7 | $NbO_4^-$ (perniobate)<br>$Nb_2O_7$ (perniobic oxide)<br>$HNbO_4$ (perniobic acid) | |
| | | Tantalum (Ta) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7 species |
| | | | +7 | $TaO_4^-$ (pentantalate)<br>$Ta_2O_7$ (pertantalate)<br>$HTaO_4 \cdot H_2O$ (pertantalic acid) | |
| VI | A | Sulfur (S) | +6 | $H_2SO_4$ (sulfuric acid)<br>$HSO_4^-$ (bisulfate)<br>$SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid)<br>$HSeO_4^-$ (biselenate)<br>$SeO_4^{-2}$ (selenate) | +6 species/+7 Species |
| | | | +7 | $H_2Se_2O_8$ (perdiselenic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/+4, +6 Species; +4 Species/+6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/+7 Species |
| | | | +7 | $MoO_4^-$ (permolybdate) | |
| | | Tungsten (W) | +6 | $WO_4^{-2}$ tungstic $WO_3$ (trioxide) $H_2WO_4$ (tungstic acid) | +6 Species/+8 Species |
| | | | +8 | $WO_5^{-2}$ (pertungstic) $H_2WO_5$ (pertungstic acid) | |
| VII | A | Chlorine (Cl) | +1 | HClO (hypochlorous acid) $ClO^-$ (hypochlorite) | +1 Species/+3, +5, +7 Species; +3 Species/+5, +7 Species; +5 Species/+7 Species |
| | | | +3 | $HClO_2$ (chlorous acid) $ClO_2^-$ (chlorite) | |
| | | | +5 | $HClO_3$ (chloric acid) $ClO_3^-$ (chlorate) | |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid) $BrO^-$ (hypobromitee) | +1 Species/+3, +5, +7 Species; +3 Species/+5, +7 Species; +5 Species/+7 Species |
| | | | +3 | $HBrO_2$ (bromous acid) $BrO2^-$ (bromite) | |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | +1 | HIO (hypoiodus acid) $IO^-$ (hypoiodite) | +1 Species/+3, +5, +7 Species; +3 Species/+5, +7 Species; +5 Species/+7 Species |
| | | | +3 | $HIO_2$ (iodous acid) $IO_2^-$ (iodite) | |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species; +3 Species/+4, +6, +7 Species; +4 Species/+6, +7 Species; +6 Species/+7 Species |
| | | | +3 | $Mn^{+3}$ (manganic) | |
| | | | +4 | $MnO_2$ (dioxide) | |
| | | | +6 | $MnO_4^{-2}$ (manganate) | |
| | | | +7 | $MnO_4^-$ (permanganate) | |
| VIII | Period 4 | Iron (Fe) | +3 | $Fe^{+3}$ (ferric) $Fe(OH)^{+2}$ $Fe(OH)_2^+$ $FeO_2^{-2}$ (ferrite) | +3 Species/+4, +5, +6 Species; |
| VIII | Period 4 | Iron (Fe) | +4 | $FeO^{+2}$ (ferryl) $FeO_2^{-2}$ (perferrite) | +4 Species/+5, +6 Species; +5 Species/+6 Species |
| | | | +5 | $FeO_2^+$ (perferryl) | |
| | | | +6 | $FeO_4^{-2}$ (ferrate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Cobalt (Co) | +2 | $Co^{+2}$ (cobalous)<br>$HCoO_2^-$ (dicobaltite) | +2 Species/+3, +4 Species;<br>+3 Species/+4 Species |
| | | | +3 | $Co^{+3}$ (cobaltic)<br>$Co_2O_3$ (cobaltic oxide) | |
| | | | +4 | $CoO_2$ (peroxide)<br>$H_2CoO_3$ (cobaltic acid) | |
| | | Nickel (Ni) | +2 | $Ni^{+2}$ (nickelous)<br>$NiOH^+$<br>$HNiO_2^-$ (dinickelite)<br>$NiO_2^{-2}$ (nickelite) | +2 Species/+3, +4, +6 Species;<br>+3 Species/+4, +6 Species;<br>+4 Species/+6 Species |
| | | | +3 | $Ni^{+3}$ (nickelic)<br>$Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species; |
| | | | +3 | $Ru^{+3}$ | +3 Species/+4, +5, +6, +7, +8 Species; |
| | | | | $Ru_2O_3$ (sesquioxide)<br>$Ru(OH)_3$ (hydroxide) | +4 Species/+5, +6, +7, +8 Species;<br>+5 Species/+6, +7, +8 Species; |
| | | | +4 | $Ru^{+4}$ (ruthenic)<br>$RuO_2$ (ruthenic dioxide)<br>$Ru(OH)_4$ (ruthenic hydroxide) | +6 Species/+7, +8 Species;<br>+7 Species/+8 Species |
| | | | +5 | $Ru_2O_5$ (pentoxide) | |
| | | | +6 | $RuO_4^{-2}$ (ruthenate)<br>$RuO_2^{+2}$ (ruthenyl)<br>$RuO_3$ (trioxide) | |
| | | | +7 | $RuO_4^-$ (perruthenate) | |
| | | | +8 | $H_2RuO_4$ (hyperuthenic acid)<br>$HRuO_5^-$ (diperruthenate)<br>$RuO_4$ (ruthenium tetroxide) | |
| | | Rhodium (Rh) | +1 | $Rh^+$ (hyporhodous) | +1 Species/+2, +3, +4, +6 Species; |
| | | | +2 | $Rh^{+2}$ (rhodous) | +2 Species/+3, +4, +6 Species; |
| | | | +3 | $Rh^{+3}$ (rhodic)<br>$Rh_2O_3$ (sesquioxide) | +3 Species/+4, +6 Species;<br>+4 Species/+6 Species |
| | | | +4 | $RhO_2$ (rhodic oxide)<br>$Rh(OH)_4$ (hydroxide) | |
| | | | +6 | $RhO_4^{-2}$ (rhodate)<br>$RhO_3$ (trioxide) | |
| | | Palladium | +2 | $Pd^{+2}$ (palladous)<br>$PdO_2^{-2}$ (palladite) | +2 Species/+3, +4, +6 Species;<br>+3 Species/+4, +6 Species; |
| | | | +3 | $Pd_2O_3$ (sesquioxide) | +4 Species/+6 Species |
| | | | +4 | $PdO_3^{-2}$ (palladate)<br>$PdO_2$ (dioxide)<br>$Pd(OH)_4$ (hydroxide) | |
| | | | +6 | $PdO_3$ (peroxide) | |
| VIII | Period 6 | Iridium (Ir) | +3 | $Ir^{+3}$ (iridic)<br>$Ir_2O_3$ (iridium sesquioxide)<br>$Ir(OH)_3$ (iridium hydroxide) | +3 Species/+4, +6 Species;<br>+4 Species/+6 Species |
| | | | +4 | $IrO_2$ (iridic oxide)<br>$Ir(OH)_4$ (iridic hydroxide) | |
| | | | +6 | $IrO_4^{-2}$ (iridate)<br>$IrO_3$ (iridium peroxide) | |
| | | Platinum (Pt) | +2 | $Pt^{+2}$ (platinous) | +2, +3 Species/+4, +6 Species; |
| | | | +3 | $Pt_2O_3$ (sesquioxide) | +4 Species/+6 Species |
| | | | +4 | $PtO_3^{-2}$ (palatinate)<br>$PtO^{+2}$ (platinyl)<br>$Pt(OH)^{+3}$<br>$PtO_2$ (platonic oxide) | |
| | | | +6 | $PtO_4^{-2}$ (Perplatinate)<br>$PtO_3$ (perplatinic oxide) | |
| IIIB | Rare earths | Cerium (Ce) | +3 | $Ce^{+3}$ (cerous)<br>$Ce_2O_3$ (cerous oxide)<br>$Ce(OH)_3$ (cerous hydroxide) | +3 Species/+4, +6 Species;<br>+4 Species/+6 Species |
| | | | +4 | $Ce^{+4}$, $Ce(OH)^{+3}$, $Ce(OH)_2^{+2}$,<br>$Ce(OH)_3^+$ (ceric)<br>$CeO_2$ (ceric oxide) | |
| | | | +6 | $CeO_3$ (ceric peroxide) | |
| | | Praseodymium (Pr) | +3 | $Pr^{+3}$ (praseodymous)<br>$Pr_2O_3$ (sesquioxide)<br>$Pr(OH)_3$ (hydroxide) | +3 species/+4 species |
| | | | +4 | $Pr^{+4}$ (praseodymic)<br>$PrO_2$ (dioxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-, UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species; |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species; |
| | | | +4 | $Pu^{+4}$ (plutonous) | +4 Species/+5, +6 Species; |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | +3 Species/+4, +5, +6 Species; |
| | | | +4 | $Am^{+4}$ (americous) | +4 Species/+5, +6 Species; |
| | | | | $AmO_2$ (dioxide) | +5 Species/+6 Species |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | wherein the anolyte portion further comprises super oxidizers, ions with an oxidation potential above a threshold value of 1.7 volts at 1 molar, 25° C. and pH 1, which generate inorganic free radicals in aqueous solutions, for involving in a secondary oxidation process for producing oxidizers, and organic free radicals for aiding the process and breaking down the animal waste materials into simpler smaller molecular structure organic compounds.

* * * * *